(12) United States Patent
Takeuchi et al.

(10) Patent No.: US 6,693,223 B1
(45) Date of Patent: Feb. 17, 2004

(54) FLUORINE-SUBSTITUTED-4-ALKENYLBENZOIC ACID AND DERIVATIVES THEREOF, AND NEMATIC LIQUID CRYSTAL COMPOSITION CONTAINING CYANOPHENYL BENZOATE DERIVATIVES AND LIQUID CRYSTAL DISPLAY SYSTEM USING THE SAME

(75) Inventors: Kiyofumi Takeuchi, Tokyo (JP); Haruyoshi Takatsu, Tokyo (JP); Sadao Takehara, Chiba (JP); Masashi Osawa, Saitama (JP)

(73) Assignee: Dainippon Ink and Chemicals, Inc., Tokyo (JP)

( * ) Notice: Subject to any disclaimer, the term of this patent is extended or adjusted under 35 U.S.C. 154(b) by 0 days.

(21) Appl. No.: 10/373,796

(22) Filed: Feb. 27, 2003

Related U.S. Application Data

(60) Continuation of application No. 09/826,903, filed on Apr. 6, 2001, now abandoned, which is a division of application No. 09/200,848, filed on Nov. 30, 1998, now Pat. No. 6,287,646.

(30) Foreign Application Priority Data

Nov. 28, 1997 (JP) .......................................... P. 9-327904
Oct. 29, 1998 (JP) ........................................ P. 10-308405

(51) Int. Cl.[7] .......................... C07C 25/24; C07C 63/74
(52) U.S. Cl. ....................................... 570/128; 570/129
(58) Field of Search ..................... 252/299.01; 570/129, 570/128

(56) References Cited

U.S. PATENT DOCUMENTS

| | | | |
|---|---|---|---|
| 4,455,261 A | 6/1984 | Sasaki et al. ................ | 260/465 |
| 4,551,546 A | 11/1985 | Punja .......................... | 560/124 |
| 4,818,428 A | 4/1989 | Scheulbe et al. ......... | 252/299.1 |
| 4,877,547 A | 10/1989 | Weber et al. .......... | 252/299.61 |
| 5,156,763 A | 10/1992 | Gray et al. ............ | 252/299.67 |
| 5,334,327 A | 8/1994 | Gray et al. ............ | 252/299.67 |
| 5,413,734 A | 5/1995 | Buchecker et al. ...... | 252/299.6 |
| 5,807,499 A | 9/1998 | Terashima et al. ..... | 252/299.63 |

FOREIGN PATENT DOCUMENTS

| | | |
|---|---|---|
| EP | 0 464 648 | 1/1992 |
| EP | 0 492 222 | 7/1992 |
| EP | 0 700 982 | 3/1996 |
| EP | 0 750 028 | 12/1996 |
| EP | 0 820 976 | 1/1998 |
| JP | 63-502596 | 9/1988 |
| JP | 3-503637 | 8/1991 |
| JP | 4-230352 | 8/1992 |
| JP | 4-279560 | 10/1992 |
| JP | 4-300861 | 10/1992 |
| JP | 9-59625 | 3/1997 |
| JP | 9-59637 | 3/1997 |
| JP | 9-157654 | 6/1997 |
| JP | 10-140157 | 5/1998 |
| JP | 10-158651 | 6/1998 |
| WO | 96/32365 | 10/1996 |

OTHER PUBLICATIONS

Chemical Abstracts, No. XP–002096717 (Chisso Corp.) 1986.
WPI/Derwent, No. XP–002096720, Publ. Apr. 22, 1986, (Asahi Glass Co., Ltd.).
English Translation by Computer of JP 09–59637.

*Primary Examiner*—Shean C. Wu
(74) *Attorney, Agent, or Firm*—Armstrong, Kratz, Quintos, Hanson & Brooks, LLP

(57) ABSTRACT

A novel liquid crystal compound, a nematic liquid crystal composition, and a liquid crystal display system using the composition are disclosed herein. The liquid crystal compound is represented by the general formula (I):

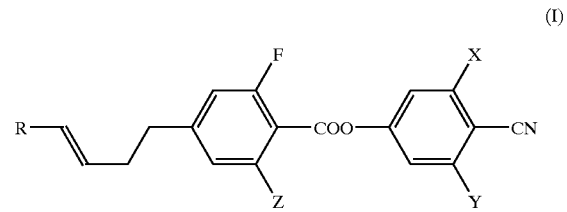

(I)

wherein R represents a hydrogen atom or a straight chain alkyl group having 1 to 7 carbon atoms and each of X, Y and Z independently represents hydrogen atom or fluorine atom. The nematic liquid crystal composition of the present invention can provide liquid crystal materials in response to desired purposes even by its addition in a small amount without spoiling other characteristics.

3 Claims, 1 Drawing Sheet

FLUORINE-SUBSTITUTED-4-ALKENYLBENZOIC ACID AND DERIVATIVES THEREOF, AND NEMATIC LIQUID CRYSTAL COMPOSITION CONTAINING CYANOPHENYL BENZOATE DERIVATIVES AND LIQUID CRYSTAL DISPLAY SYSTEM USING THE SAME

This application is a Continuation of prior application Ser. No. 09/826,903 filed Apr. 6, 2001 now abandoned, which is a Divisional of U.S. patent application Ser. No. 09/200,848 filed Nov. 30, 1998, now U.S. Pat. No. 6,287,646, which is hereby incorporated by reference.

FIELD OF THE INVENTION

This invention relates to a fluorine-substituted 4-alkenylbenzoic acid and derivatives thereof, which are useful as electro-optical display materials, and a nematic liquid crystal composition containing cyanophenyl benzoate derivatives and a liquid crystal display system using the same.

BACKGROUND OF THE INVENTION

TN-LCD (twisted nematic liquid crystal display device) is a typical liquid crystal display device and used in clocks, electronic calculators, electronic pocketbooks, pocket computers, word processors, personal computers and the like. On the other hand, with the increase in the information contents of OA instruments, STN (super twisted nematic)-LCD has been developed by Scheffer et al. (*SID '85 Digest*, p. 120, 1985) and Kinugawa et al. (*SID '86 Digest*, p. 122, 1986) and is now popularizing in the field of portable terminals, electronic pocketbooks, pocket computers, word processors, personal computers, monitor displays and the like high information displays.

Recently, an active addressing drive system (*Proc. 12th IDC*, p. 503, 1992) and multiline addressing drive system (*SID '92 Digest*, p. 232, 1992) have been proposed for the purpose of improving response characteristics of STN-LCD. Also, with the aim of achieving brighter display or higher contrast ratio, a novel reflection type liquid crystal color display system in which birefringence of liquid crystal and retardation film was used in stead of color filter layers (The Institute of Television Engineers of Japan, *Technical Reports*, vol. 14, No. 10, p. 51, 1990) and a liquid crystal display device having a refracting surface in which a small parboloid is arranged on the substrate electrode side have been proposed.

Particularly, uniform and high contrast display against the temperature distribution of back light is expected for the purpose of enlarging the display area, so that liquid crystal materials having more stable orientation and smaller temperature-dependency are expected, and a birefringence corresponding to a predetermined value is also expected for reducing dispersion of cell thickness. Since high duty drive is carried out by increasing the number of pixels, response, gradient and the like are also regarded as important factors. In the case of medium and small size portable displays, on the other hand, stability of display against working environmental temperature is an important point, so that liquid crystal materials having lower driving voltage which can reduce response and consumptive electric power are expected, as well as smaller temperature dependency of driving voltage, sharpness and frequency-dependency of desired duty drive within the temperature range of from −30 to 0° C. or from 40 to 80° C. In addition, though it is necessary to avoid too low electrical resistance (specific resistance) for saving consumptive electric power, it is required to set the resistance to a predetermined value so that it does not become too high which will cause image sticking. Thus, liquid crystal materials which are differentiated further in detail and improved even to a certain degree are still in demand.

As has been described in detail in the foregoing, there are many demands for liquid crystal display devices, such as more precise and high density display capacity, quicker response speed (switching time) against driving voltage and environmental temperature, lower driving voltage having chemically and electrically high stability, higher gradient and higher contrast for working environmental temperature and viewing angle. Because of this, research and development are still carried out on liquid crystal materials which can achieve desired driving voltage, particularly lower driving voltage, with lower viscosity so that the response property can be improved while having the nematic property within a wide range of temperature and maintaining the nematic phase for a prolonged period of time under low temperature storage conditions. In addition, designing of birefringence, dielectric anisotropy and elastic constant and their temperature-dependency, light wave length-dependency of birefringence and frequency-dependency of dielectric anisotropy in response to duty numbers are also drawing attention as means to be improved.

To meet such demands for liquid crystal materials, it is necessary to generally optimize birefringence, elastic constant, dielectric anisotropy, lower viscosity, wider nematic temperature range, chemical stability, electric stability (desired specific resistance) and the like physical characteristics and predetermined tilt angle concerning orientation property, wider d/p margin and the like individual characteristics, and the development of new liquid crystal compounds or liquid crystal compositions is still in demand.

With regard to the compounds related to the groups A1 to A3 of the present invention, which will be described in the following, compounds of the general formula (I-1) are described for example in German Patent 2306739 (1973) and *J. Phys.* (*Paris*), Suppl. 36, C1, 387 (1975), compounds of the general formula (I-4) are described in JP-A-58-83665 (1983) (the term "JP-A" as used herein means an "unexamined published Japanese patent application") and U.S. Pat. No. 4,455,261 (1984) and compounds of the general formulae (I-2), (I-3) and (I-5) to (I-9) are described in JP-W-3-503637 (the term "JP-W" as used herein means an "unexamined published Japanese international patent application") and WO 89/08102 (1989). Compositions in which these compounds are used are described for example in JP-A-9-157654 (1997) in addition to the just described references.

With regard to compounds related to the groups A4 to A6 of the present invention, which will be described in the following, compounds of the general formulae (I-10) and (I-13) are described in JP-A-2-225444 (1990), JP-A-2-233656(1990), European Patent 464648 (1991), European Patent 466183 (1991) and JP-A-4-230352 (1992), and compounds of the general formula (I-16) are described for example in JP-A-4-300861 (1992).

In addition to the aforementioned references, compositions in which these compounds are used are described for example in JP-W-62-501509 (1986), U.S. Pat. No. 4,818,426 (1989), European Patent 207975 B (1990), JP-W-63-5025969 (1987), JP-W-1-500837 (1988), JP-A-4-279560 (1992), WO 96/32365 (1996), JP-A-9-59625 (1997), JP-A-

9-227866 (1997), JP-A-10-88140. (1998), JP-A-10-140157 (1998) and JP-A-10-158651 (1998).

However, the aforementioned techniques, even some of them are unrealized, are not sufficient for achieving objects of the present invention. For example, compounds of the general formulae (I-11) and (I-12) and compounds of the general formulae (I-14) and (I-15) or the general formulae (I-17) and (I-18) of the present invention are not known. With regard to techniques concerning the compositions, descriptions about general combinations of compounds can be found illustratively, but their illustrative examples are rare, so that technical disclosures which can be used easily by those skilled in the art are not sufficient yet.

In addition, even if the aforementioned techniques are used, problems still remain unsettled. For example, great concern has been directed toward the improvement of the response property of liquid crystal display by smaller viscoelasticity in comparison with the size of dielectric anisotropy $\Delta \in$ or the realization of liquid crystal display which can be driven within a wide range of temperature by obtaining a nematic phase that is stable at a low temperature through the reduction of a crystallizing or precipitating tendency against other liquid crystal materials. Also, in the case of word processors, personal computers and the like STN-LCDs having large information capacity, small frequency dependency of driving voltage to cope with high duty, or small temperature dependency of driving voltage in the case of portable use, is expected. Because of this, more excellent new liquid crystal materials are expected.

SUMMARY OF THE INVENTION

This invention contemplates overcoming the aforementioned problems involved in the prior art.

Illustratively, its primary object is to provide a novel liquid crystal compound which is strong polar compound having large dielectric anisotropy and exerts excellent threshold voltage reducing effect and excellent miscibility with conventional liquid crystal materials by its addition.

Another object of the present invention is to provide liquid crystal materials in response to each purpose without spoiling other characteristics, including a case of its addition in a small amount. More particularly, the object is to expand operating temperature range of liquid crystal display characteristics through the improvement of miscibility, low temperature shelf life and the like, to improve reduction of driving voltage and its temperature changes and to achieve or improve relatively quick response to a desired driving voltage.

Still another object is to provide TN-LCD, STN-LCD and the like liquid crystal display systems with improved electro-optical characteristics making use of the liquid crystal compositions as constituting materials.

The present invention have found the following items as means for overcoming the aforementioned problems:

1. a compound, represented by the general formula (I):

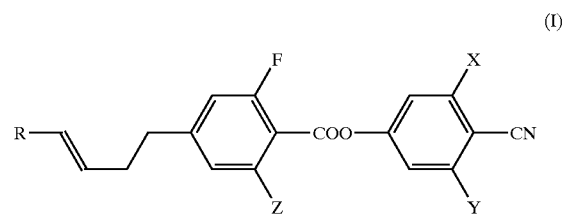

wherein R represents a hydrogen atom or a straight chain alkyl group having 1 to 7 carbon atoms and each of X, Y and Z independently represents hydrogen atom or fluorine atom.

2. The compound described in the aforementioned item 1, wherein R is a hydrogen atom or a methyl group.

3. The compound described in the aforementioned item 1 or 2, wherein X is a fluorine atom and Y is a hydrogen atom.

4. A compound, represented by the general formula (II):

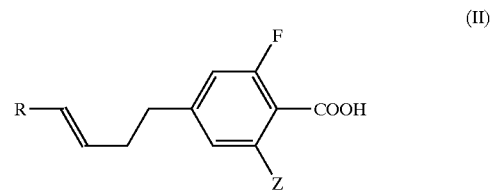

wherein R represents a hydrogen atom or a straight chain alkyl group having 1 to 7 carbon atoms and Z represents a hydrogen atom or a fluorine atom.

5. A nematic liquid crystal composition, comprising:

a liquid crystal component A composed of 1, 2 or 3 or more groups selected from groups A1 to A6, wherein said groups are composed of compounds represented by the general formulae (I-1) to (I-18):

Group A1

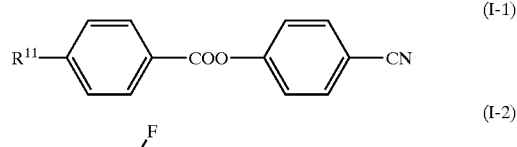

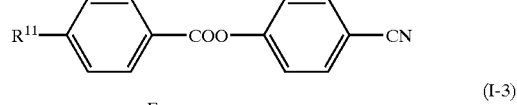

Group A2

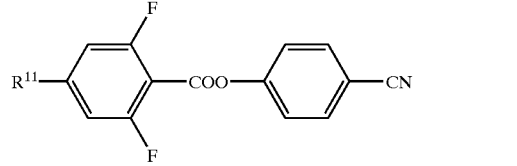

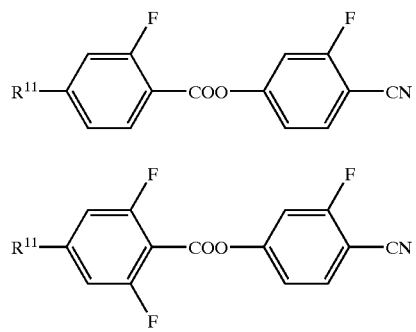

Group A3

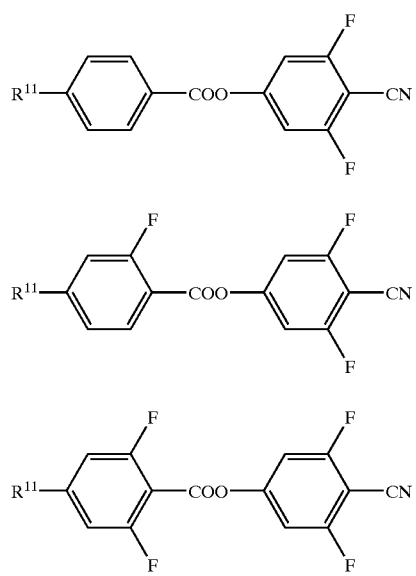

Group A4

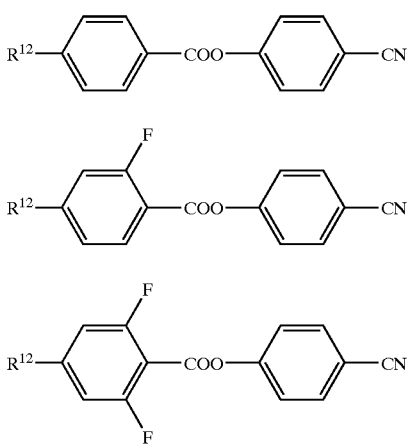

Group A5

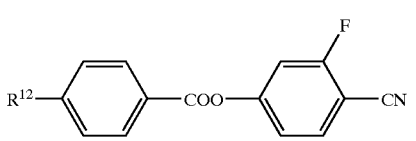

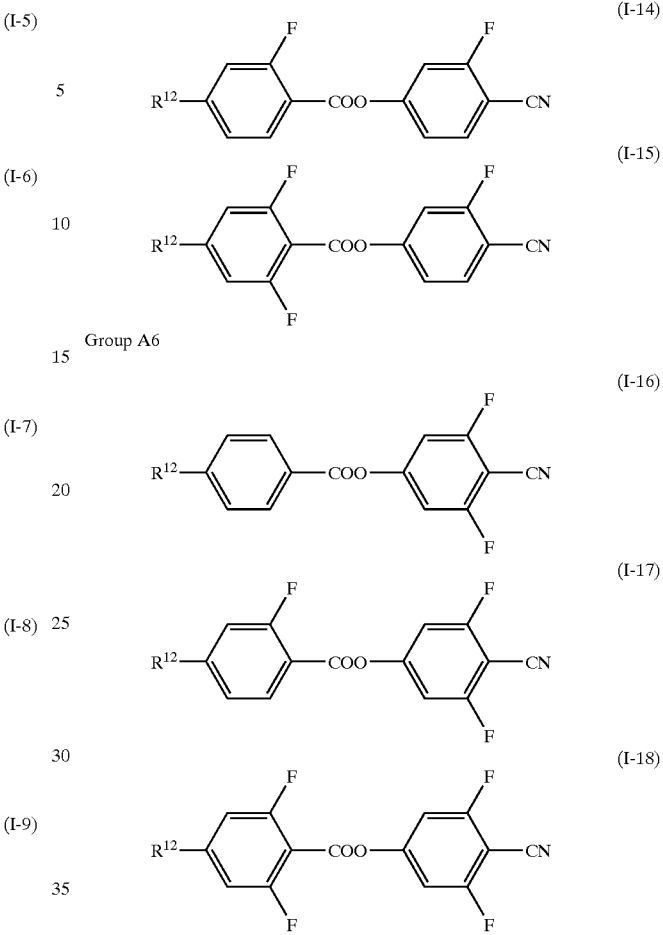

Group A6 wherein $R^{11}$ each independently represents an alkyl or alkoxy group having 1 to 10 carbon atoms and $R^{12}$ each independently represents an alkenyl or alkenyloxy group having 2 to 10 carbon atoms, wherein said alkyl group, alkoxygroup, alkenyl group or alkenyloxy group may be unsubstituted or may have one F, $CH_3$ or $CF_3$ as a substituent group, and/or at least one of $CH_2$ groups existing in said alkyl group, alkoxy group, alkenyl group or alkenyloxy group may be substituted each independently with —O—, —CO— or —COO— where O atoms are not directly linked to each other, and the atoms which constitute these compounds may be replaced by their isotopes, and said liquid crystal component A is composed of 1 to 20 compounds;

0 to 95% by weight of a liquid crystal component B composed of compounds having a dielectric anisotropy of +2 or more; and 0 to 95% by weight of a liquid crystal component C composed of compounds having a dielectric anisotropy of from −10 or more to less than +2;

wherein the total amount of the liquid crystal component B and liquid crystal component C in said nematic liquid crystal composition is from 30 to 90% by weight, with the proviso that the liquid crystal component A should satisfy at least one of the following conditions (i) to (viii):

(i) said liquid crystal component A contains at least one compound selected from the compounds represented by said general formulae (I-11), (I-12), (I-14), (I-15), (I-17) and (I-18), and the content of said compound in said liquid crystal component A is from 5 to 100% by weight;

(ii) said liquid crystal component A contains 1 to 10 of the compounds represented by the group A5 and 1 to 10 of the compounds represented by the group A4 and/or group A6, and the total content of these compounds in said liquid crystal component A is from 5 to 100% by weight;

(iii) said liquid crystal component A contains 1 to 10 of the compounds represented by the group A6 and 1 to 10 of the compounds represented by the group A4 and/or group A5, and the total content of these compounds in said liquid crystal component A is from 5 to 100% by weight;

(iv) said liquid crystal component A contains 1 to 10 of the compounds represented by the groups A4 to A6 in which the side chain group has an alkenyl group and 1 to 10 of the compounds represented by the groups A1 to A3 in which the side chain group has an alkyl group, and the total content of these compounds in said liquid crystal component A is from 5 to 100% by weight;

(v) said liquid crystal component A contains 1 to 10 of the compounds represented by the group A3 and/or group A6 having 3,5-difluoro-4-cyanophenyl group and 1 to 10 of the compounds represented by the group A2 and/or group A5 having 3-fluoro-4-cyanophenyl group, wherein at least one of these selected compounds belongs to the group A5 or group A6, and the total content of these compounds in said liquid crystal component A is from 5 to 100% by weight;

(vi) said liquid crystal component A contains 1 to 10 of the compounds represented by the group A3 and/or group A6 having 3,5-difluoro-4-cyanophenyl group and 1 to 10 of the compounds represented by the group A1 and/or group A4 having 4-cyanophenyl group, wherein at least one of these selected compounds belongs to the group A4 or group A6, and the total content of these compounds in said liquid crystal component A is from 5 to 100% by weight;

(vii) said liquid crystal component A contains 1 to 10 of the compounds represented by the group A3 and/or group A6 having 3,5-difluoro-4-cyanophenyl group, 1 to 10 of the compounds represented by the group A2 and/or group A5 having 3-fluoro-4-cyanophenyl group and 1 to 10 of the compounds represented by the group A1 and/or group A4 having 4-cyanophenyl group, and the total content of these compounds in said liquid crystal component A is from 5 to 100% by weight; and (viii) said liquid crystal component A contains 1 to 10 of compounds in which $R^{12}$ is represented by $CH_2=CH-$, $CH_2=CH-(CH_2)_2-$, $CH_2=CH-(CH_2)_4-$, $CH_3CH=CH-$, $CH_3CH=CH-(CH_2)_2-$ or $CH_3CH=CH-(CH_2)_4-$.

6. The nematic liquid crystal composition described in the aforementioned item 5, wherein said liquid crystal component B contains 1 to 15 compounds selected from the group of compounds represented by the general formulae (II-1) to (II-4):

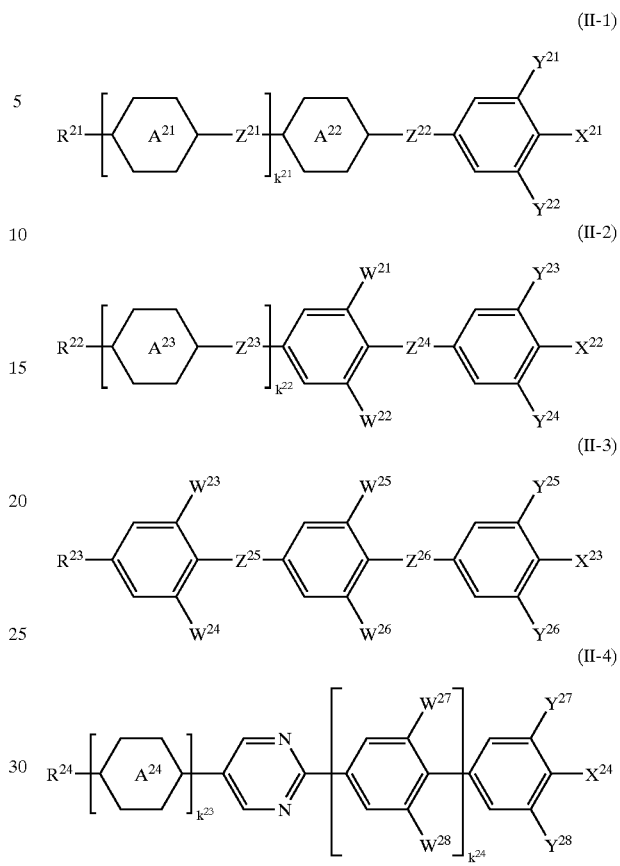

wherein each of $R^{21}$ to $R^{24}$ independently represents an alkyl group having 1 to 10 carbon atoms or an alkenyl group having 2 to 10 carbon atoms, wherein said alkyl group or alkenyl group may be unsubstituted or may have one F, $CH_3$ or $CF_3$ as a substituent group, and/or at least one of $CH_2$ groups existing in said alkyl group or alkenyl group may be substituted each independently with $-O-$, $-CO-$ or $-COO-$ where O atoms are not directly linked to each other, each of $X^{21}$ to $X^{24}$ independently represents F, Cl, $CF_3$, $OCF_3$, $OCF_2H$, NCS or CN, each of $Y^{21}$ to $Y^{28}$ independently represents H, F, Cl or $OCF_3$, each of $W^{21}$ to $W^{29}$ independently represents H, F or Cl, each of $Z^{21}$ to $Z^{26}$ independently represents a single bond, $-COO-$, $-OCO-$, $CH_2O-$, $-OCH_2-$, $-(CH_2)_2-$, $-(CH_2)_4-$, $-CH=CH-(CH_2)_2-$, $-(CH_2)_2-CH=CH-$, $-CH=N-$, $-CH=N-N=CH-$ or $-N(O)=N-$, wherein each of $Z^{21}$ and $Z^{24}$ to $Z^{26}$ may be $-CH=CH-$, $-CF=CF-$ or $-C\equiv C-$, each of the rings $A^{21}$ to $A^{24}$ independently represents trans-1,4-cyclohexylene, trans-1,4-cyclohexenylene or trans-1,3-dioxane-2,5-diyl, wherein the ring $A^{24}$ may be 1,4-phenylene, 2- or 3-fluoro-1,4-phenylene or 3,5-difluoro-1,4-phenylene, and in the case of trans-1,4-cyclohexylene, at least one of the hydrogen atoms in said ring may be replaced by deuterium atom, each of $k^{21}$ to $k^{24}$ independently represents 0 or 1 wherein $k^{23}+k^{24}$ is 0 or 1, and the atoms which constitute the compounds of said general formulae (II-1) to (II-4) may be replaced by their isotopic atoms.

7. The nematic liquid crystal composition described in the aforementioned item 6, wherein said liquid crystal component B contains 1 to 15 or more compounds selected from the group consisting of (1) a compound in which each of $R^{21}$ to $R^{24}$ in the general formulae (II-1) to (II-4) is independently an alkenyl group having 2 to 5 carbon atoms, (2) a compound in which each of $X^{21}$ to $X^{24}$ in the general formulae (II-1) to (II-4) is independently F, Cl, or $OCF_3$, (3) a compound in which $Z^{22}$ in the general formula (II-1) is $—(CH_2)_2—$ or $—(CH_2)_4—$, (4) a compound in which $k^{21}$ in the general formula (II-1) is 1, (5) a compound in which at least one of $Y^{23}$, $Y^{24}$, $W^{21}$ and $W^{22}$ in the general formula (II-2) is F, (6) a compound in which in the general formula (II-2) $k^{22}$ is 1 and $Z^{24}$ is $—C{\equiv}C—$, (7) a compound in which in the general formula (II-2) $Z^{23}$ is a single bond or $—(CH_2)_2—$ and $Z^{24}$ is $—COO—$, (8) a compound in which at least one of $Y^{25}$, $Y^{26}$ and $W^{23}$ to $W^{26}$ in the general formula (II-3) is F, (9) a compound in which $Z^{26}$ in the general formula (II-3) is $—C{\equiv}C—$, (10) a compound in which in the general formula (II-3) $Z^{25}$ is a single bond or $—C{\equiv}C—$ and $Z^{26}$ is $—COO—$, (11) a compound represented by the general formula (II-4), and (12) a compound in which in the general formulae (II-1) and (II-2) the rings $A^{21}$ to $A^{23}$ are trans-1,4-cyclohexylene and at least one of the hydrogen atoms in said ring is replaced by deuterium atom.

8. The nematic liquid crystal composition described in the aforementioned item 6, wherein said liquid crystal component B contains 1 to 15 compounds selected from the group consisting of (1) a compound in which in the general formula (II-1) $R^{21}$ is an alkyl or alkenyl group having 2 to 5 carbon atoms, $k^{21}$ is 0 and $X^{21}$ is $—CN$, (2) a compound in which in the general formula (II-1) $k^{21}$ is 1, $X^{21}$ is F or $—CN$ and each of $Y^{21}$ and $Y^{22}$ is independently H or F, (3) a compound in which in the general formula (II-2) $R^{22}$ is an alkyl or alkenyl group having 2 to 5 carbon atoms, $k^{22}$ is 0, $X^{22}$ is $—CN$ and each of $Y^{23}$, $Y^{24}$, $W^{21}$ and $W^{22}$ is independently H or F, (4) a compound in which in the general formula (II-2) $k^{22}$ is 1, $Z^{23}$ is a single bond, $—(CH_2)_2—$ or $—COO—$, $Z^{24}$ is a single bond, $—COO—$ or $—C{\equiv}C—$, $X^{22}$ is F or $—CN$ and each of $Y^{23}$, $Y^{24}$, $W^{21}$ and $W^{22}$ is independently H or F, (5) a compound in which in the general formula (II-3) $R^{23}$ is an alkyl or alkenyl group having 2 to 5 carbon atoms and one of $Z^{25}$ and $Z^{26}$ is a single bond and the other is a single bond, $—COO—$ or $—C{\equiv}C—$, (6) a compound in which each of $Y^{25}$, $Y^{26}$ and $W^{23}$ to $W^{26}$ in the general formula (II-3) is H or F, (7) a compound in which in the general formula (II-4) $R^{24}$ is an alkyl or alkenyl group having 2 to 7 carbon atoms and $k^{23}+k^{24}$ is 0, and (8) a compound in which in the general formulae (II-1) and (II-2) the rings $A^{21}$ to $A^{23}$ are trans-1,4-cyclohexylene and at least one of the hydrogen atoms in said ring is replaced by deuterium atom; and
wherein the total content of these compounds in said liquid crystal component B is from 10 to 100% by weight.

9. The nematic liquid crystal composition described in the aforementioned item 6, wherein said liquid crystal component B contains 1 to 15 compounds selected from the group consisting of (1) a compound in which in the general formula (II-1) $R^{21}$ is an alkyl or alkenyl group having 2 to 5 carbon atoms, $k^{21}$ is 1, one of $Z^{21}$ and $Z^{22}$ is a single bond and the other is a single bond, $—COO—$, $—(CH_2)_2—$ or $—(CH_2)_4—$, $X^{21}$ is F, Cl, $CF_3$, $OCF_3$ or $OCF_2H$ and at least one of $Y^{21}$ and $Y^{22}$ is F, (2) a compound in which in the general formula (II-2) $R^{22}$ is an alkyl or alkenyl group having 2 to 5 carbon atoms, $k^{22}$ is 1, $Z^{23}$ is a single bond, $—(CH_2)_2—$ or $—COO—$, $Z^{24}$ is a single bond, $—COO—$ or $—C{\equiv}C—$, $X^{22}$ is F, Cl, $CF_3$, $OCF_3$ or $OCF_2H$, at least one of $Y^{23}$ and $Y^{24}$ is F and each of $W^{21}$ and $W^{22}$ is independently H or F, (3) a compound in which in the general formula (II-3) $R^{23}$ is an alkyl or alkenyl group having 2 to 5 carbon atoms, one of $Z^{25}$ and $Z^{26}$ is a single bond and the other is a single bond, $—COO—$ or $—C{\equiv}C—$, $X^{23}$ is F, at least one of $Y^{25}$ and $Y^{26}$ is F and $W^{23}$ to $W^{26}$ are H or one or more of them are F, and (4) a compound in which in the general formulae (II-1) and (II-2) the rings $A^{21}$ to $A^{23}$ are trans-1,4-cyclohexylene and at least one of the hydrogen atoms in said ring is replaced by deuterium atom; and
wherein the total content of these compounds in said liquid crystal component B is from 10 to 100% by weight.

10. The nematic liquid crystal composition described in any one of the aforementioned items 5 to 9, wherein said liquid crystal component C contains 1 to 15 compounds selected from the group consisting of compounds represented by the general formulae (III-1) to (III-4):

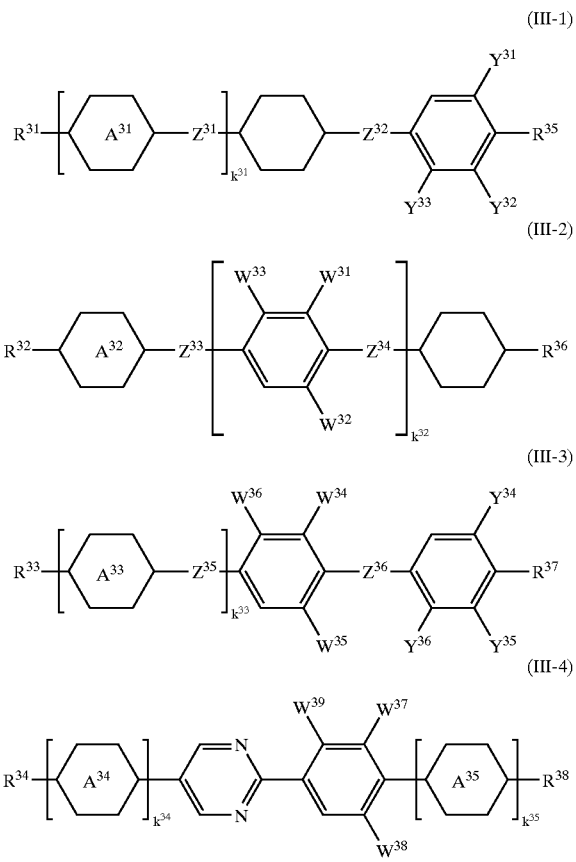

wherein each of $R^{31}$ to $R^{34}$ independently represents an alkyl or alkoxy group having 1 to 7 carbon atoms or an alkenyl or alkenyloxy group having 2 to 7 carbon atoms, wherein said alkyl group, alkoxy group, alkenyl group or alkenyloxy group may be unsubstituted or may have one F, $CH_3$ or $CF_3$ as a substituent group, and/or at least one of $CH_2$ groups existing in said alkyl group, alkoxy group, alkenyl group or alkenyloxy group may be substituted each independently with $—C—$, $—CO—$ or $—COO—$ where O atoms are not directly linked to each other, each of $Y^{31}$ to $Y^{36}$ independently represents H or F, or $Y^{33}$ and $Y^{36}$ may also be $—CH_3$, each of $W^{31}$ to $W^{39}$ independently represents H, F or Cl, each of $Z^{31}$ to $Z^{36}$ independently represents a single bond, $—COO—$, $—OCO—$, $—CH_2O—$, $OCH_2—$, $—(CH_2)_2—$, $—(CH_2)_4—$, $—CH{=}CH—(CH_2)_2—$, $—(CH_2)_2—CH{=}CH—$, $—CH{=}N—$, $—CH{=}N—N{=}CH—$ or $—N(O){=}N—$, wherein each of $Z^{31}$ and $Z^{34}$ to $Z^{36}$ may also be $—CH{=}CH—$, $—CF{=}CF—$ or $—C{\equiv}C—$, each of the rings $A^{31}$ to $A^{35}$ independently represents trans-1,4-cyclohexylene, trans-1,4-cyclohexenylene or trans-1,3-dioxane-2,5-diyl, wherein each of the rings $A^{31}$ and $A^{33}$ to $A^{35}$ may also be 1,4-phenylene, 2- or 3-fluoro-1,4-phenylene, 2,3-difluoro-1,3-phenylene or 3,5-difluoro-1,4-phenylene and, in the case of trans-1,4-cyclohexylene, at least one of the hydrogen atoms in said ring may be replaced by deuterium atom, each of $k^{31}$ to $k^{35}$ independently represents 0 or 1 wherein $k^{34}+k^{35}$ is 0 or 1, and the atoms which constitute the compounds of said general formulae (III-1) to (III-4) may be replaced by their isotopic atoms.

11. The nematic liquid crystal composition described in the aforementioned item 10, wherein said liquid crystal component C contains 1 to 15 compounds selected from the group consisting of the compounds represented by the general formula (III-1), (III-2) or (III-3), and the total content of these compounds in said liquid crystal component C is from 10 to 100% by weight.

12. The nematic liquid crystal composition described in the aforementioned item 10, wherein said liquid crystal component C contains 1 to 15 or more compounds selected from the group consisting of (1) a compound in which each of $R^{31}$ to $R^{34}$ in the general formulae (III-1) to (III-4) is independently an alkenyl group having 2 to 5 carbon atoms, (2) a compound in which each of $R^{35}$ to $R^{38}$ in the general formulae (III-1) to (III-4) is independently a straight chain alkenyl or alkenyloxy group having 2 to 7 carbon atoms, (3) a compound in which in the general formula (III-1) $k^{31}$ is 0 and $Z^{32}$ is a single bond or —(CH$_2$)$_2$—, (4) a compound in which $k^{31}$ in the general formula (III-1) is 1, (5) a compound represented by the general formula (III-2), (6) a compound in which in the general formula (III-3) at least one of $Y^{34}$, $Y^{35}$ and $W^{34}$ to $W^{36}$ is F and $Y^{33}$ is F or —CH$_3$, (7) a compound in which in the general formula (III-3) $k^{33}$ is 0 and $Z^{36}$ is a single bond, (8) a compound in which in the general formula (III-3) $k^{33}$ is 1 and $Z^{35}$ is a single bond, —OCO—, —CH$_2$O—, OCH$_2$—, —(CH$_2$)$_2$—, —(CH$_2$)$_4$—, —CH═CH—(CH$_2$)$_2$—, —(CH$_2$)$_2$—CH═CH—, —CH═N—, —CH═N—N═CH—, —N(O)═N—, —CH═CH— or —CF═CF—, (9) a compound in which in the general formula (III-3) $Z^{35}$ is —COO— or —C≡C— and $Z^{36}$ is —OCO—, —CH$_2$O—, —OCH$_2$—, —(CH$_2$)$_2$—, —(CH$_2$)$_4$—, —CH═CH—(CH$_2$)$_2$—, —(CH$_2$)$_2$—CH═CH—, —CH═N—, —CH═N—N═CH—, —N(O)═N—, —CH═CH—, —CF═CF— or —C≡C—, (10) a compound represented by the general formula (III-4), and (11) a compound in which in the general formulae (III-1) to (III-4) the rings $A^{31}$ to $A^{35}$ are trans-1,4-cyclohexylene and at least one of the hydrogen atoms in said ring is replaced by deuterium atom.

13. The nematic liquid crystal composition described in the aforementioned item 10, wherein said liquid crystal component C contains 1 to 15 compounds selected from the group consisting of (1) a compound in which in the general formula (III-1) $R^{31}$ is an alkyl group having 1 to 5 carbon atoms or an alkenyl group having 2 to 5 carbon atoms, $R^{35}$ is an alkyl or alkoxy group having 1 to 5 carbon atoms or an alkenyl or alkenyloxy group having 2 to 5 carbon atoms, $k^{31}$ is 0 and $Z^{32}$ is a single bond, —COO— or —(CH$_2$)$_2$—, (2) a compound in which in the general formula (III-1) $k^{31}$ is 1, the ring $A^{31}$ is trans-1,4-cyclohexylene and one of $Z^{31}$ and $Z^{32}$ is a single bond and the other is —COO— or —(CH$_2$)$_2$—, (3) a compound in which in the general formula (III-2) $R^{32}$ is an alkyl group having 1 to 5 carbon atoms or an alkenyl group having 2 to 5 carbon atoms, $R^{36}$ is an alkyl or alkoxy group having 1 to 5 carbon atoms or an alkenyl or alkenyloxy group having 2 to 5 carbon atoms, the ring $A^{32}$ is trans-1,4-cyclohexylene or trans-1,4-cyclohexenylene, $k^{32}$ is 0 and $Z^{33}$ is a single bond, —COO— or —(CH$_2$)$_2$—, (4) a compound in which in the general formula (III-2) $k^{32}$ is 1 and one of $Z^{33}$ and $Z^{34}$ is a single bond, (5) a compound in which in the general formula (III-3) $R^{33}$ is an alkyl group having 1 to 5 carbon atoms or an alkenyl group having 2 to 5 carbon atoms, $R^{37}$ is an alkyl or alkoxy group having 1 to 5 carbon atoms or an alkenyl or alkenyloxy group having 2 to 5 carbon atoms, $k^{33}$ is 0 and $Z^{36}$ is a single bond, —C≡C— or —CH═N—N═CH—, (6) a compound in which in the general formula (III-3) $k^{33}$ is 1 $Z^{35}$ is a single bond, —(CH$_2$)$_2$, —COO— or —C≡C— and $Z^{36}$ is a single bond, —COO— or —C≡C—, (7) a compound in which in the general formula (III-3) one of $Z^{35}$ and $Z^{36}$ is a single bond and the other is a single bond or —C≡C— and at least one of $W^{34}$ and $W^{35}$ is F, (8) a compound in which in the general formula (III-3) either one of $Y^{35}$ and $Y^{36}$ is substituted with F or CH$_3$, and (9) a compound in which in the general formula (III-4) $R^{34}$ is an alkyl group having 1 to 5 carbon atoms or an alkenyl group having 2 to 5 carbon atoms, $R^{38}$ is an alkyl or alkoxy group having 1 to 5 carbon atoms or an alkenyl or alkenyloxy group having 2 to 5 carbon atoms and $k^{34}+k^{35}$ is 0, and wherein the total content of these compounds in said liquid crystal component C is from 10 to 100% by weight.

14. The nematic liquid crystal composition described in any one of the aforementioned items 5 to 13, wherein said liquid crystal composition contains 1 to 10 compounds having a core structure of four six membered rings and having a liquid crystal phase-isotropic liquid phase transition temperature of 100° C. or more.

15. The nematic liquid crystal composition described in any one of the aforementioned items 5 to 14, wherein said liquid crystal composition has a birefringence of from 0.08 to 0.195, an elastic constant ratio $K_{33}/K_{11}$ of from 1.1 to 4.0, a nematic phase-isotropic liquid phase transition temperature of from 50 to 150° C. and a crystal phase-, smectic phase- or glass phase-nematic phase transition temperature of from −200° C. to 0° C.

16. The nematic liquid crystal composition described in any one of the aforementioned items 5 to 15, wherein said liquid crystal composition further contains a compound having an optically active group which shows an induced helical pitch of from 0.5 to 1,000 μm.

17. An active matrix, twisted nematic or super twisted nematic liquid crystal display system comprising the nematic liquid crystal composition described in the aforementioned item 16.

DETAILED DESCRIPTION OF THE INVENTION

Figure 1:
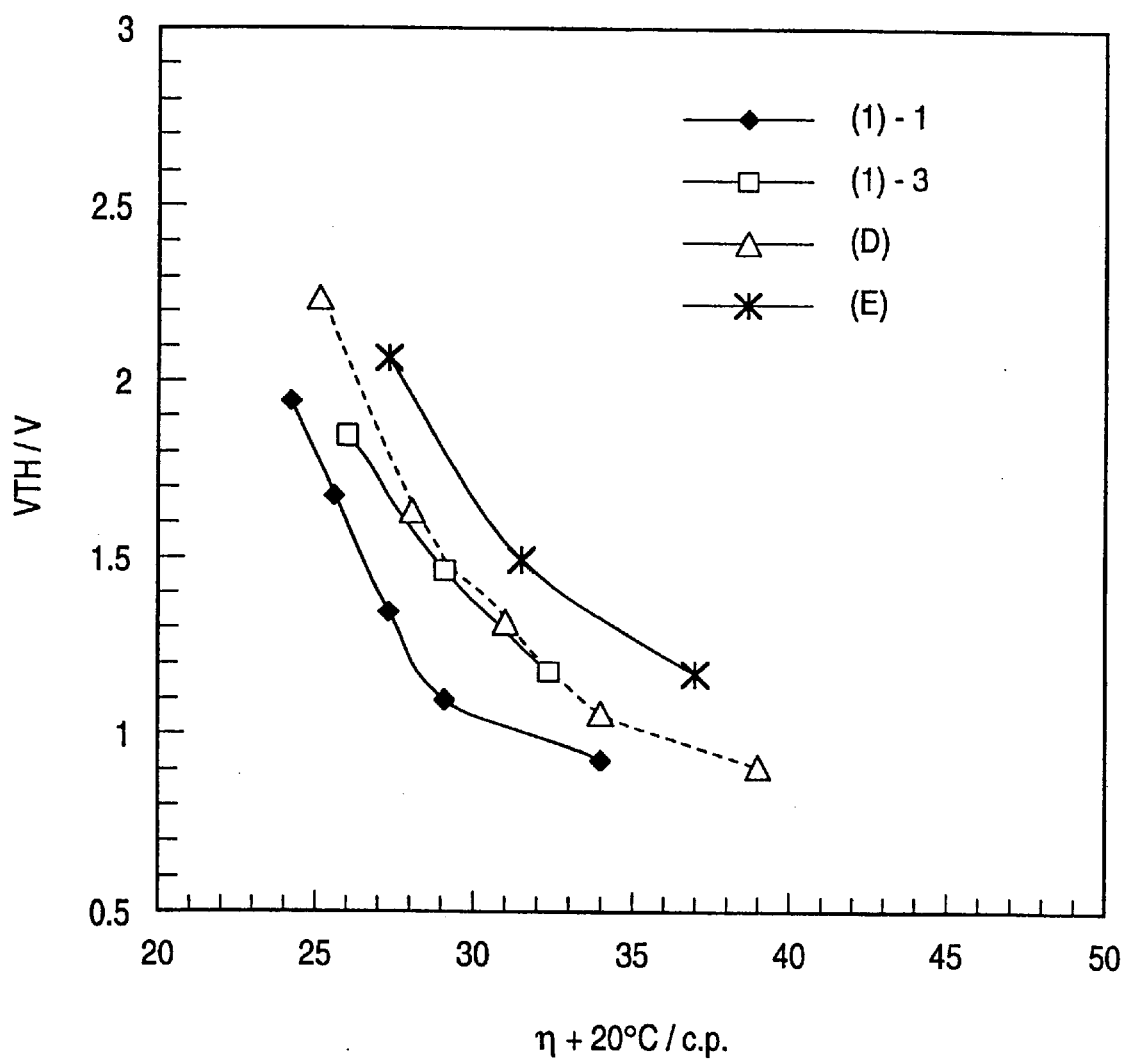
FIG. 1 is a graph showing a relationship between viscosity (η) at 20° C. and threshold voltage (Vth), measured in Example 7 and Comparative Example 4.

The following describes an example of the present invention.

The liquid crystal composition of the present invention contains component A as an essential component which comprises compounds selected from the compounds represented by the general formulae (I-1) to (I-18). The component A is characterized in that it is constructed by classifying it into groups A1 to A6. The groups A1 to A6 are classified by dividing the compounds of general formulae (I-1) to (I-18) into a group having 3,5-difluoro-4-cyanophenyl group, a group having 3-fluoro-4-cyanophenyl group and a group having 4-cyanophenyl group taking note of the polar groups and further into a group having for example an alkenyl group and a group having for example an alkyl group taking note of the side chain group. The liquid crystal component A is selected from the groups A1 to A6. These groups may be selected as one group, two groups or three or more groups in response to each purpose. The present invention has found that its objects can be achieved by grouping the compounds of general formulae (I-1) to (I-18) in view of the above points, and constituting the liquid crystal component A in such a manner that characteristics of these groups become more suitable. More illustratively, when the liquid crystal component A having the aforementioned characteristics is blended in a liquid crystal composition, the resulting mixture shows excellent characteristics which cannot be found in the conventional driving voltage-reducing liquid crystal compounds, because it shows a relatively good nematic phase-isotropic liquid phase transition temperature and has an effect to reduce driving voltage while keeping or without spoiling the response property.

The liquid crystal composition of the present invention also has the following characteristics. The liquid crystal component A of the present invention has a feature in that it has markedly large dielectric anisotropy Δε. Because of this, the liquid crystal composition of the present invention has a feature in that driving can be effected at a low voltage due to the ability to adjust the dielectric anisotropy Δε within a wide range. In general, a compound having markedly large dielectric anisotropy Δ∈ also has a disadvantage of causing high viscosity. The present invention, however, has found an effect that lower viscosity can be achieved for the size of dielectric anisotropy, by a combination of the composition in which it contains the aforementioned liquid crystal component A, 0 to 95% by weight of a liquid crystal component B composed of compounds having a dielectric anisotropy of +2 or more and 0 to 95% by weight of a liquid crystal component C composed of compounds having a dielectric anisotropy of from −10 or more to less than +2, wherein the total amount of the liquid crystal component B and liquid crystal component C is from 30 to 95% by weight. Also, when mixed with a liquid crystal material consisting of the above-described liquid crystal component B and liquid crystal component C, operating temperature range of the liquid crystal component A can be adjusted more widely for example by reducing solid phase- or smectic phase-nematic phase transition temperature or prolonging storage time at a low temperature.

The liquid crystal component A contains one or more compounds selected from the compounds of general formulae (I-1) to (I-18), and it is desirable to constitute the component with 1 to 20 compounds in response to each purpose. In that case, one or more compounds can be selected from the same group, but it also is possible to select a plurality of compounds from compounds represented by the same general formula or from two or three different general formulae. The compounds selected from the same group can be constituted by 1 to 20 species, but more desirably by 1 to 10 species.

The compounds of group A3 and A6, when strictly compared with compounds of other groups, have excellent effect to reduce driving voltage, but have a tendency to worsen response property and make nematic phase-isotropic liquid phase transition temperature lower. In consequence, it is desirable to reduce the number of the compounds of group A3 and group A6 as small as possible; illustratively, it is desirable to constitute them with 1 to 10 species, more desirably with 1 to 5 species, most desirably with 3, 2 or 1 species.

More preferred modes of the compounds represented by the general formulae (I-1) to (I-18) are shown in the following. More preferred mode of the side chain group $R^{11}$ is general formulae (I-a) to (I-ag) shown in the following, and more preferred mode of the side chain group $R^{12}$ is general formulae (I-ah) to (I-bc) shown in the following. Compounds represented by these groups are useful.

| | |
|---|---|
| (I-a) | $C_2H_5-$ |
| (I-b) | $C_3H_7-$ |
| (I-c) | $C_4H_9-$ |
| (I-d) | $C_5H_{11}-$ |
| (I-e) | $C_6H_{13}-$ |
| (I-f) | $C_7H_{15}-$ |
| (I-g) | $C_2H_5O-$ |
| (I-h) | $C_3H_7O-$ |
| (I-i) | $C_4H_9O-$ |
| (I-j) | $C_5H_{11}O-$ |
| (I-k) | $C_6H_{13}O-$ |
| (I-l) | $C_7H_{15}O-$ |
| (I-m) | $C_2H_5COO-$ |
| (I-n) | $C_3H_7COO-$ |
| (I-o) | $C_4H_9COO-$ |
| (I-p) | $C_5H_{11}COO-$ |
| (I-q) | $C_6H_{13}COO-$ |
| (I-r) | $C_7H_{15}COO-$ |
| (I-s) | $CH_3OCH_2-$ |
| (I-t) | $CH_3OC_2H_4-$ |
| (I-u) | $CH_3OC_3H_6-$ |
| (I-v) | $CH_3OC_4H_8-$ |
| (I-w) | $CH_3OC_5H_{10}-$ |
| (I-x) | $C_2H_5OCH_2-$ |
| (I-y) | $C_2H_5OC_2H_4-$ |
| (I-z) | $C_2H_5OC_3H_6-$ |
| (I-aa) | $C_2H_5OC_4H_8-$ |
| (I-ab) | $C_2H_5OC_5H_{10}-$ |
| (I-ac) | $C_3H_7OCH_2-$ |
| (I-ad) | $C_3H_7OC_2H_4-$ |
| (I-ae) | $C_3H_7OC_3H_6-$ |
| (I-af) | $C_3H_7OC_4H_8-$ |
| (I-ag) | $C_3H_7OC_5H_{10}-$ |
| (I-ah) | $CH_2=CH-$ |
| (I-ai) | $CH_3CH=CH-$ |
| (I-aj) | $C_2H_5CH=CH-$ |
| (I-ak) | $C_3H_7CH=CH-$ |
| (I-al) | $CH_2=CHC_2H_4-$ |
| (I-am) | $CH_3CH=CHC_2H_4-$ |
| (I-an) | $CH_2=CHCH_2-$ |
| (I-ao) | $CH_2=CHO-$ |
| (I-ap) | $CH_3CH=CHO-$ |
| (I-aq) | $C_2H_5CH=CHO-$ |
| (I-ar) | $C_3H_7CH=CHO-$ |
| (I-as) | $CH_2=CHC_2H_4O-$ |
| (I-at) | $CH_3CH=CHC_2H_4O-$ |
| (I-au) | $CH_2=CHCH_2O-$ |
| (I-av) | $CHF=CH-$ |
| (I-aw) | $CH_2=CF-$ |
| (I-ax) | $CF_2=CH-$ |
| (I-ay) | $CHF=CF-$ |
| (I-az) | $CHF=CHC_2H_4-$ |
| (I-ba) | $CH_2=CFC_2H_4-$ |
| (I-bb) | $CF_2=CHC_2H_4-$ |
| (I-bc) | $CHF=CFC_2H_4-$ |

In this connection, each of the compounds used in the following was thoroughly purified by removing impurities using distillation, column purification, recrystallization and the like techniques.

In describing further in detail, it is desirable to use the following compounds in the liquid crystal component A to obtain the effects of the present invention.

In the general formulae (I-1) to (I-9), (I-i): preferred are compounds in which $R^{11}$ is an alkyl group having 2 to 7 carbon atoms, illustratively, compounds having basic structures of the general formulae (I-1) to (I-9) and side chain groups of (I-a) to (I-l) and (I-s) to (I-ag), more preferably having side chain groups of (I-a) to (I-f), (I-s) to (I-x) and (I-ac). Since these compounds have the effect to reduce driving voltage, and elastic constants and their ratios $K_{33}/K_{11}$ and $K_{33}/K_{22}$ can be controlled, further improved electro-optical characteristics of TN-LCD, STN-LCD and the like devices can be obtained.

Also, in the general formulae (I-10) to (I-18), (I-ii): preferred are compounds in which $R^{12}$ is an alkenyl group having 2 to 7 carbon atoms, illustratively, compounds having basic structures of the general formulae (I-10) to (I-18) and side chain groups of (I-ah) to (I-bc), more preferably having side chain groups of (I-al) to (I-an), (I-as) to (I-au) and (I-az) to (I-bc). Most preferred is a nematic liquid crystal composition which contains 1 to 10 compounds in which $R^{12}$ is represented by $CH_2=CH-$, $CH=H-(CH_2)_2$, $CH_2=CH-(CH_2)_4-$, $CH_3CH=CH-$, $CH_3CH=CH-(CH_2)_2-$ or $CH_3CH=CH-(CH_2)_4-$. Since these compounds have the effect to reduce driving voltage while keeping or without worsening nematic phase-isotropic liquid phase transition temperature and response property, operating temperature range can be expanded through the improvement of miscibility and low temperature shelf life of the liquid crystal composition and elastic constants and their ratios $K_{33}/K_{11}$ and $K_{33}/K_{22}$ can be controlled, so that electro-optical characteristics of TN-LCD, STN-LCD and the like devices with improved sharpness, response or temperature characteristics can be obtained.

In order to cause the effect to reduce driving voltage or its temperature dependency or frequency dependency of driving voltage in response to high duty, (I-iii): it is desirable to use mainly compounds represented by the group A3 and/or group A6 having 3,5-difluoro-4-cyanophenyl group and compounds represented by the group A2 and/or group A5 having 3-fluoro-4-cyanophenyl group. In that case, it is more desirable to select compounds in which $R^{11}$ is (I-a) to (I-f), (I-s) to (I-x) or (I-ac) and compounds in which $R^{12}$ is (I-al) to (I-an), (I-as) to (I-au) or (I-az) to (I-bc).

In order to reduce driving voltage while keeping or without worsening nematic phase-isotropic liquid phase transition temperature and response property, (I-iv): it is desirable to use mainly compounds of the general formulae (I-3), (I-6), (1-12) and (I-15) having 3,5-difluoro-1,4-phenylene group and compounds of the general formulae (I-2), (I-5), (I-18), (I-11), (I-14) and (I-17) having 3-fluoro-1,4-phenylene group.

A liquid crystal component A which contains one or two or more of compounds selected from these subgroups (I-i) to (I-iv) is desirable. Particularly, a liquid crystal component A in which compounds having alkenyl groups as the side chain groups are selectively combined or a liquid crystal component A in which compounds having alkyl groups and alkenyl groups are simultaneously selected are desirable in terms of the sharpness and response of STN-LCD or temperature characteristics thereof. Also, a liquid crystal component A in which compounds having 3,5-difluoro-4-cyanophenyl group as the polar group and compounds having 3-fluoro-4-cyanophenyl group are simultaneously selected is desirable, because driving voltage can be reduced while improving problems concerning miscibility. In view of such points, it is desirable that the liquid crystal component A is composed of groups A1 to A6 and satisfies at least one of the following conditions.

(i) The liquid crystal component A contains at least one compound selected from the compounds represented by the general formulae (I-11), (I-12), (I-14), (I-15), (I-17) and (I-18), and the content of the compound in the liquid crystal component A is from 5 to 100% by weight. This construction can exert the aforementioned effects concerning subgroups (I-ii) to (I-iv).

(ii) The liquid crystal component A contains 1 to 10 of the compounds represented by the group A5 and 1 to 10 of the compounds represented by the group A4 and/or group A6, and the total content of both of these compounds in the liquid crystal component A is from 5 to 100% by weight.

(iii) The liquid crystal component A contains 1 to 10 of the compounds represented by the group A6 and 1 to 10 of the compounds represented by the group A4 and/or group A5, and the total content of both of these compounds in the liquid crystal component A is from 5 to 100% by weight.

In the above constructions, a combination of a group having 3,5-difluoro-4-cyanophenyl group with a group having 3-fluoro-4-cyanophenyl group and/or a group having 4-cyanophenyl group is used taking note of the polar groups, and a group having an alkenyl group is used as the main component taking note of the side chain group. This construction can exert the aforementioned effects concerning subgroups (I-ii) to (I-iv).

(iv) The liquid crystal component A contains 1 to 10 of the compounds represented by the groups A4 to A6 in which the side chain group has an alkenyl group and 1 to 10 of the compounds represented by the groups A1 to A3 in which the side chain group has an alkyl group, and the total content of these compounds in the liquid crystal component A is from 5 to 100% by weight.

(v) The liquid crystal component A contains 1 to 10 of the compounds represented by the group A3 and/or group A6 having 3,5-difluoro-4-cyanophenyl group and 1 to 10 of the compounds represented by the group A2 and/or group A5 having 3-fluoro-4-cyanophenyl group, wherein at least one of these selected compounds belongs to the group A5 or group A6, and the total content of these compounds in the liquid crystal component A is from 5 to 100% by weight.

(vi) The liquid crystal component A contains 1 to 10 of the compounds represented by the group A3 and/or group A6 having 3,5-difluoro-4-cyanophenyl group and 1 to 10 of the compounds represented by the group A1 and/or group A4 having 4-cyanophenyl group, wherein at least one of these selected compounds belongs to the group A4 or group A6, and the total content of these compounds in the liquid crystal component A is from 5 to 100% by weight.

In the above constructions, a combination of a group having 3,5difluoro-4-cyanophenyl group with a group having 3-fluoro-4-cyanophenyl group and/or a group having 4-cyanophenyl group is used taking note of the polar groups, and a group having an alkenyl group and a group having an alkyl group are jointly used taking note of the side chain group. This construction can exert the aforementioned effects concerning subgroups (I-i) to (I-iv).

(vii) The liquid crystal component A contains 1 to 10 of the compounds represented by the group A3 and/or group A6 having 3,5-difluoro-4-cyanophenyl group, 1 to 10 of the compounds represented by the group A2 and/or group A5 having 3-fluoro-4-cyanophenyl group and 1 to 10 of the compounds represented by the group A1 and/or group A4 having 4-cyanophenyl group, and the total content of these compounds in the liquid crystal component A is from 5 to 100% by weight.

In the above construction, a group having 3,5-difluoro-4-cyanophenyl group, a group having 3,5-fluoro-4-cyanophenyl group and a group having 4-cyanophenyl group are jointly used taking note of the polar groups. This construction can exert the aforementioned effects concerning the subgroup (I-iv).

According to the present invention, one or more compounds optionally selected from the groups A1 to A6 can be included as the liquid crystal component A, but the aforementioned effects can be obtained even by a single compound. Preferably, depending on the desired purpose, it may be constructed with the aforementioned compounds (i) to (viii). Since the liquid crystal composition of the present invention containing such a liquid crystal component A can expand operating temperature range of the liquid crystal display characteristics through the improvement of miscibility and low temperature shelf life, improve reduction of driving voltage and temperature changes thereof and achieve or improve relatively quick response for a desired driving voltage, further improved electro-optical characteristics, particularly more desirable low temperature-dependency, can be added to TN-LCD, STN-LCD and the like devices in which such a composition is used.

In addition to the aforementioned liquid crystal component A, the liquid crystal composition of the present invention contains a liquid crystal component B which contains at least one compound having a dielectric anisotropy of +2 or more. In this connection, the term "liquid crystal compound having a dielectric anisotropy of +2 or more" as used herein means as follows. That is, the liquid crystal compound has a rod-shaped chemical structure in which its central part has a core structure having 1 to 4 six-membered rings, six-membered rings positioned at both termini of the central part in major axis direction have terminal groups substituted at positions corresponding to the major axis of the liquid crystal molecule and at least one of the terminal groups positioned at both termini is a polar group such as —F, —Cl, —$NO_2$, —$CF_3$, $OCF_3$, $OCHF_2$, —CN, —OCN, —NCS or the like group. By such a structure, optical anisotropy of the liquid crystal layer can be controlled at a desired value, electrical drive can be made and operating temperature range can be expanded.

In the liquid crystal component B, at least 1 species, preferably from 3 to 15 species, can be used as the compound having a dielectric anisotropy of +2 or more. Also, it is desirable to use the compound by optionally selecting from compounds having a dielectric anisotropy of from +2 to +6, compounds having a dielectric anisotropy of from +8 to +13, compounds having a dielectric anisotropy of from +14 to +18 and compounds having a dielectric anisotropy of +18 or more, by which desired driving voltage and response characteristics can be obtained. In that case, it is desirable to mix compounds having a dielectric anisotropy of from +2 to +13 within the range of 10 or less species at the most, to mix compounds having a dielectric anisotropy of from +14 to +18 within the range of 8 or less species at the most or to mix compounds having a dielectric anisotropy of from +18 or more within the range of 10 or less species at the most. The use of the liquid crystal component B in the aforementioned manner gives temperature characteristics of the display characteristics more desirable effects. More illustratively, it improves driving voltage, sharpness-related contrast and response or the like temperature-dependency to more desirable levels.

In view of such points, more preferred modes of the basic structures in the compounds represented by the general formulae (II-1) to (II-4) are compounds represented by the following general formulae (II-1a) to (II-4g).

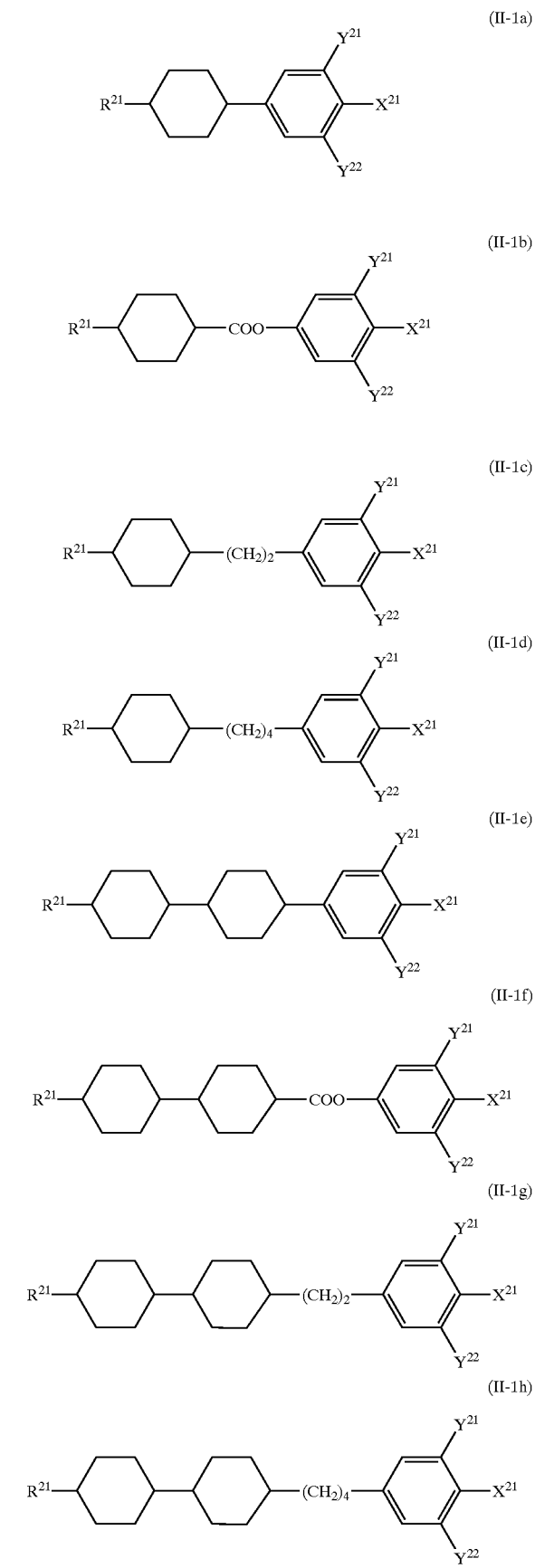

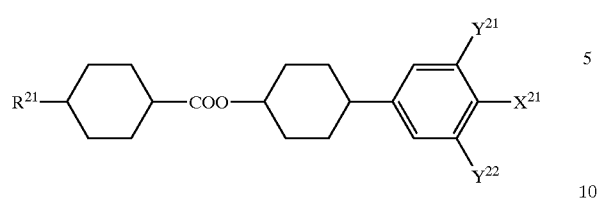
(II-1i)
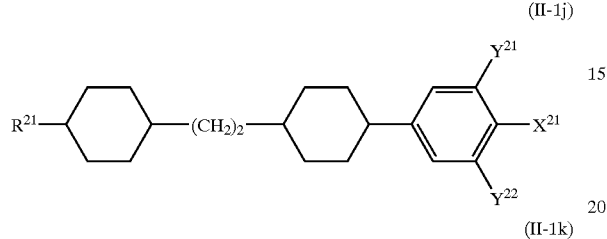
(II-1j)
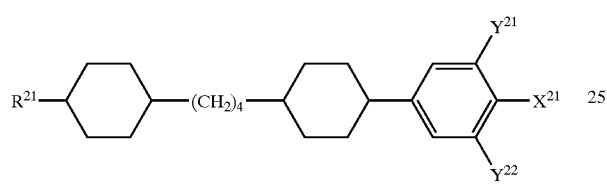
(II-1k)
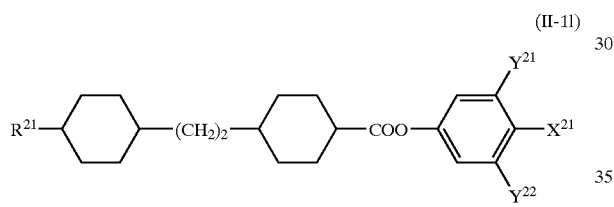
(II-1l)
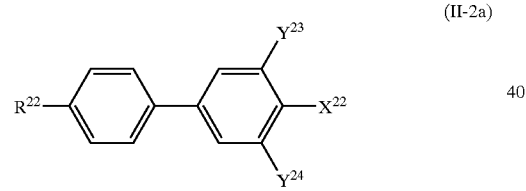
(II-2a)
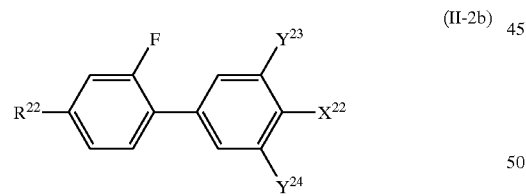
(II-2b)
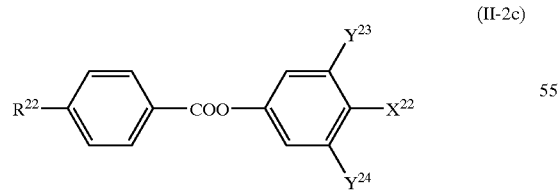
(II-2c)
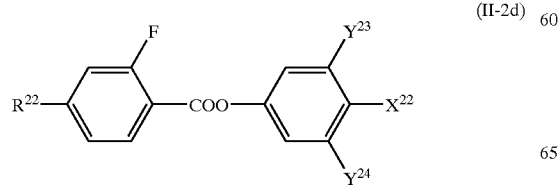
(II-2d)
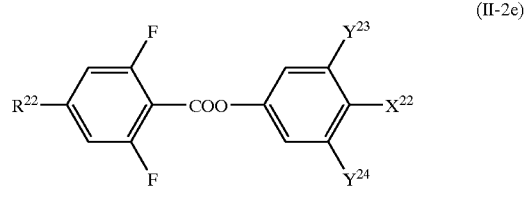
(II-2e)
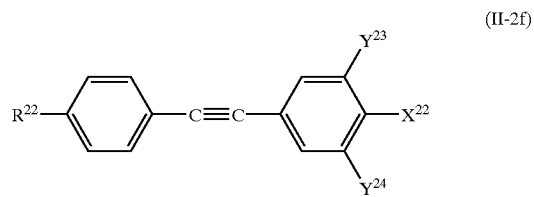
(II-2f)
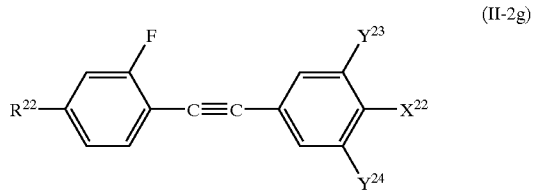
(II-2g)
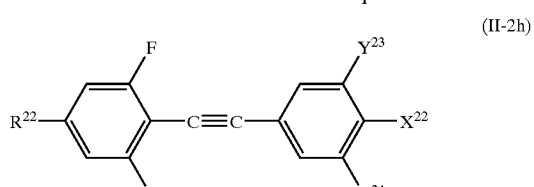
(II-2h)
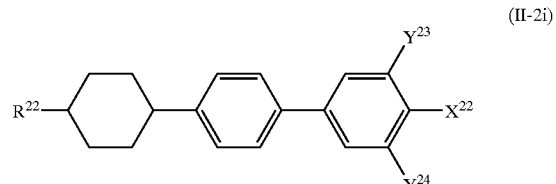
(II-2i)
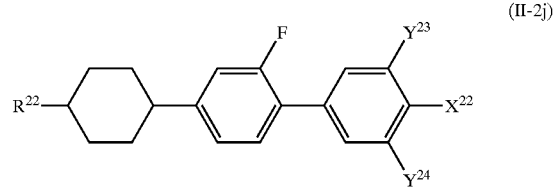
(II-2j)
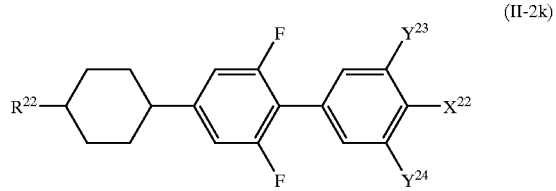
(II-2k)
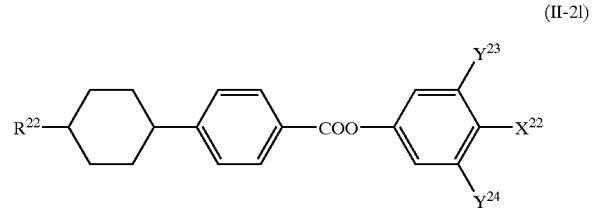
(II-2l)

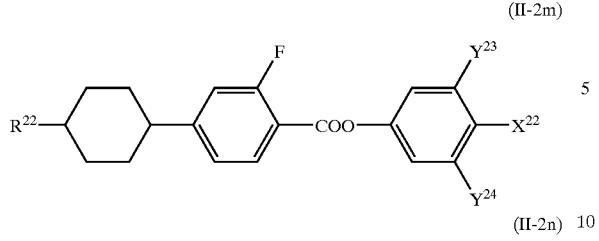
(II-2m)
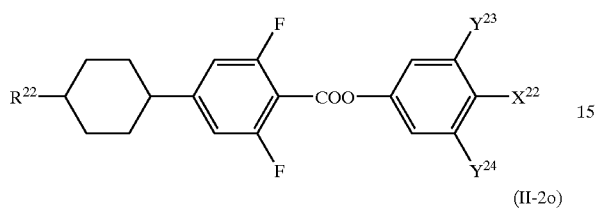
(II-2n)
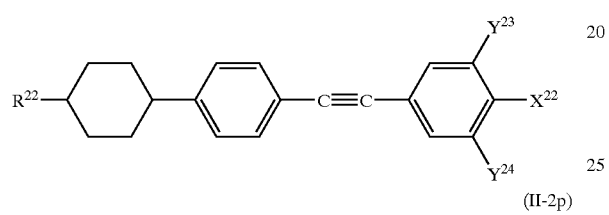
(II-2o)
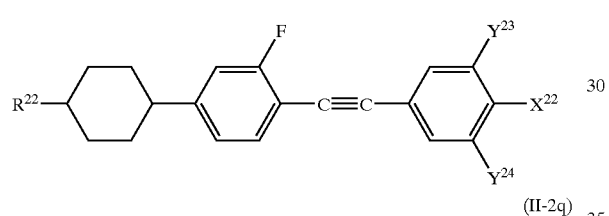
(II-2p)
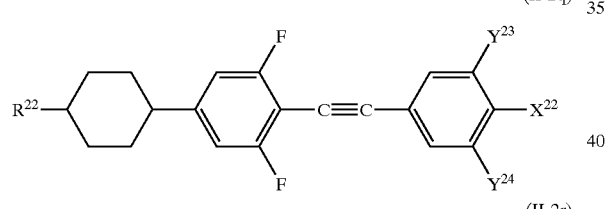
(II-2q)
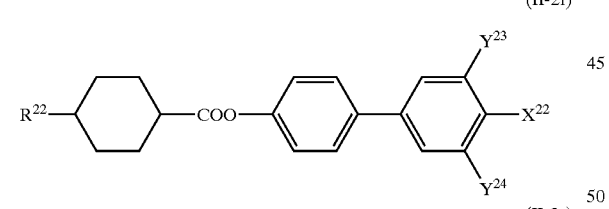
(II-2r)
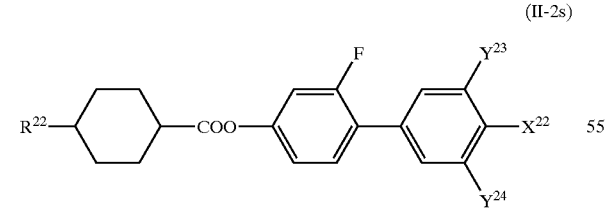
(II-2s)
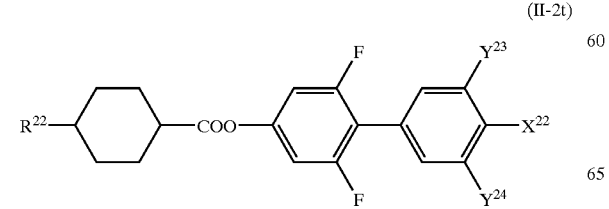
(II-2t)
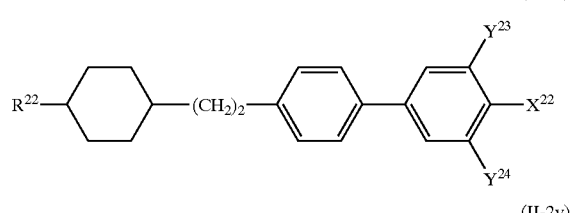
(II-2u)
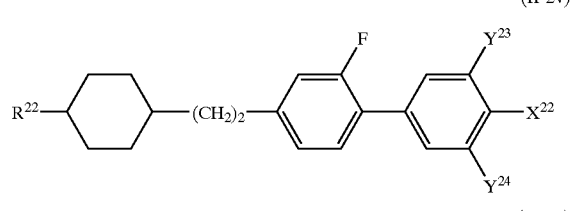
(II-2v)
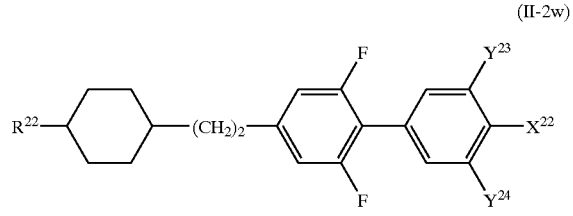
(II-2w)
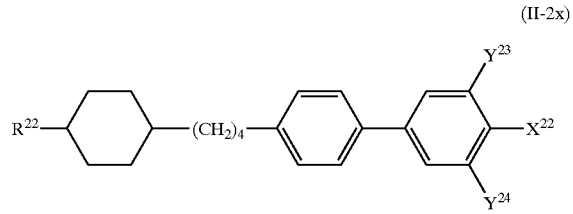
(II-2x)
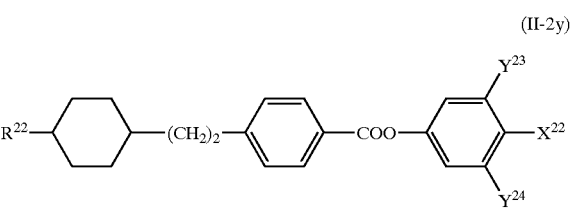
(II-2y)
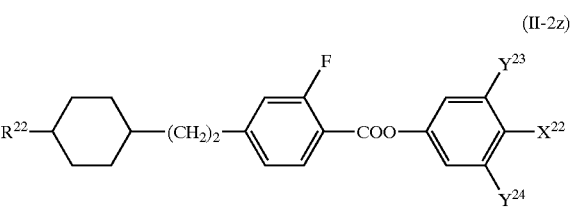
(II-2z)
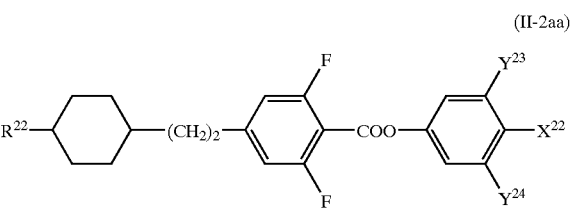
(II-2aa)
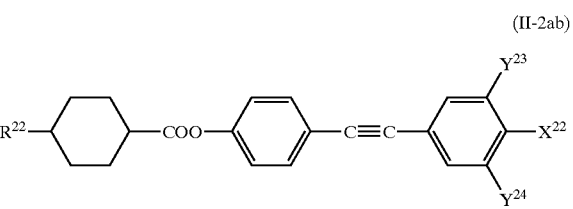
(II-2ab)

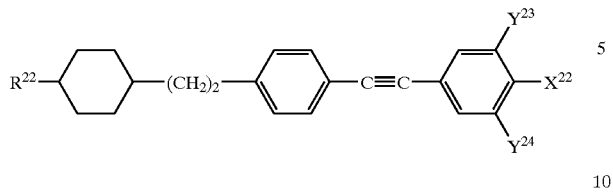
(II-2ac)
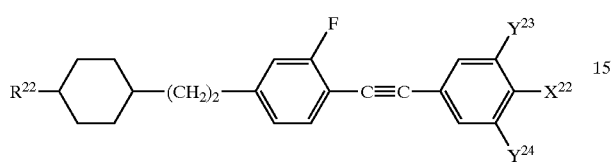
(II-2ad)
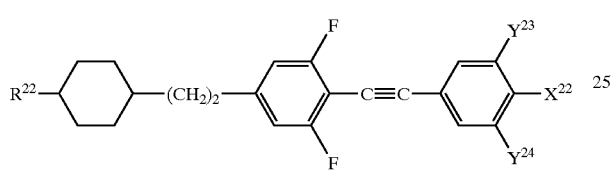
(II-2ae)
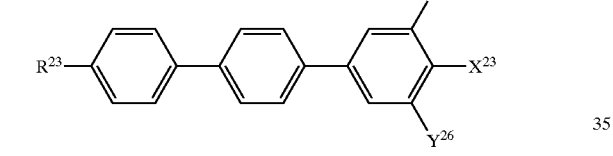
(II-3a)
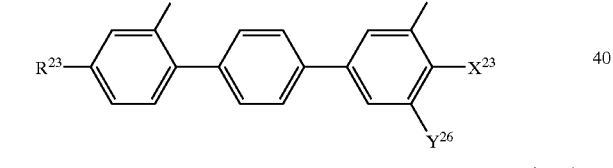
(II-3b)
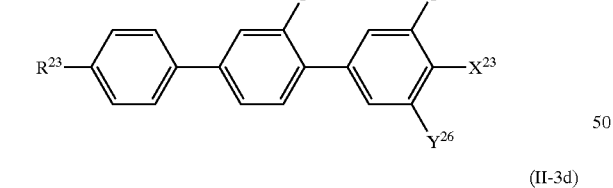
(II-3c)
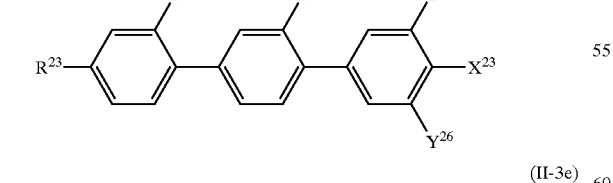
(II-3d)
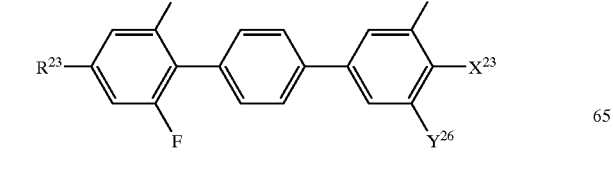
(II-3e)
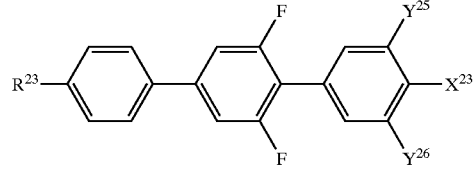
(II-3f)
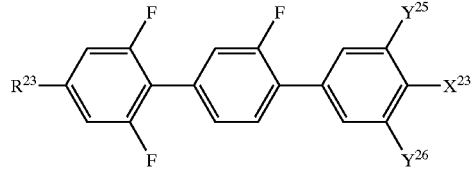
(II-3g)
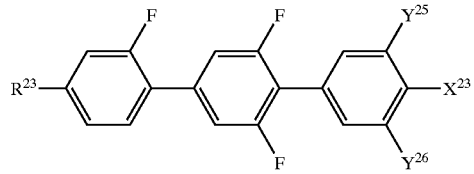
(II-3h)
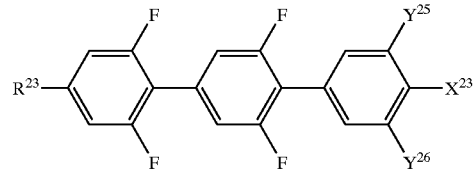
(II-3i)
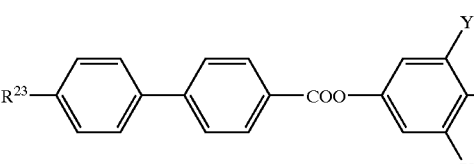
(II-3j)
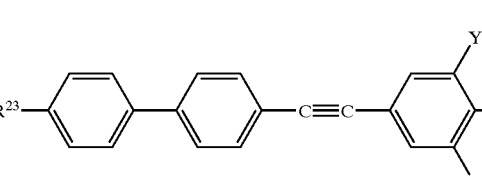
(II-3k)
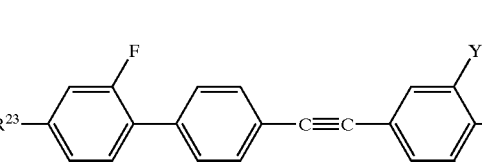
(II-3l)
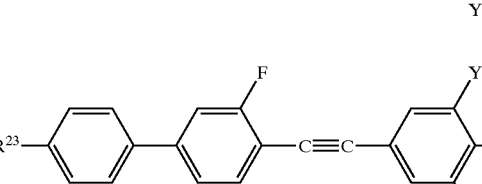
(II-3m)

(II-3n) 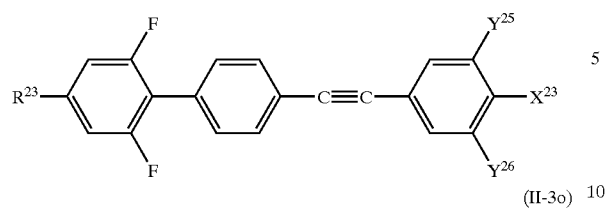
(II-3o) 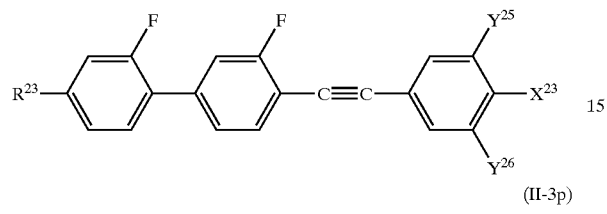
(II-3p) 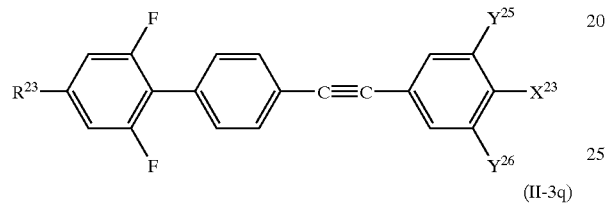
(II-3q) 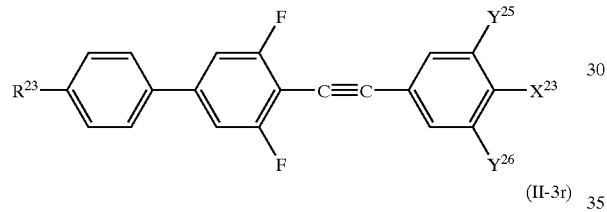
(II-3r) 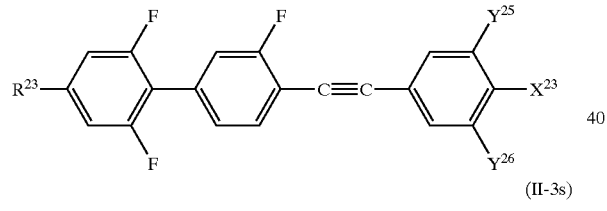
(II-3s) 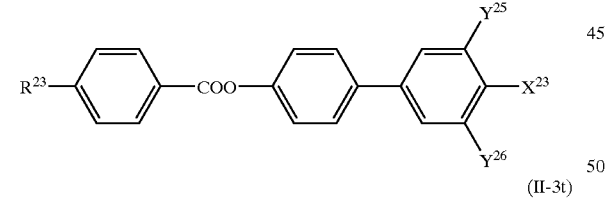
(II-3u) 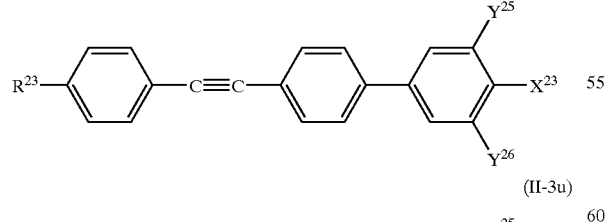
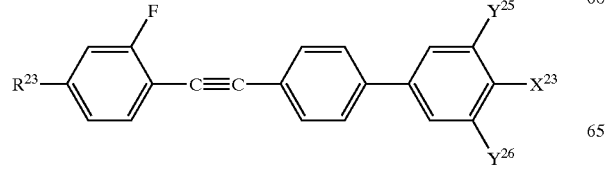
(II-3v) 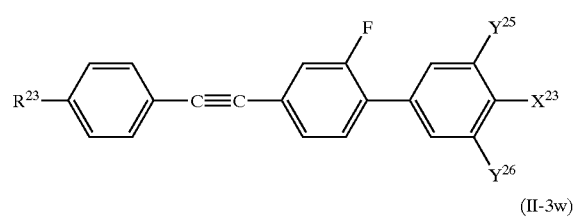
(II-3w) 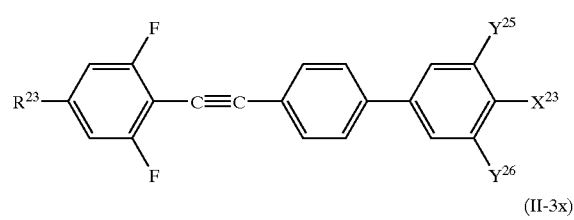
(II-3x) 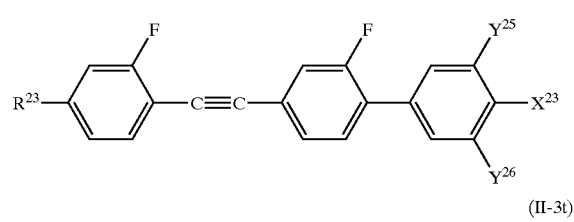
(II-3t) 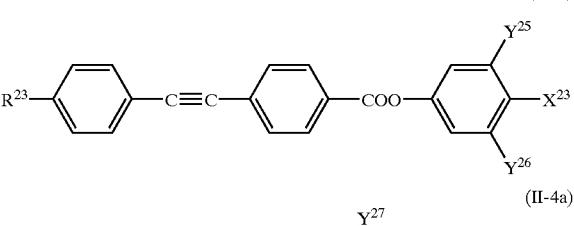
(II-4a) 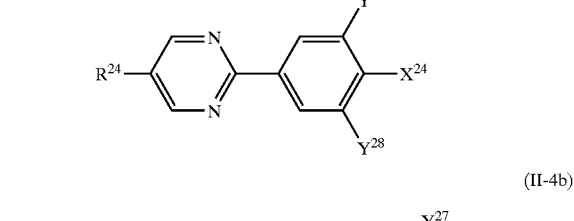
(II-4b) 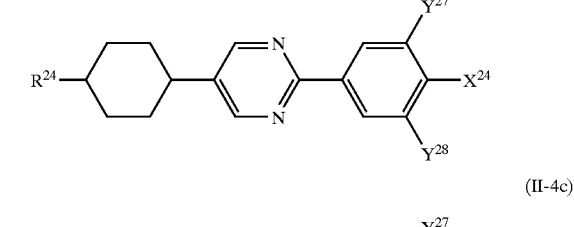
(II-4c) 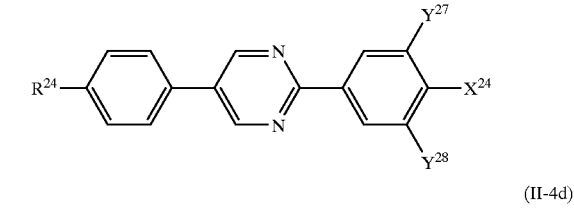
(II-4d) 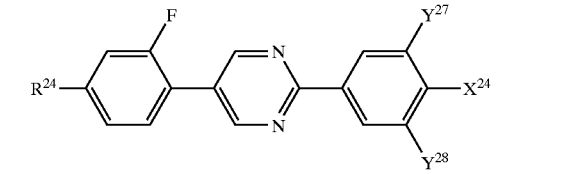

-continued

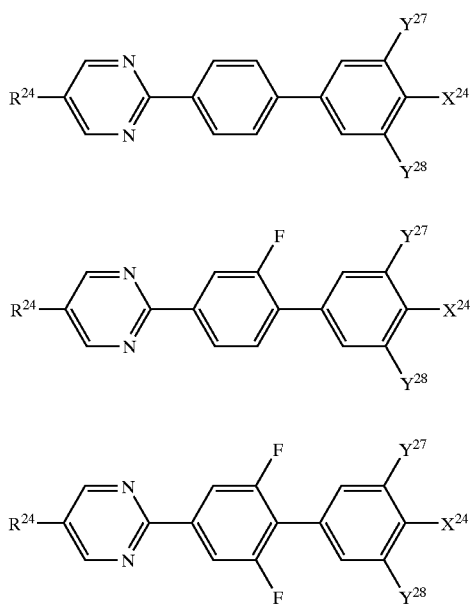

(II-4e)

(II-4f)

(II-4g)

Also, more preferred modes of the formulae (II-51) to (II-54) in the side chain groups $R^{21}$ to $R^{24}$ are compounds represented by the following general formulae (II-5a) to (II-5bc).

| (II-51) $R^{21}$— | (II-52) $R^{22}$— | (II-53) $R^{23}$— | (II-54) $R^{24}$— |
|---|---|---|---|
| (II-5a) | $C_2H_5$— | | |
| (II-5b) | $C_3H_7$— | | |
| (II-5c) | $C_4H_9$— | | |
| (II-5d) | $C_5H_{11}$— | | |
| (II-5e) | $C_6H_{13}$— | | |
| (II-5f) | $C_7H_{15}$— | | |
| (II-5g) | $C_2H_5O$— | | |
| (II-5h) | $C_3H_7O$— | | |
| (II-5i) | $C_4H_9O$— | | |
| (II-5j) | $C_5H_{11}O$— | | |
| (II-5k) | $C_6H_{13}O$— | | |
| (II-5l) | $C_7H_{15}O$— | | |
| (II-5m) | $C_2H_5COO$— | | |
| (II-5n) | $C_3H_7COO$— | | |
| (II-5o) | $C_4H_9COO$— | | |
| (II-5p) | $C_5H_{11}COO$— | | |
| (II-5q) | $C_6H_{13}COO$— | | |
| (II-5r) | $C_7H_{15}COO$— | | |
| (II-5s) | $CH_3OCH_2$— | | |
| (II-5t) | $CH_3OC_2H_4$— | | |
| (II-5u) | $CH_3OC_3H_6$— | | |
| (II-5v) | $CH_3OC_4H_8$— | | |
| (II-5w) | $CH_3OC_5H_{10}$— | | |
| (II-5x) | $C_2H_5OCH_2$— | | |
| (II-5y) | $C_2H_5OC_2H_4$— | | |
| (II-5z) | $C_2H_5OC_3H_6$— | | |
| (II-5aa) | $C_2H_5OC_4H_8$— | | |
| (II-5ab) | $C_2H_5OC_5H_{10}$— | | |
| (II-5ac) | $C_3H_7OCH_2$— | | |
| (II-5ad) | $C_3H_7OC_2H_4$— | | |
| (II-5ae) | $C_3H_7OC_3H_6$— | | |
| (II-5af) | $C_3H_7OC_4H_8$— | | |
| (II-5ag) | $C_3H_7OC_5H_{10}$— | | |
| (II-5ah) | $CH_2$=CH— | | |
| (II-5ai) | $CH_3CH$=CH— | | |
| (II-5aj) | $C_2H_5CH$=CH— | | |
| (II-5ak) | $C_3H_7CH$=CH— | | |
| (II-5al) | $CH_2$=$CHC_2H_4$— | | |
| (II-5am) | $CH_3CH_2$=$CHC_2H_4$— | | |
| (II-5an) | $CH_2$=$CHC_2H_5CH$=CH— | | |
| (II-5ao) | $CH_2$=CHO— | | |
| (II-5ap) | $CH_3CH$=CHO— | | |
| (II-5aq) | $C_2H_5CH$=CHO— | | |
| (II-5ar) | $C_3H_7CH$=CHO— | | |
| (II-5as) | $CH_2$=$CHC_2H_4O$— | | |
| (II-5at) | $CH_3CH_2$=$CHC_2H_4O$— | | |
| (II-5au) | $CH_2$=$CHC_2H_5CH$=CHO— | | |
| (II-5av) | CHF=CH— | | |
| (II-5aw) | $CH_2$=CF— | | |
| (II-5ax) | $CF_2$=CH— | | |
| (II-5ay) | CHF=CF— | | |
| (II-5az) | CHF=$CHC_2H_4$— | | |
| (II-5ba) | $CH_2$=$CFC_2H_4$— | | |
| (II-5bb) | $CF_2$=$CHC_2H_4$— | | |
| (II-5bc) | CHF=$CFC_2H_4$— | | |

Also, more preferred modes of the partial structural formulae (II-61) to (II-64) of 1,4-phenylene having a polar group are compounds represented by the following general formulae (II-6a) to (II-6r).

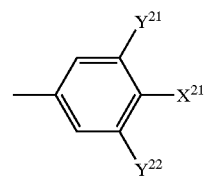

(II-61)

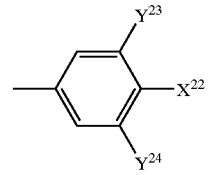

(II-62)

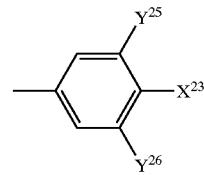

(II-63)

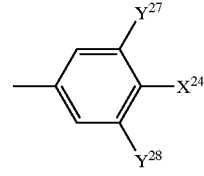

(II-64)

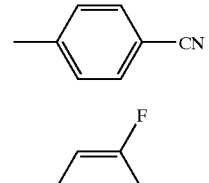

(II-6a)

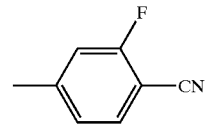

(II-6b)

(II-6c) 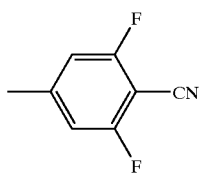

(II-6d) 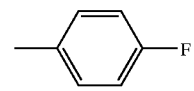

(II-6e) 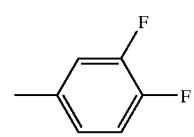

(II-6f) 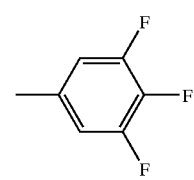

(II-6g) 

(II-6h) 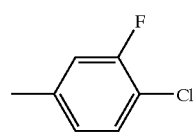

(II-6i) 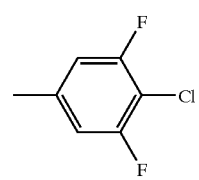

(II-6j) 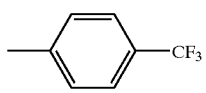

(II-6k) 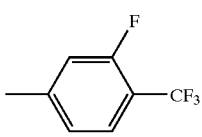

(II-6l) 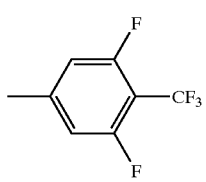

(II-6m) 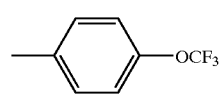

(II-6n) 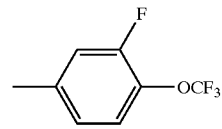

(II-6o) 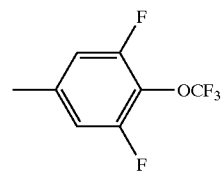

(II-6p) 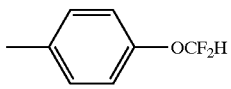

(II-6q) 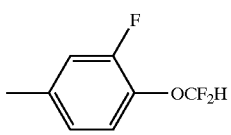

(II-6r) 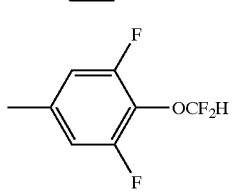

In this connection, each of the compounds used in the following was thoroughly purified by removing impurities using distillation, column purification, recrystallization and the like techniques.

In describing further in detail, when a general purpose liquid crystal composition is desired, it is desirable to use the following compounds in the liquid crystal component B, and the effects of the present invention can be obtained by the combination of such a liquid crystal component B with the liquid crystal component A.

Among compounds of the aforementioned general formulae (II-1) to (II-4), (II-ai) compounds in which $R^{21}$ to $R^{24}$ are alkenyl groups having 2 to 5 carbon atoms, illustratively, compounds in which they have the basic structures of the general formulae (II-1a) to (II-4g), side chain groups of (II-5ah) to (II-5bc) and polar group partial structures of general formulae (II-6a) to (II-6r), more preferably compounds having the basic structures of general formulae (II-1a) to (II-11) or (II-2i) to (II-2ae), can provide further improved electro-optical characteristics of STN-LCD, TFT-LCD, PDLC, PN-LCD and the like devices, and (II-aii): compounds in which $X^{21}$ to $X^{24}$ are F, Cl or —$OCF_3$, illustratively, compounds in which they have the basic structures of the general formulae (II-1a) to (II-4g), side chain groups of (II-5ah) to (II-5bc) and polar group partial structures of general formulae (II-6d) to (II-6i) or (II-6m) to (II-6o), more preferably compounds having the basic structures of general formulae (II-1a) to (II-11), (II-2f) to (II-2q), (II-2u) to (II-2w) or (II-2ab) to (II-4f) and polar group partial structures of general formulae (II-6d) to (II-6i) or (II-6m) to (II-6o), can provide TFT-LCD, PDLC, PN-LCD and the like devices for active use with reduced driving voltage and excellent high voltage holding ratio when these compounds are substantially used as the main component and also can provide TN-LCD, STN-LCD, PDLC, PN-LCD and the like devices with excellent driving voltage, sharpness and response or their temperature characteristics when compounds in which $X^{21}$ to $X^{24}$ are F and CN are jointly used substantially as the main component.

Among compounds of the aforementioned general formula (II-1), (II-aiii): compounds in which $Z^{22}$ is —(CH$_2$)$_2$— or —(CH$_2$)$_4$—, illustratively, compounds having basic structures of the general formulae (II-1c), (II-1d), (II-1g) and (II-1h), side chain groups of (II-5a) to (II-5bc) and polar group partial structures of general formulae (II-6a) to (II-6r), or (II-aiv): compounds in which $k^{21}$ is 1, illustratively, compounds having basic structures of the general formulae (II-1e) to (II-1l), side chain groups of (II-5a) to (II-5bc) and polar group partial structures of general formulae (II-6a) to (II-6r), are suitable for use in a case which requires low driving voltage and relatively small birefringence.

Among compounds of the aforementioned general formula (II-2), (II-av): compounds in which at least one of $Y^{23}$, $Y^{24}$, $W^{21}$ and $W^{22}$ is F, illustratively, compounds having basic structures of general formulae (II-2a), (II-2c), (II-2f), (II-2i), (II-2l), (II-2o), (II-2r), (II-2u), (II-2x), (II-2y), (II-2ab) and (II-2ac), side chain groups of (II-5a) to (II-5bc) and polar group partial structures of general formulae (II-6b), (II-6c), (II-6e), (II-6f), (II-6h), (II-6i), (II-6k), (II-6l), (II-6n), (II-6o), (II-6q) and (II-6r), or compounds having basic structures of general formulae (II-2b), (11-2d), (II-2e), (II-2g), (II-2h), (II-2j), (II-2k), (II-2m), (II-2n), (II-2p), (II-2q), (II-2s), (II-2t), (II-2v), (II-2w), (II-2z), (II-2aa), (II-2ad) and (II-2ae), side chain groups of (II-5a) to (II-5bc) and polar group partial structures of general formulae (II-6a) to (II-6r), are suitable for reducing driving voltage, (II-avi): compounds in which $k^{22}$ is 1 and $Z^{24}$ is —C≡C—, illustratively, compounds having basic structures of general formulae (II-2o) to (II-2q) and (II-2ab) to (II-2ae), side chain groups of (II-5a) to (II-5bc) and polar group partial structures of general formulae (II-6a) to (II-6r), are suitable for a case which requires low driving voltage and relatively large birefringence, and (II-avii): compounds in which $Z^{23}$ is a single bond or —(CH$_2$)$_2$— and $Z^{24}$ is —COO—, illustratively, compounds having basic structures of general formulae (II-2l) to (II-2n), (II-2r) to (II-2t) and (II-2y) to (II-2aa), side chain groups of (II-5a) to (II-5bc) and polar group partial structures of general formulae (II-6a) to (II-6r), are suitable for use in a case which requires low driving voltage.

Among compounds of the aforementioned general formula (II-3), (II-aviii): compounds in which at least one of $Y^{25}$, $Y^{26}$, $W^{23}$ to $W^{26}$ is F, illustratively, compounds having basic structures of general formulae (II-3a), (II-3j), (II-3k), (II-3s) and (II-3t), side chain groups of (II-5a) to (II-5bc) and polar group partial structures of general formulae (II-6b), (II-6c), (II-6e), (II-6f), (II-6h), (II-6i), (II-6k), (II-6l), (II-6n), (II-6o), (II-6q) and (II-6r), or compounds having basic structures of general formulae (II-3b) to (II-3i), (II-3l) to (II-3r) and (II-3u) to (II-3x), side chain groups of (II-5a) to (II-5bc) and polar group partial structures of general formulae (II-6a) to (II-6r), are suitable for reducing driving voltage, (II-aix): compounds in which $Z^{26}$ is —C≡C—, illustratively, compounds having basic structures of general formulae (II-3k) to (II-3r), side chain groups of (II-5a) to (II-5bc) and polar group partial structures of general formulae (II-6a) to (II-6r), are suitable for a case which requires low driving voltage and relatively large birefringence, and (II-ax): compounds in which $Z^{25}$ is a single bond or —C≡C— and $Z^{26}$ is —COO—, illustratively, compounds having basic structures of general formulae (II-3j) and (II-3y), side chain groups of (II-5a) to (II-5bc) and polar group partial structures of general formulae (II-6a) to (II-6r).

(II-axi): Compounds represented by the aforementioned general formula (II-4), illustratively, compounds having basic structures of general formulae (II-4a) to (II-4g), side chain groups of (II-5a) to (II-5bc) and polar group partial structures of general formulae (II-6a) to (II-6r).

Among compounds of the aforementioned general formulae (II-1) and (II-2), (II-axii): the rings $A^{21}$ to $A^{24}$ are trans-1,4-cyclohexylene, and hydrogen atoms of the rings are replaced by deuterium atoms, illustratively, compounds having basic structures of general formulae (II-1a) to (II-1l) and (II-2i) to (II-2ae), side chain groups of (II-5a) to (II-5bc) and polar group partial structures of general formulae (II-6a) to (II-6r).

A nematic liquid crystal composition which contains one or two or more compounds selected from the compounds represented by these subgroups (II-ai) to (II-axii) is desirable.

Also, when a liquid crystal composition suitable for use in TN-LCD or STN-LCD is desired, it is desirable to use the following compounds in the liquid crystal component B, and the effects of the present invention can be obtained by the combination of such a liquid crystal component B with the liquid crystal component A.

Among compounds represented by the aforementioned general formula (II-1) in which $R^{21}$ is an alkyl or alkenyl group having 2 to 5 carbon atoms, (II-bi): compounds in which $k^{21}$ is 0 and $X^{21}$ is —CN, illustratively, compounds having basic structures of general formulae (II-1a) to (II-1d), side chain groups of (II-5a) to (II-5d), (II-5ah) to (II-5am) and (II-5av) to (II-5bc) and polar group partial structures of general formulae (II-6a) to (II-6r), and (II-bii): compounds in which $k^{21}$ is 1, $X^{21}$ is F or , and $Y^{21}$ and $Y^{22}$ are H or F, illustratively, compounds having basic structures of general formulae (II-1e) to (II-1l), side chain groups of (II-5a) to (II-5d), (II-5ah) to (II-5am) and (II-5av) to (II-5bc) and polar group partial structures of general formulae (II-6a) to (II-6f).

Among compounds represented by the aforementioned general formula (II-2) in which $R^{22}$ is an alkyl or alkenyl group having 2 to 5 carbon atoms, (II-biii): compounds in which $k^{22}$ is 0, $X^{22}$ is —CN, and $Y^{23}$, $Y^{24}$, $W^{21}$ and $W^{22}$ are H or F, illustratively, compounds having basic structures of general formulae (II-2a) to (II-2h), side chain groups of (II-5a) to (II-5d), (II-5ah) to (II-5am) and (II-5av) to (II-5bc) and polar group partial structures of general formulae (II-6a) to (II-6c), and (II-biv): compounds in which $k^{22}$ is 1, $Z^{23}$ is a single bond, —(CH$_2$)$_2$— or —COO—, $Z^{24}$ is a single bond, —COO— or —C≡C—, $X^{22}$ is F or —CN and $Y^{23}$, $Y^{24}$, $W^{21}$ and $W^{22}$ are H or F, illustratively, compounds having basic structures of general formulae (II-2i) and (II-2ae), side chain groups of (II-5a) to (II-5d), (II-5ah) to (II-5am) and (II-5av) to (II-5bc) and polar group partial structures of general formulae (II-6a) to (II-6f).

Among compounds represented by the aforementioned general formula (II-3) in which $R^{23}$ is an alkyl or alkenyl group having 2 to 5 carbon atoms, (II-bv): one of $Z^{25}$ and $Z^{26}$ is a single bond and the other is a single bond, —COO— or —C≡C—, illustratively, compounds having basic structures of general formulae (II-3a) to (II-3x), side chain groups of (II-5a) to (II-5d), (II-5ah) to (II-5am) and (II-5av) to (II-5bc) and polar group partial structures of general formulae (II-6a) to (II-6r), and (II-bvi): compounds in which $Y^{25}$, $Y^{26}$ and $W^{23}$ to $W^{26}$ are H or F, illustratively, compounds having basic structures of general formulae (II-3a) to (II-3x), side chain groups of (II-5a) to (II-5d), (II-5ah) to (II-5am) and (II-5av) to (II-5bc) and polar group partial structures of general formulae (II-6a) to (II-6r).

(II-bvii): Compounds of the aforementioned general formula (II-4) in which $R^{24}$ is an alkyl or alkenyl group having 2 to 7 carbon atoms and $k^{23}+k^{24}$ is 0, illustratively, compounds having the basic structure of general formula (II-4a), side chain groups of (II-5a) to (II-5f), (II-5ah) to (II-5am) and (II-5av) to (II-5bc) and polar group partial structures of general formulae (II-6a) to (II-6r).

(II-bviii): Compounds of the aforementioned general formulae (II-1) and (II-2) in which rings $A^{21}$ to $A^{24}$ are trans-1,4-cyclohexylene and hydrogen atoms of the rings are replaced by deuterium atoms, illustratively, compounds having basic structures of general formulae (II-1a) to (II-1l) and (II-2i) to (II-2ae), side chain groups of (II-5a) to (II-5bc) and polar group partial structures of general formulae (II-6a) to (II-6r).

A nematic liquid crystal composition which contains one or two or more compounds selected from the compounds represented by these subgroups (II-bi) to (II-bviii), wherein the total content of these compounds is from 10 to 100% by weight as the liquid crystal component B, is desirable.

Also, when a liquid crystal composition suitable for use in TFT-LCD, IPS, PDLC, PN-LCD or the like device for active use is desired, it is desirable to use the following compounds in the liquid crystal component B, and the effects of the present invention can be obtained by the combination of such a liquid crystal component B with the liquid crystal component A.

(II-ci): Compounds of the aforementioned general formula (II-1) in which $R^{21}$ is an alkyl or alkenyl group having 2 to 5 carbon atoms, $k^{21}$ is 1, one of $Z^{21}$ and $Z^{22}$ is a single bond and the other is a single bond, —COO—, —(CH$_2$)$_2$— or —(CH$_2$)$_4$—, $X^{21}$ is F, Cl, CF$_3$, OCF$_3$ or OCF$_2$H and at least one of $Y^{21}$ and $Y^{22}$ is F, illustratively, compounds having basic structures of general formulae (II-1e) to (II-1k), side chain groups of (II-5a) to (II-5d), (II-5ah) to (II-5am) and (II-5av) to (II-5bc) and polar group partial structures of general formulae (II-6d) to (II-6r).

(II-cii): Compounds of the aforementioned general formula (II-2) in which $R^{22}$ is an alkyl or alkenyl group having 2 to 5 carbon atoms, $k^{22}$ is 1, $Z^{23}$ is a single bond, —(CH$_2$)$_2$— or —COO—, $Z^{24}$ is a single bond, —COO— or —C≡C—, $X^{22}$ is F, Cl, CF$_3$, OCF$_3$ or OCF$_2$H, at least one of $Y^{23}$ and $Y^{24}$ is F and each of $W^{21}$ and $W^{22}$ is H or F, illustratively, compounds having basic structures of general formulae (II-2i) to (II-2ae), side chain groups of (II-5a) to (II-5d), (II-5ah) to (II-5am) and (II-5av) to (II-5bc) and polar group partial structures of general formulae (II-6d) to (II-6r).

(II-ciii): Compounds of the aforementioned general formula (II-3) in which $R^{23}$ is an alkyl or alkenyl group having 2 to 5 carbon atoms, one of $Z^{25}$ and $Z^{26}$ is a single bond and the other is a single bond, —COO— or —C≡C—, $X^{23}$ is F, at least one of $Y^{25}$ and $Y^{26}$ is F and each of $W^{23}$ to $W^{26}$ is H or at least one of them is F, illustratively, compounds having basic structures of general formulae (II-3a) to (II-3x), side chain groups of (II-5a) to (II-5d), (II-5ah) to (II-5am) and (II-5av) to (II-5bc) and polar group partial structures of general formulae (II-6e) and (II-6f).

(II-civ): Compounds of the aforementioned general formulae (II-1) and (II-2) in which each of the rings $A^{21}$ to $A^{24}$ is trans-1,4-cyclohexylene and hydrogen atoms of these rings are replaced by deuterium atoms, illustratively, compounds having basic structures of general formulae (II-1a) to (II-1l) and (II-2i) to (II-2ae), side chain groups of (II-5a) to (II-5bc) and polar group partial structures of general formulae (II-6a) to (II-6r).

A nematic liquid crystal composition which contains one or two or more compounds selected from the compounds represented by .these subgroups (II-ci) to (II-civ), wherein the total content of these compounds is from 10 to 100% by weight as the liquid crystal component B, is desirable.

Particularly preferred mode in compounds represented by the general formulae (II-1) to (II-4) is a liquid crystal component B which contains the following compounds.

(II-di): Compounds in which each of $R^{21}$ to $R^{24}$ is an alkyl group having 2 to 7 carbon atoms. Compounds in which each of $R^{21}$ and $R^{22}$ is an alkenyl group of CH$_2$=CH—(CH$_2$)$_p$ (p=0 or 2). Illustratively, it is desirable that compounds having basis structures of the general formulae (II-1a), (II-1e), (II-2a), (II-2c), (II-2d), (II-2i), (II-2l), (II-2o), (II-3a), (II-3l), (II-4a) to (II-4c) and (II-4e) have these groups, because viscosity and viscoelasticity can be reduced by adding at least one of such compounds having alkyl and/or alkenyl groups to the liquid crystal component B.

(II-dii): It is desirable to include at least one compound selected from compounds in which $X_{21}$ to $X^{24}$ are F, Cl, —OCF$_3$ or —CN.

(II-diii): When quick response is an important object, it is desirable to use compounds of general formulae (II-1a), (II-1e), (II-2a), (II-2c), (II-2d), (II-2i), (II-2l), (II-2o), (II-3a), (II-3l) and (II-4a) in which $X^{21}$ to $X^{24}$ are F, —OCF$_3$ or —CN, frequently in the liquid crystal component B.

(II-div): When more larger birefringence is required, it is desirable to use compounds of general formulae (II-2a) to (II-4d) in which $X^{22}$ to $X^{24}$ are Cl, —OCF$_3$ or —CN, and/or compounds of general formulae (II-2f) to (II-2h), (II-2o) to (II-2q), (II-2ab) to (II-2ae) and (II-3k) to (II-3x) in which each of $Z^{24}$ to $Z^{26}$ is —C≡C—, frequently in the liquid crystal component B.

(II-dv): When more lower driving voltage is required, it is desirable to use compounds of general formulae (II-1a) to (II-4g) in which $X^{21}$ to $X^{24}$ are F, Cl or —CN and $Y^{21}$ to $Y^{24}$ are essentially F frequently in the liquid crystal component B.

(II-dvi): Compounds of general formulae (II-1) and (II-2) in which hydrogen atom in the cyclohexane ring is replaced by deuterium atom can be used but, since such compounds are useful in adjusting elastic constant of the liquid crystal composition and controlling pre-tilt angle corresponding to the orientation film, it is desirable to use at least one or more of the deuterium-replaced compounds.

(II-dvii): Mixing ratio of two-ring compounds of general formulae (II-1), (II-2) and (II-4) in which $k^{21}$ to $k^{24}$ are 0 to compounds of general formulae (II-1) and (II-2) in which $k^2$ and $k^{22}$ are 1, compounds of general formula (II-4) in which $k^{23}+k^{24}$ is 1 and/or three-ring compounds of general formula (II-3) in the liquid crystal component B can be selected optionally within the range of from 0:100 to 100:0, and when more higher nematic phase-isotropic liquid phase transition temperature is required, it is desirable to frequently use compounds of general formulae (II-1) and (II-2) in which $k^{21}$ and $k^{22}$ are 1, compounds of general formula (II-3) and/or compounds of general formula (II-4) in which $k^{23}+k^{24}$ is 1.

A liquid crystal component B which contains these compounds of (II-ai) to (II-dvii) is characterized by its ability to mix thoroughly with the essential component, liquid crystal component A, and particularly useful in controlling driving voltage in response to each purpose and improving its temperature-dependency or improving response property. Particularly, compounds of general formulae (II-1a) to (II-1g), general formulae (II-2a) to (II-2q), general formulae (II-2u) to (II-2x), general formulae (II-2ab) to (II-2ae), general formulae (II-3a) to (II-3d), general formulae (II-3l) to (II-3r) and general formulae (II-4a) to (II-14e) are excellent in at least one of such effects, and these effects can be obtained even by a small content of from 0.1 to 25% by weight based on the total amount of the nematic liquid crystal composition of the present invention.

The aforementioned effects of the liquid crystal component B can also be obtained when the content of a liquid crystal component C, which will be described in the following, is considerably small. In order to obtain particularly low driving voltage, the content of the liquid crystal component C can be set to 10% by weight or less. In that case, it is desirable to reduce viscosity of the liquid crystal component C as low as possible, because the driving voltage hardly increases or increases within a narrow range and improving effect of response time can be obtained efficiently. For example, as a means for achieving this effect by the liquid crystal component B when amount of the liquid crystal component C is small, it is desirable to include in the liquid crystal component B any one of the compounds of general formulae (II-1) to (II-4) in which $X^{21}$ to $X^{24}$ are F, Cl or —$OCF_3$, in which $Y^{21}$ to $Y^{24}$ are F, in which $Z^{24}$ and $Z^{25}$ are —COO— or —C≡C— or in which $k^{11}$ is 1. Particularly preferred are compounds of general formulae (II-1) to (II-4) in which $X^{21}$ to $X^{24}$ are F, Cl —$OCF_3$, or —CN and/or $Y^{21}$ to $Y^{24}$ are F.

In addition to the liquid crystal component A as the essential component, the liquid crystal composition of the present invention may preferably contain 85% by weight at the most of the liquid crystal component C which comprises compounds having a dielectric anisotropy of from −10 to 2. Preferred examples of the liquid crystal compounds having a dielectric anisotropy of from −10 to 2 are as follows. That is, the liquid crystal compound has a rod-shaped chemical structure in which its central part has a core structure having 1 to 4 six-membered rings, six-membered rings positioned at both termini of the central part in major axis direction have terminal groups substituted at positions corresponding to the major axis of the liquid crystal molecule and both of the terminal groups positioned at both termini are non-polar groups such as an alkyl group, an alkoxy group, an alkoxyalkyl group, an alkenyl group, an alkenyloxy group and alkanoyloxy group. The liquid crystal component C is constituted by compounds within the range of preferably from 1 to 20 species, more preferably from 2 to 12 species.

In view of such points, more desirable mode of the basic structures of the compounds represented by general formulae (III-1) to (III-4) is compounds represented by the general formulae (III-1a) to (III-4o) described in the following. As the liquid crystal component C of the present invention, it may contain preferably from 10 to 100% by weight of compounds selected from the compounds represented by the general formulae (III-1) to (III-4). The liquid crystal component C which contains these compounds can be thoroughly mixed with the liquid crystal component A which contains compounds of the general formulae (I-1) to (I-3), is useful in improving nematic phase at a low temperature, can adjust the birefringence to desired level and is excellent in improving sharpness and response of TN-LCD, TFT-LCD, PDLC, PN-LCD and the like devices or temperature characteristics thereof.

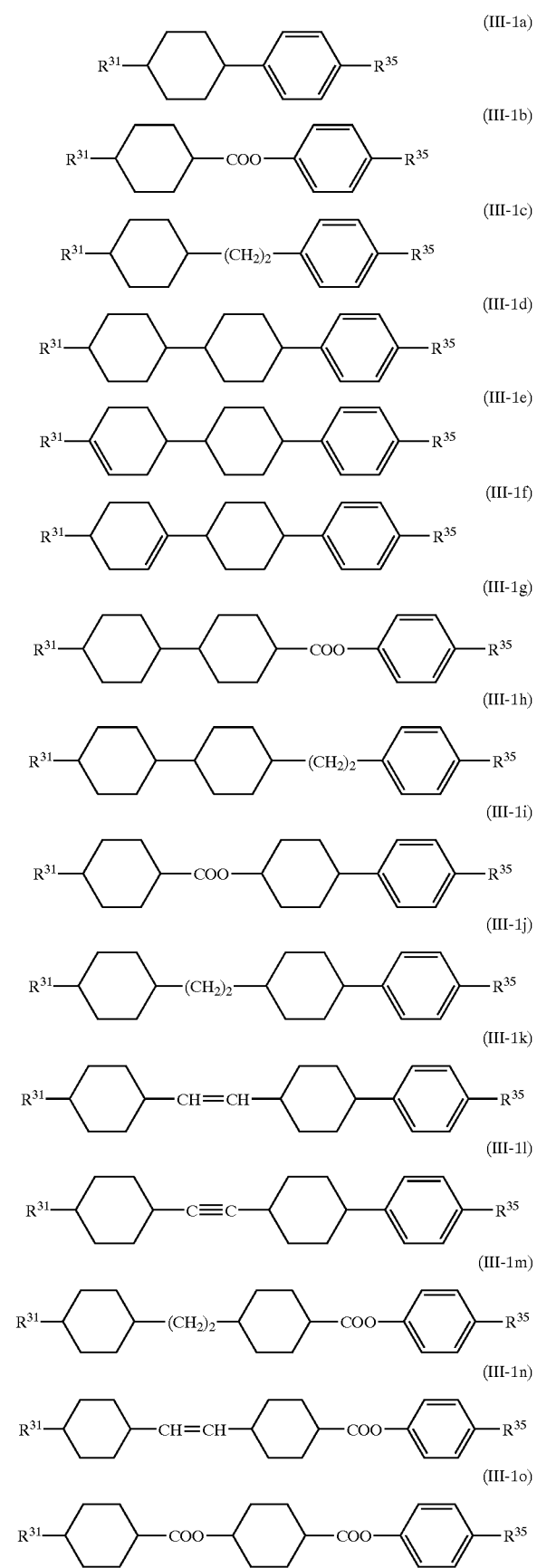

-continued
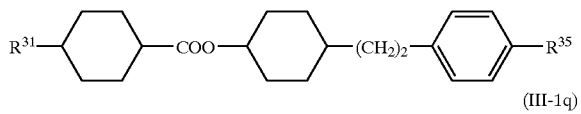 (III-1p)
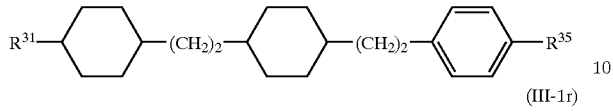 (III-1q)
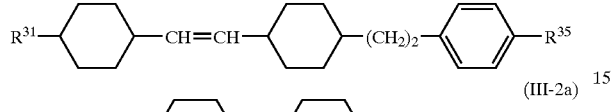 (III-1r)
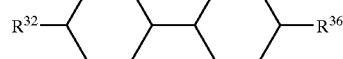 (III-2a)
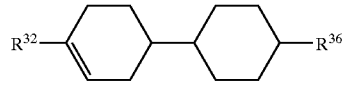 (III-2b)
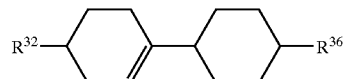 (III-2c)
 (III-2d)
 (III-2e)
 (III-2f)
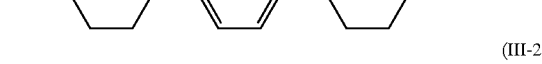 (III-2g)
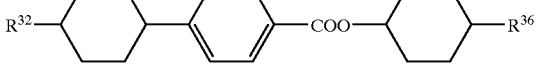 (III-2h)
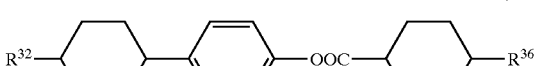 (III-2i)
 (III-2j)
 (III-2k)
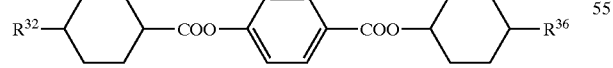 (III-2l)
-continued
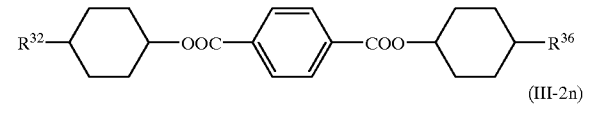 (III-2m)
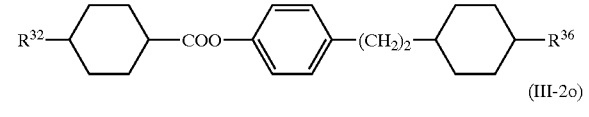 (III-2n)
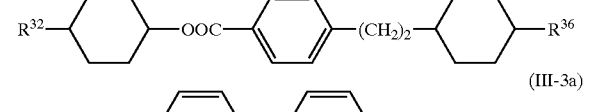 (III-2o)
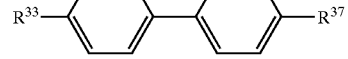 (III-3a)
 (III-3b)
 (III-3c)
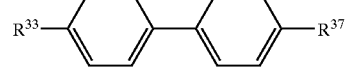 (III-3d)
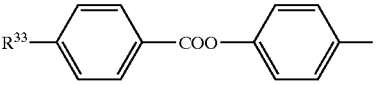 (III-3e)
 (III-3f)
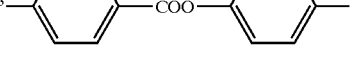 (III-3g)
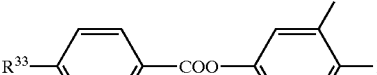 (III-3h)
 (III-3i)
(III-3j)

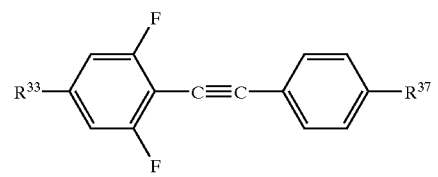
(III-3k)
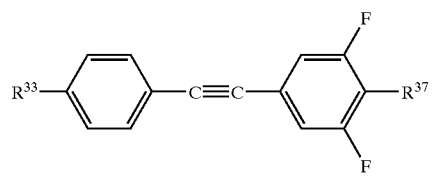
(III-3l)
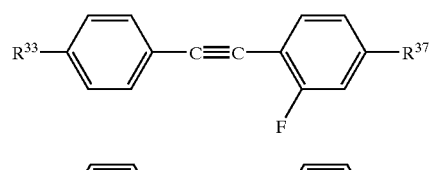
(III-3m)
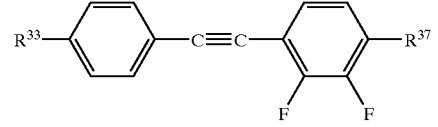
(III-3n)
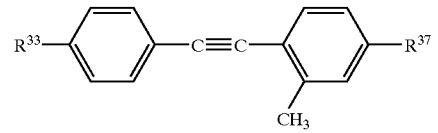
(III-3o)
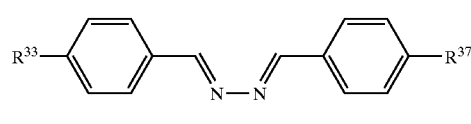
(III-3p)
(III-3q)
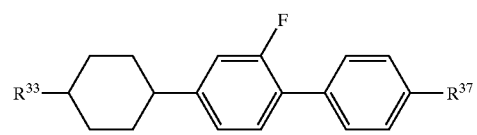
(III-3r)
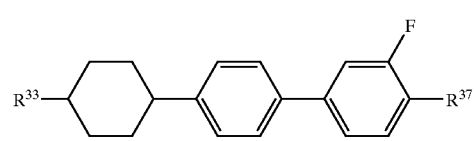
(III-3s)
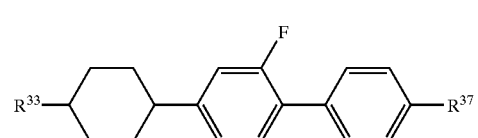
(III-3t)
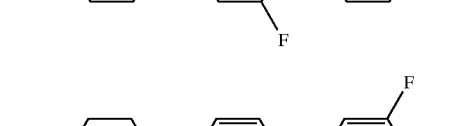
(III-3u)
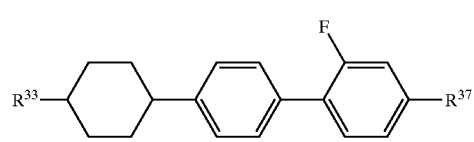
(III-3v)
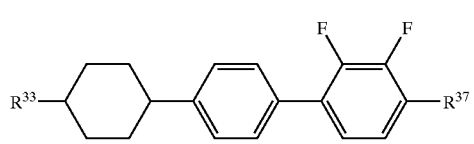
(III-3w)
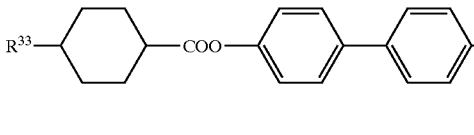
(III-3x)
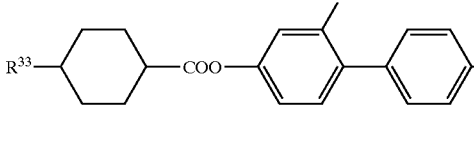
(III-3y)
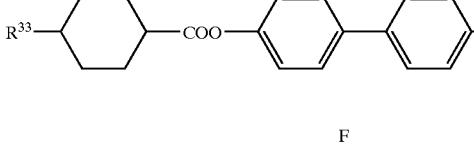
(III-3z)
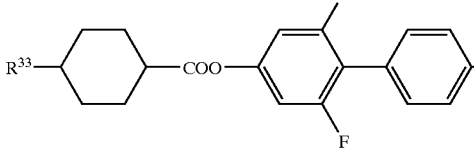
(III-3aa)
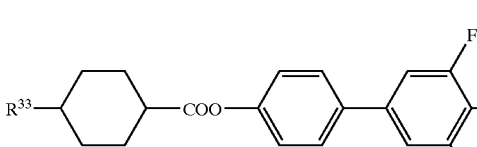
(III-3ab)
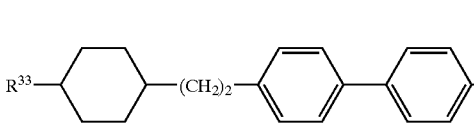
(III-3ac)
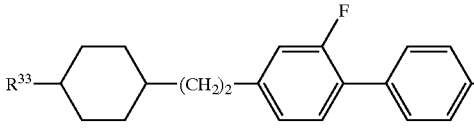
(III-3ad)
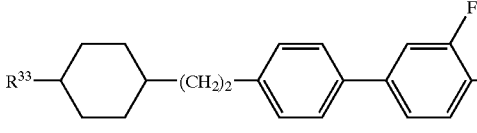
(III-3ae)

(III-3af) 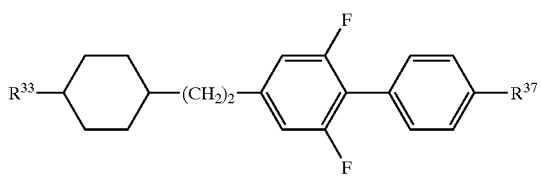
(III-3ao) 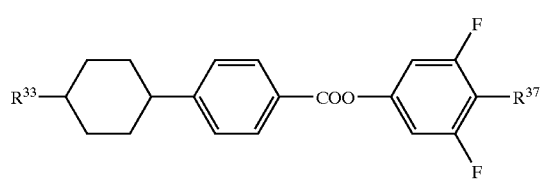
(III-3ag) 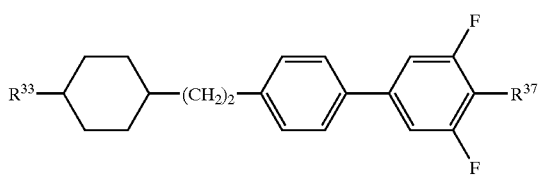
(III-3ap) 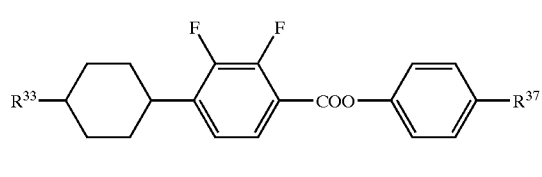
(III-3ah) 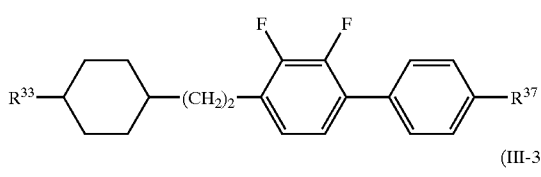
(III-3aq) 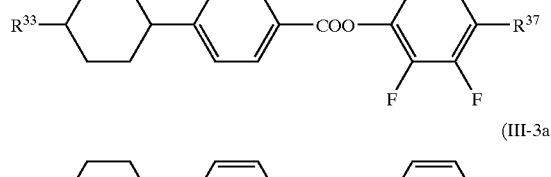
(III-3ai) 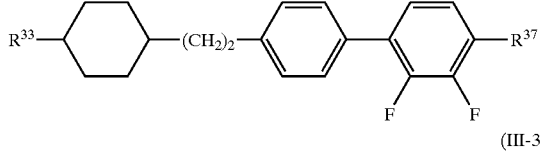
(III-3ar) 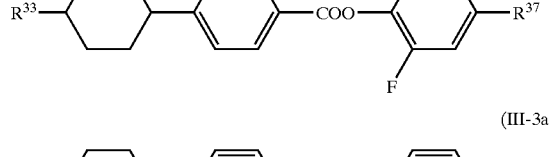
(III-3aj) 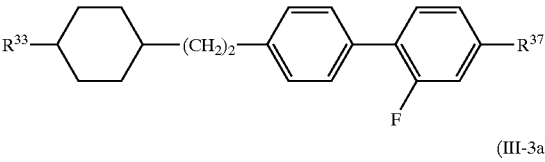
(III-3as) 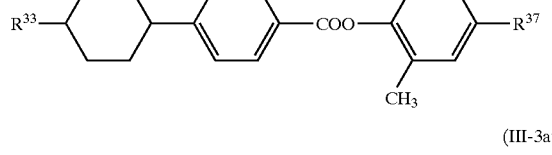
(III-3ak) 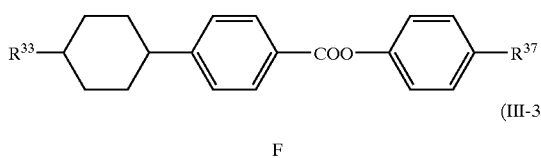
(III-3at) 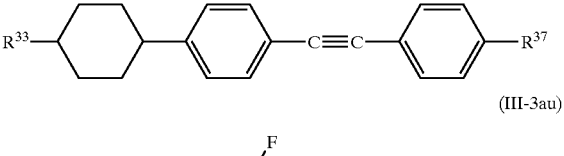
(III-3al) 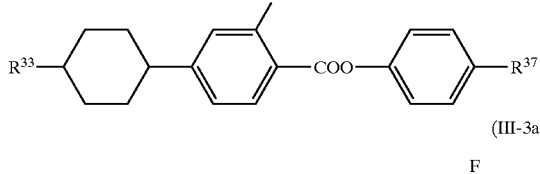
(III-3au) 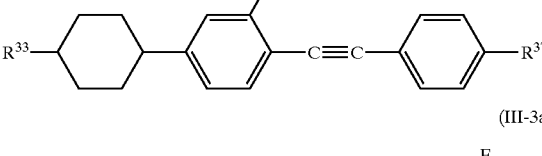
(III-3am) 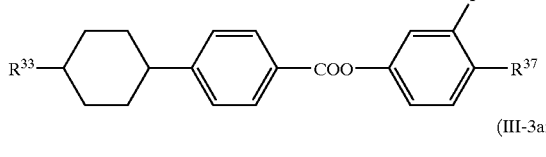
(III-3av) 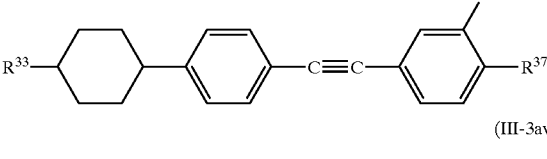
(III-3an) 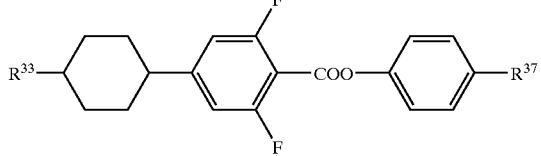
(III-3aw) 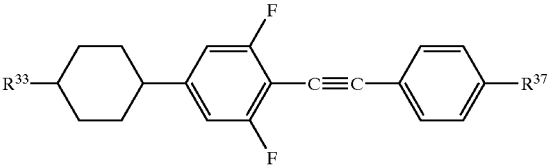

(III-3ax)
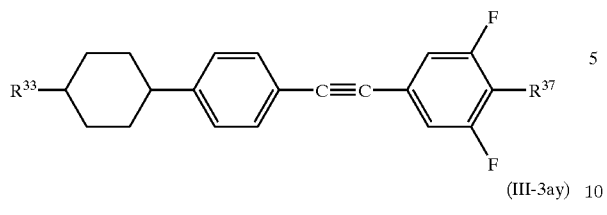
(III-3ay)
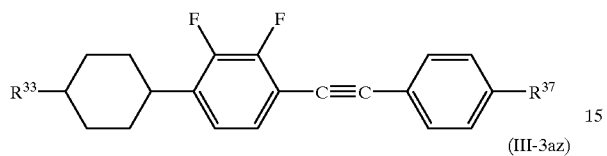
(III-3az)
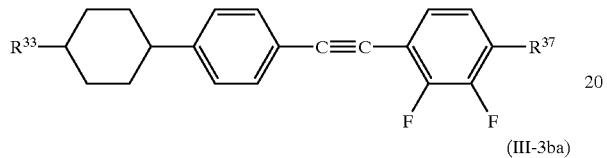
(III-3ba)
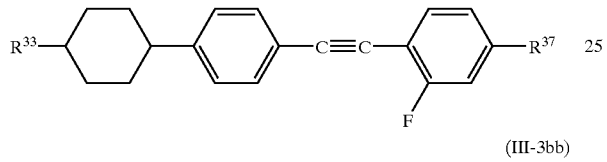
(III-3bb)
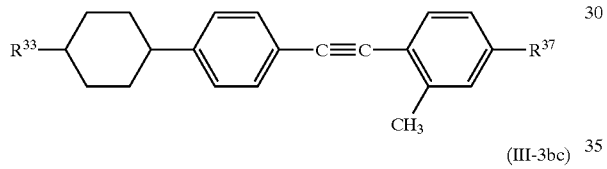
(III-3bc)
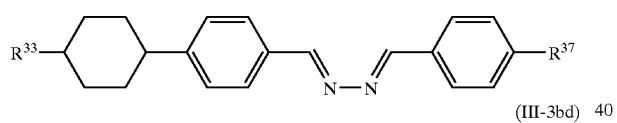
(III-3bd)
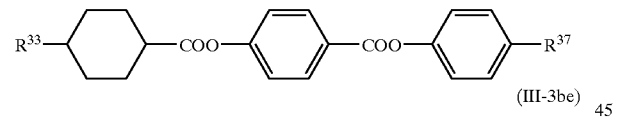
(III-3be)
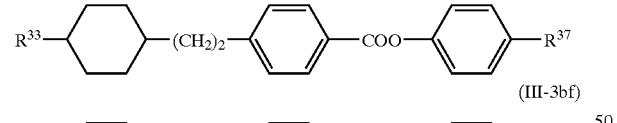
(III-3bf)
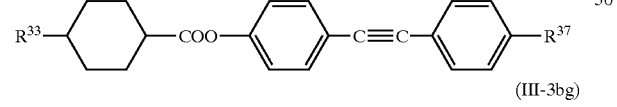
(III-3bg)
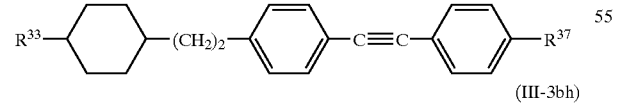
(III-3bh)
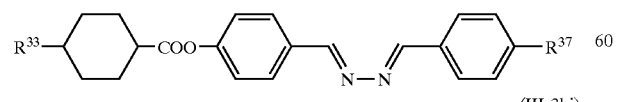
(III-3bi)
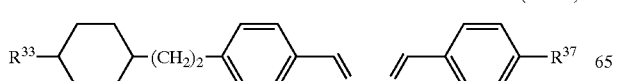
(III-3bj)
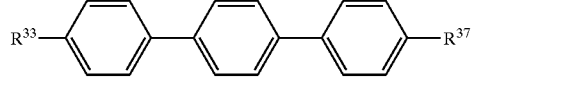
(III-3bk)
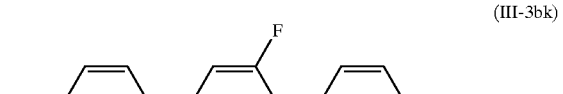
(III-3bl)
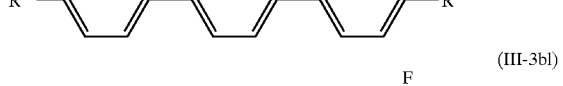
(III-3bm)
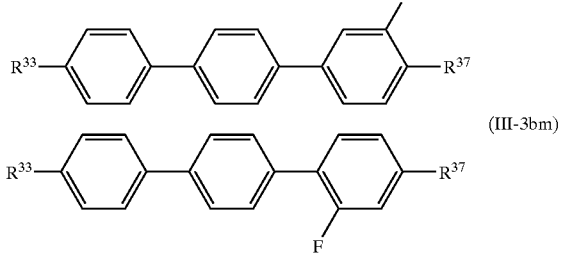
(III-3bn)
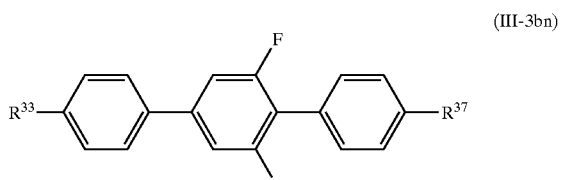
(III-3bo)
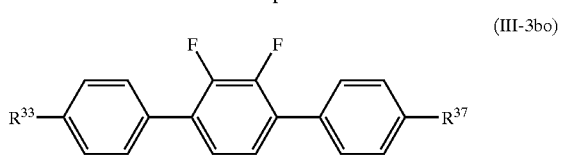
(III-3bp)
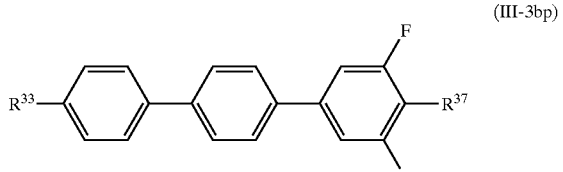
(III-3bq)
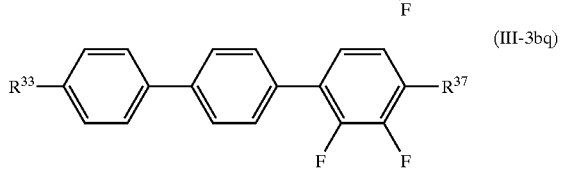
(III-3br)
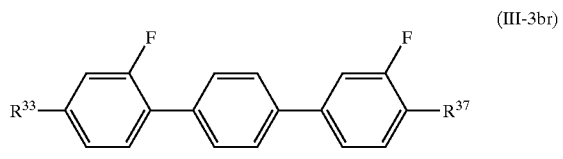
(III-3bs)
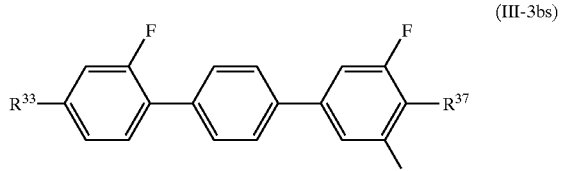
(III-3bt)
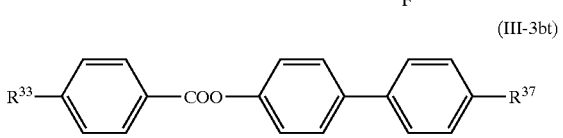

(III-3bu)
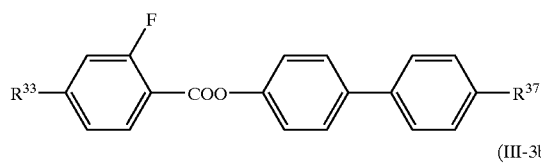
(III-3bv)
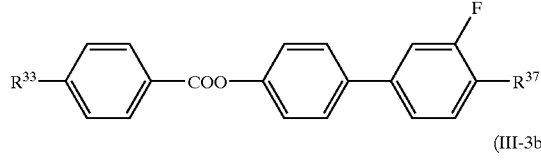
(III-3bw)
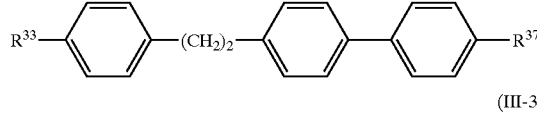
(III-3bx)
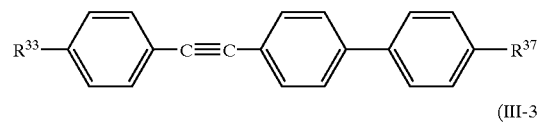
(III-3by)
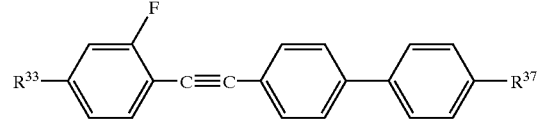
(III-3bz)
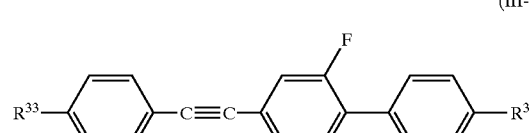
(III-3ca)
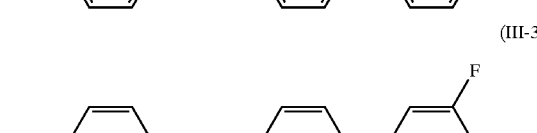
(III-3cb)
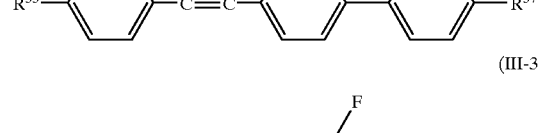
(III-3cc)
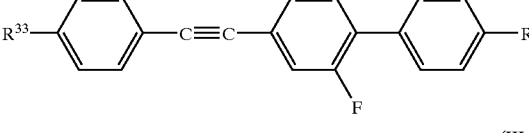
(III-3cd)
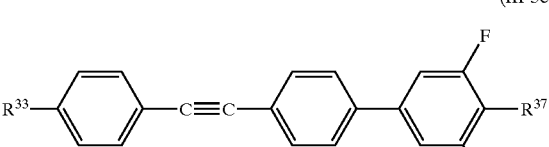
(III-3ce)
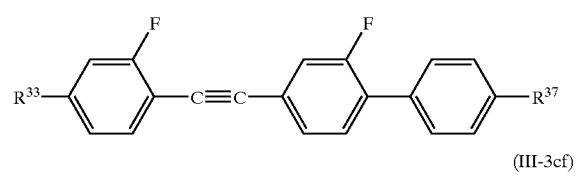
(III-3cf)
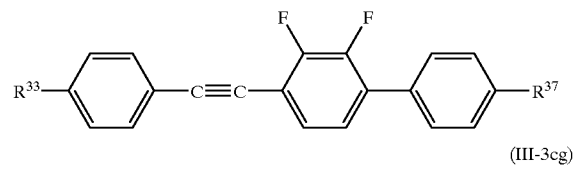
(III-3cg)
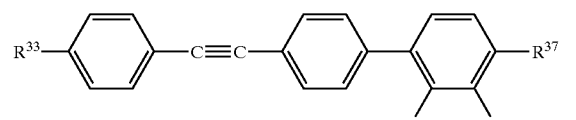
(III-3ch)
(III-3ci)
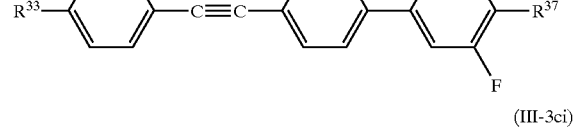
(III-3cj)
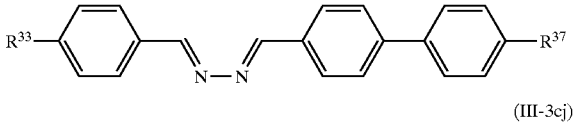
(III-3ck)
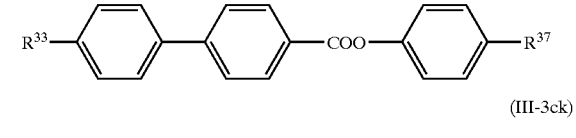
(III-3cl)
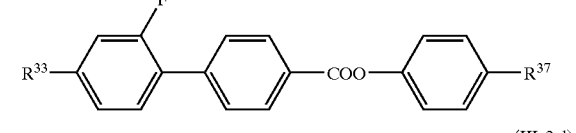
(III-3cm)
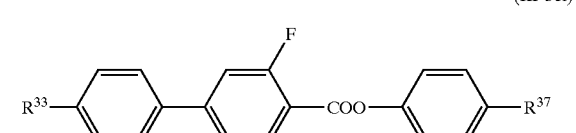
(III-3cn)
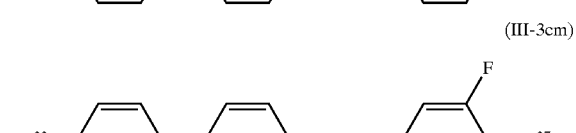

(III-3co)
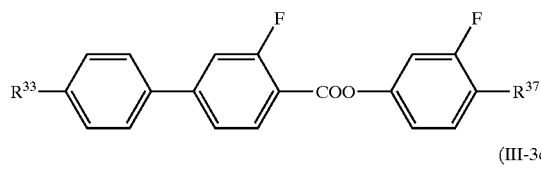
(III-3cp)
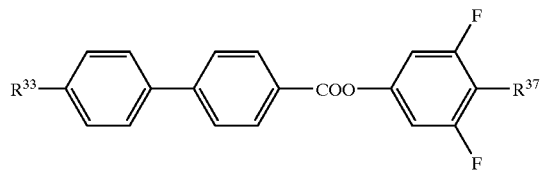
(III-3cq)
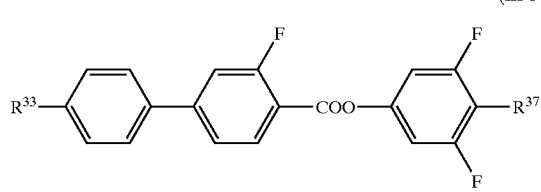
(III-3cr)
(III-3cs)
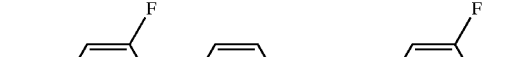
(III-3ct)
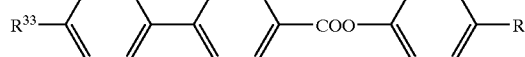
(III-3cu)
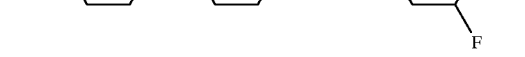
(III-3cv)
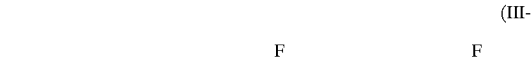
(III-3cw)
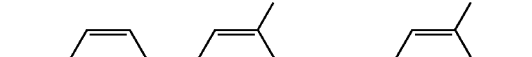
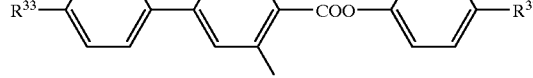
(III-3cx)
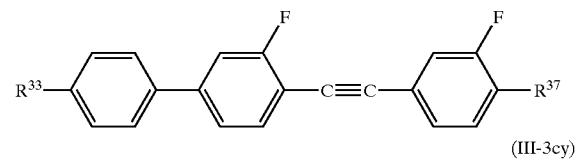
(III-3cy)
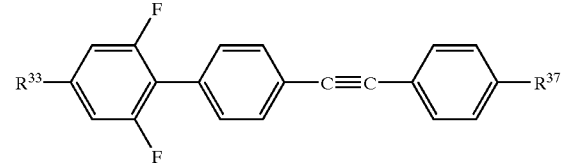
(III-3cz)
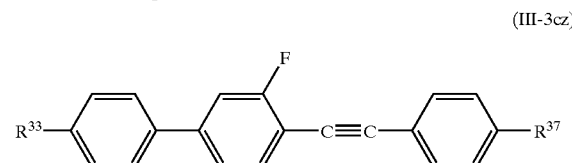
(III-3da)
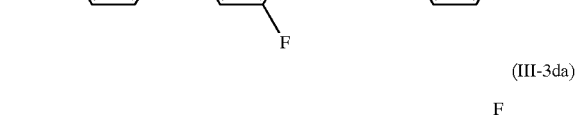
(III-3db)
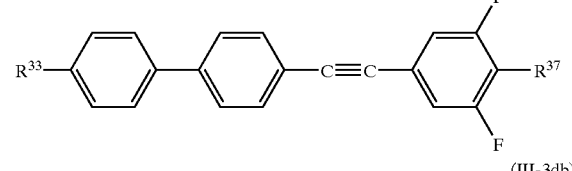
(III-3dc)
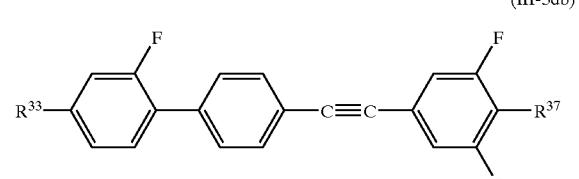
(III-3dd)
(III-3de)
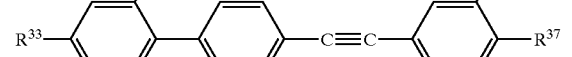
(III-3df)
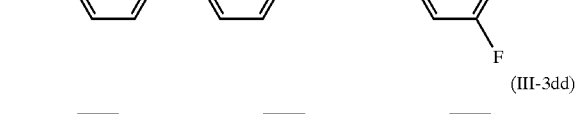
(III-3dg)
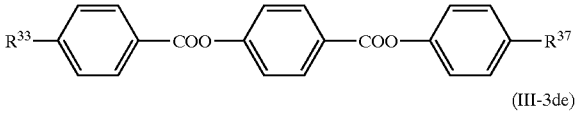
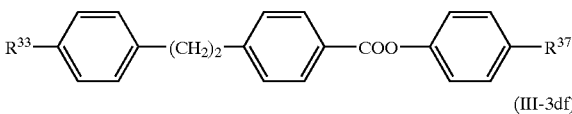
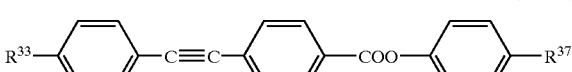
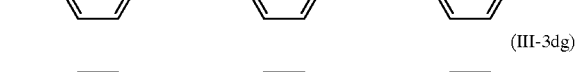

-continued

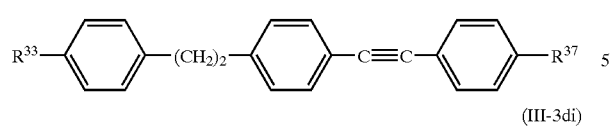
(III-3dh)

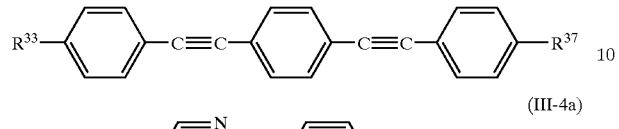
(III-3di)

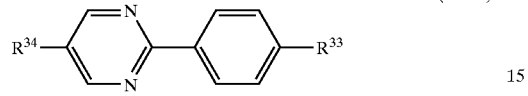
(III-4a)

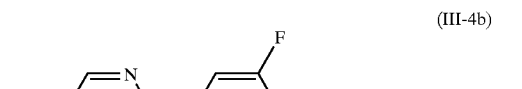
(III-4b)

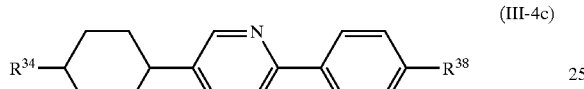
(III-4c)

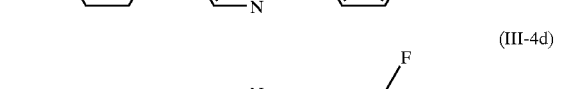
(III-4d)

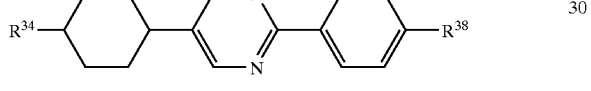
(III-4e)

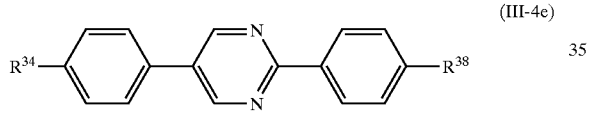
(III-4f)

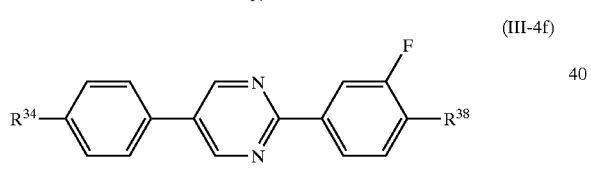
(III-4g)

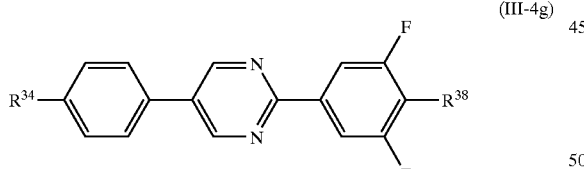
(III-4h)

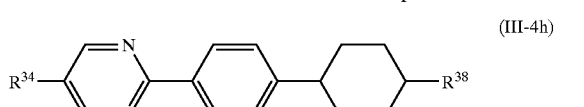
(III-4i)

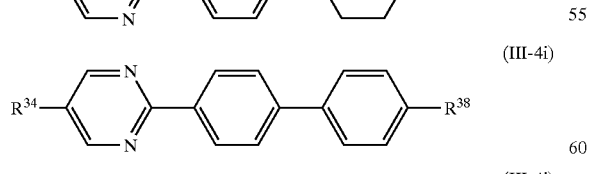
(III-4j)

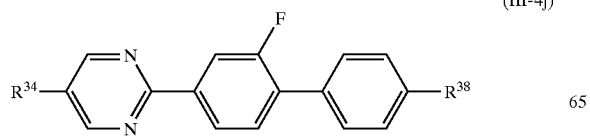

-continued

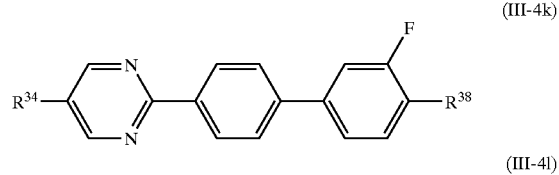
(III-4k)

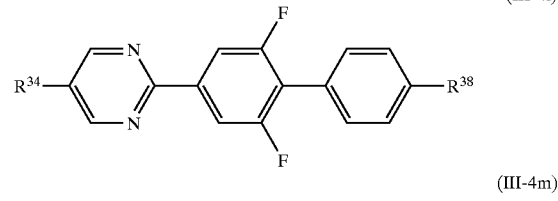
(III-4l)

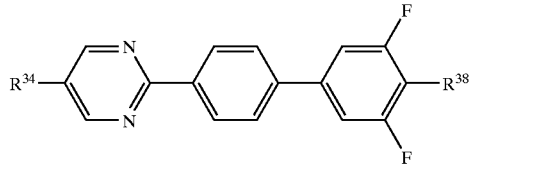
(III-4m)

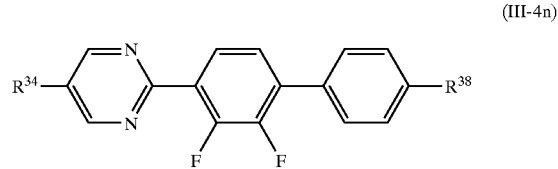
(III-4n)

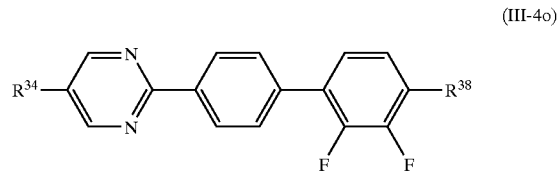
(III-4o)

Also, more preferred mode of the formulae (III-51) to (III-58) of the side chain groups $R^{31}$ to $R^{38}$ is compounds represented by the following general formulae (III-5a) to (III-5bf).

| | | | |
|---|---|---|---|
| (III-51) $R^{31}$— | (III-52) $R^{32}$— | (III-53) $R^{33}$— | (III-54) $R^{34}$— |
| (III-55) $R^{35}$— | (III-56) $R^{36}$— | (III-57) $R^{37}$— | (III-58) $R^{38}$— |

| | |
|---|---|
| (III-5a) | $CH_3$— |
| (III-5b) | $C_2H_5$— |
| (III-5c) | $C_3H_7$— |
| (III-5d) | $C_4H_9$— |
| (III-5e) | $C_5H_{11}$— |
| (III-5f) | $C_6H_{13}$— |
| (III-5g) | $C_7H_{15}$— |
| (III-5h) | $CH_3O$— |
| (III-5i) | $C_2H_5O$— |
| (III-5j) | $C_3H_7O$— |
| (III-5k) | $C_4H_9O$— |
| (III-5l) | $C_5H_{11}O$— |
| (III-5m) | $C_6H_{13}O$— |
| (III-5n) | $C_7H_{15}O$— |
| (III-5o) | $CH_3COO$— |
| (III-5p) | $C_2H_5COO$— |
| (III-5q) | $C_3H_7COO$— |
| (III-5r) | $C_4H_9COO$— |
| (III-5s) | $C_5H_{11}COO$— |
| (III-5t) | $C_6H_{13}COO$— |
| (III-5u) | $C_7H_{15}COO$— |
| (III-5v) | $CH_3OCH_2$— |
| (III-5w) | $CH_3OC_2H_4$— |
| (III-5x) | $CH_3OC_3H_6$— |
| (III-5y) | $CH_3OC_4H_8$— |

-continued

| | |
|---|---|
| (III-5z) | $CH_3OC_5H_{10}-$ |
| (III-5aa) | $C_2H_5OCH_2-$ |
| (III-5ab) | $C_2H_5OC_2H_4-$ |
| (III-5ac) | $C_2H_5OC_3H_6-$ |
| (III-5ad) | $C_2H_5OC_4H_8-$ |
| (III-5ae) | $C_2H_5OC_5H_{10}-$ |
| (III-5af) | $C_3H_7OCH_2-$ |
| (III-5ag) | $C_3H_7OC_2H_4-$ |
| (III-5ah) | $C_3H_7OC_3H_6-$ |
| (III-5ai) | $C_3H_7OC_4H_8-$ |
| (III-5aj) | $C_3H_7OC_5H_{10}-$ |
| (III-5ak) | $CH_2=CH-$ |
| (III-5al) | $CH_3CH=CH-$ |
| (III-5am) | $C_2H_5CH=CH-$ |
| (III-5an) | $C_3H_7CH=CH-$ |
| (III-5ao) | $CH_2=CHC_2H_4-$ |
| (III-5ap) | $CH_3CH_2=CHC_2H_4-$ |
| (III-5aq) | $CH_2=CHC_2H_5CH=CH-$ |
| (III-5ar) | $CH_2=CHO-$ |
| (III-5as) | $CH_3CH=CHO-$ |
| (III-5at) | $C_2H_5CH=CHO-$ |
| (III-5au) | $C_3H_7CH=CHO-$ |
| (III-5av) | $CH_2=CHC_2H_4O-$ |
| (III-5aw) | $CH_3CH_2=CHC_2H_4O-$ |
| (III-5ax) | $CH_2=CHC_2H_5CH=CHO-$ |
| (III-5ay) | $CHF=CH-$ |
| (III-5az) | $CH_2=CF-$ |
| (III-5ba) | $CF_2=CH-$ |
| (III-5bb) | $CHF=CF-$ |
| (III-5bc) | $CHF=CHC_2H_4-$ |
| (III-5bd) | $CH_2=CFC_2H_4-$ |
| (III-5be) | $CF_2=CHC_2H_4-$ |
| (III-5bf) | $CHF=CFC_2H_4-$ |

In this connection, each of the compounds used in the following was thoroughly purified by removing impurities using distillation, column purification, recrystallization and the like techniques.

Though the liquid crystal component C can contain compounds represented by the aforementioned general formulae (III-1) to (III-4), it may be composed of compounds represented by the aforementioned general formulae (III-1), compounds represented by the aforementioned general formulae (III-2), compounds represented by the aforementioned general formulae (III-4) or compounds represented by the aforementioned general formulae (III-3), or these compounds may be used jointly. More preferred is a nematic liquid crystal composition which contains the liquid crystal component C that contains one or two or more compounds selected from the compounds represented by the aforementioned general formulae (III-1) to (III-3), wherein the total content of said compounds is from 10 to 100% by weight.

In describing further in detail, if a general-purpose liquid crystal composition is expected, it is desirable to use the following compounds in the liquid crystal component C, and the effects of the present invention can be obtained when such a type of liquid crystal component C is used in combination with the liquid crystal component A or, if used, the liquid crystal component B.

Among compounds of the aforementioned general formulae (III-1) to (III-4), (III-ai): compounds in which $R^{31}$ to $R^{34}$ are an alkenyl group having 2 to 5 carbon atoms, illustratively, compounds having basic structures of general formulae (III-1a) to (III-4o) in which the side chain groups $R^{35}$ to $R^{38}$ are (III-5a) to (II-5bf) and the side chain groups $R^{31}$ to $R^{34}$ are (III-5ak) to (II-5ap), (III-5ar) to (III-5aw) and (III-5ay) to (III-5bf), by which more improved electro-optical characteristics of STN-LCD, TFT-LCD, PDLC, PN-LCD and the like devices can be obtained through the improvement of response property by reducing viscosity and viscoelasticity and through the improvement of nematic phase-isotropic liquid phase transition temperature, and (III-aii): compounds in which $R^{35}$ to $R^{38}$ are a straight chain alkenyl or alkenyloxy group having 2 to 7 carbon atoms, illustratively, compounds having basic structures of general formulae (III-1a) to (III-4o) in which the side chain groups $R^{31}$ to $R^{34}$ are (III-5a) to (II-5bf) and the side chain groups $R^{35}$ to $R^{38}$ are (III-5ak) to (III-5bf), by which response property can be improved through the reduction of viscosity and viscoelasticity and the nematic phase-isotropic liquid phase transition temperature can be improved, so that more improved electro-optical characteristics of STN-LCD, TFT-LCD, PDLC, PN-LCD and the like devices can be obtained.

Among compounds of the aforementioned general formula (III-1), (III-aiii): compounds in which $k^{31}$ is 0 and $Z^{32}$ is a single bond or $-(CH_2)_2-$, illustratively, compounds having basic structures of general formulae (III-1a) and (III-1c) in which the side chain groups are (III-5a) to (III-5bf), and (III-aiv): compounds in which $k^{31}$ is 1, illustratively, compounds having basic structures of general formulae (III-1d) to (III-1r) in which the side chain groups are (III-5a) to (III-5bf).

(III-av): Compounds represented by the aforementioned general formula (III-2), illustratively, compounds having basic structures of general formulae (III-2a) to (III-2o) in which the side chain groups are (III-5a) to (III-5bf).

Among compounds of the aforementioned general formula (III-3), (III-avi): compounds in which at least one of $Y^{34}$, $Y^{35}$ and $W^{34}$ to $W^{36}$ is F and/or $Y^{33}$ is F or $-CH_3$, illustratively, compounds having basic structures of general formulae (III-3b), (III-3c), (III-3e) to (III-3g), (III-3i) to (III-3o), (III-3r) to (III-3w), (III-3y) to (III-3ab), (III-3ad) to (III-3aj), (III-3al) to (III-3as), (III-3au) to (III-3bb), (III-3bk) to (III-3bs), (III-3bu), (III-3bv), (III-3by) to (III-3ch) and (III-3ck) to (III-3dc) in which the side chain groups are (III-5a) to (III-5bf), (III-avii): compounds in which $k^{33}$ is 0 and $Z^{36}$ is a single bond, illustratively, compounds having basic structures of general formulae (III-3a) to (III-3c) in which the side chain groups are (III-5a) to (III-5bf), (III-aviii): compounds in which $k^{33}$ is 0 and $Z^{35}$ is a single bond, $-OCO-$, $-CH_2O-$, $-OCH_2-$, $-(CH_2)_2-$, $-(CH_2)_4-$, $-CH=CH-(CH_2)_2-$, $-(CH_2)_2CH=CH-$, $-CH=N-$, $-CH=N-N=CH-$, $-N(O)=N-$, $-CH=CH-$ or $-CF=CF-$, illustratively, compounds having basic structures of general formulae (III-3q) to (III-3w), (III-3ac) to (III-3bc), (III-3be), (III-3bg), (III-3bi) to (III-3bs), (III-3bw), (III-3ci) to (III-3dc), (III-3de) and (III-3dh) in which the side chain groups are (III-5a) to (III-5bf), and (III-aix) compounds in which $Z^{35}$ is $-COO-$ or $-C\equiv C-$ and $Z^{36}$ is $-OCO-$, $-CH_2O-$, $-OCH_2-$, $-(CH_2)_2-$, $-(CH_2)_4-$, $-CH=CH-(CH_2)_2-$, $-(CH_2)_2-CH=CH-$, $-CH=N-$, $-CH=N-N=CH-$, $-N(O)=N-$, $-CH=CH-$, $-CF=CF-$ or $-C\equiv C-$, illustratively, compounds having basic structures of general formulae (III-3bf), (III-3bh), (III-3df) and (III-3dg) in which the side chain groups are (III-5a) to (III-5bf).

(III-ax): Compounds represented by the aforementioned general formula (III-4), illustratively, compounds having basic structures of general formulae (III-4a) to (III-4o) in which the side chain groups are (III-5a) to (III-5bf).

(III-axi): Compounds represented by the aforementioned general formulae (III-1) to (III-4) in which rings a to A are trans-1,4-cyclohexylene, and hydrogen atoms in the rings are replaced by deuterium atoms, illustratively, compounds having basic structures of general formulae (III-1a) to (III-2o), (III-3q) to (III-3bi), (III-4c), (III-4d) and (III-4h) in which the side chain groups are (III-5a) to (III-5bf).

A nematic liquid crystal composition which contains one or two or more compounds selected from the compounds represented by these subgroups (III-ai) to (III-axi) is desirable.

Preferred mode of the compounds represented by the general formulae (III-1) to (III-4) is a liquid crystal component C which contains the following compounds.

Among compounds of the aforementioned general formula (III-1) in which $R^{31}$ is an alkyl group having 1 to 5 carbon atoms or an alkenyl group having 2 to 5 carbon atoms and $R^{35}$ is an alkyl or alkoxy group having 1 to 5 carbon atoms or an alkenyl or alkenyloxy group having 2 to 5 carbon atoms, (III-bi): compounds in which $k^{31}$ is 0 and $Z^{32}$ is a single bond, —COO— or —(CH$_2$)$_2$—, illustratively, compounds having basic structures of general formulae (III-1a) to (III-1c) in which the side chain group $R^{31}$ is compounds of (III-5a) to (III-5e) and (III-5ak) to (III-5ap) and the side chain group $R^{35}$ is compounds of (III-5a) to (III-5e), (III-5g) to (III-5l), (III-5ak) to (III-5ap), (III-5ar) to (III-5aw) and (III-5ay) to (III-5bf), and (III-bii): compounds in which $k^{31}$ is 1, the ring $A^{31}$ is trans-1,4-cyclohexylene and one of $Z^{31}$ and $Z^{32}$ is a single bond and the other is a single bond, —COO— or —(CH$_2$)$_2$—, illustratively, compounds having basic structures of general formulae (III-1d) and (III-1g) to (III-1j) in which the side chain group $R^{31}$ is compounds of (III-5a) to (III-5e) and (III-5ak) to (III-5ap) and the side chain group $R^{35}$ is compounds of (III-5a) to (III-5e), (III-5g) to (III-5l), (III-5ak) to (III-5ap), (III-5ar) to (III-5aw) and (III-5ay) to (III-5bf).

Among compounds of the aforementioned general formula (III-2) in which $R^{32}$ is an alkyl group having 1 to 5 carbon atoms or an alkenyl group having 2 to 5 carbon atoms, $R^{35}$ is an alkyl or alkoxy group having 1 to 5 carbon atoms or an alkenyl or alkenyloxy group having 2 to 5 carbon atoms and the ring $A^{32}$ is trans-1,4-cyclohexylene or trans-1,4-cyclohexenylene, (III-biii): compounds in which $k^{32}$ is 0 and $Z^{33}$ is a single bond, —COO— or —(CH$_2$)$_2$—, illustratively, compounds having basic structures of general formulae (III-2a), (III-2d) and (III-2e) in which the side chain group $R^{32}$ is compounds of (III-5a) to (III-5e) and (III-5ak) to (III-5ap) and the side chain group $R^{36}$ is compounds of (III-5a) to (III-5e), (III-5g) to (III-5l), (III-5ak) to (III-5ap), (III-5ar) to (III-5aw) and (III-5ay) to (III-5bf), and (III-biv): compounds in which $k^{32}$ is 1 and one of $Z^{33}$ and $Z^{34}$ is a single bond, illustratively, compounds having basic structures of general formulae (III-2f) to (III-2i) in which the side chain group $R^{32}$ is compounds of (III-5a) to (III-5e) and (III-5ak) to (III-5ap) and the side chain group $R^{36}$ is compounds of (III-5a) to (III-5e), (III-5g) to (III-5l), (III-5ak) to (III-5ap), (III-5ar) to (III-5aw) and (III-5ay) to (III-5bf).

Among compounds of the aforementioned general formula (III-3) in which $R^{33}$ is an alkyl group having 1 to 5 carbon atoms or an alkenyl group having 2 to 5 carbon atoms and R is an alkyl or alkoxy group having 1 to 5 carbon atoms or an alkenyl or alkenyloxy group having 2 to 5 carbon atoms, (III-bv): compounds in which $k^{33}$ is 0 and $Z^{36}$ is a single bond, —C≡C— or —CH=N—N=CH—, illustratively, compounds having basic structures of general formulae (III-3a) to (III-3c) and (III-3h) to (III-3p) in which the side chain group $R^{33}$ is compounds of (III-5a) to (III-5e) and (III-5ak) to (III-5ap) and the side chain group $R^{37}$ is compounds of (III-5a) to (III-5e), (III-5g) to (III-5l), (III-5ak) to (III-5ap), (III-5ar) to (III-5aw) and (III-5ay) to (III-5bf), (III-bvi): compounds in which $k^{33}$ is 1, $Z^3$ is a single bond, —(CH$_2$)$_2$—, —COO— or —C≡C— and $Z^{36}$ is a single bond, —COO— or —C≡C—, illustratively, compounds having basic structures of general formulae (III-3q) to (III-3bb), (III-3bd) to (III-3bg), (III-3bj) to (III-3ch) and (III-3cj) to (III-3di) in which the side chain group $R^{33}$ is compounds of (III-5a) to (III-5e) and (III-5ak) to (III-5ap) and the side chain group $R^{37}$ is compounds of (III-5a) to (III-5e), (III-5g) to (III-5l), (III-5ak) to (III-5ap), (III-5ar) to (III-5aw) and (III-5ay) to (III-5bf), (III-bvii): compounds in which one of $Z^{35}$ and $Z^{36}$ is a single bond and the other is a single bond or —C≡C— and at least one of $W^{34}$ and $W^{35}$ is F, illustratively, compounds having basic structures of general formulae (III-3r), (III-3t), (III-3au), (III-3aw), (III-3ay), (III-3bk), (III-3bn), (III-3bo), (III-3bz), (III-3cb), (III-3ce), (III-3cf), (III-3cu), (III-3cx) and (III-3cz), in which the side chain group $R^{33}$ is compounds of (III-5a) to (III-5e) and (III-5ak) to (III-5ap) and the side chain group $R^{37}$ is compounds of (III-5a) to (III-5e), (III-5g) to (III-5l), (III-5ak) to (III-5ap), (III-5ar) to (III-5aw) and (III-5ay) to (III-5bf), and (III-bviii): compounds in which either of $Y^{35}$ and $Y^{36}$ is a compound substituted by F or CH$_3$, illustratively, compounds having basic structures of general formulae (III-3c), (III-3f), (III-3g), (III-3j), (III-3l) to (III-3o), (III-3s), (III-3u) to (III-3w), (III-3z), (III-3ab), (III-3ae), (III-3ag), (III-3ai), (III-3aj), (III-3an), (III-3ao), (III-3aq) to (III-3as), (III-3av), (III-3ax), (III-3az) to (III-3bb), (III-3bl), (III-3bm), (III-3bp) to (III-3bs), (III-3bv), (III-3ca), (III-3cc), (III-3od), (III-3cg), (III-3ch), (III-3cm) to (III-3cs), (III-3cv) to (III-3cx), (III-3da) to (III-3dc) in which the side chain group $R^{33}$ is compounds of (III-5a) to (III-5e) and (III-5ak) to (III-5ap) and the side chain group $R^{37}$ is compounds of (III-5a) to (III-5e), (III-5g) to (III-5l), (III-5ak) to (III-5ap), (III-5ar) to (III-5aw) and (III-5ay) to (III-5bf).

(III-bix): Compounds of the aforementioned general formula (III-4) in which $R^{34}$ is an alkyl group having 1 to 5 carbon atoms or an alkenyl group having 2 to 5 carbon atoms, $R^{38}$ is an alkyl or alkoxy group having 1 to 5 carbon atoms or an alkenyl or alkenyloxy group having 2 to 5 carbon atoms and $k^{34}+k^{35}$ is 0, illustratively, compounds having basic structures of general formulae (III-4a) and (III-4b) in which the side chain group $R^{34}$ is compounds of (III-5a) to (III-5e) and (III-5ak) to (III-5ap) and the side chain group $R^{38}$ is compounds of (III-5a) to (III-5e), (III-5g) to (III-5l), (III-5ak) to (III-5ap), (III-5ar) to (III-5aw) and (III-5ay) to (III-5bf).

A nematic liquid crystal composition which contains one or two or more compounds selected from the compounds represented by these subgroups (III-bi) to (III-bix), wherein the total content of these compounds is from 10 to 100% by weight as the liquid crystal component C, is desirable.

Particularly preferred mode of the compounds represented by general formulae (III-1) to (III-4) is a liquid crystal component C which contains the following compounds.

Inclusion of the compounds of general formulae (III-1) to (III-4) as a liquid crystal component C exerts characteristic effects in that viscosity and viscoelasticity can be reduced and specific resistance and voltage holding ratio become relatively high. It is desirable that viscosity of the liquid crystal component C is as low as possible and, in the case of the present invention, the viscosity is preferably 45 cp or less, more preferably 30 cp or less, most preferably 20 cp or less and particularly preferably 15 cp or less. From such a point of view, more preferred compounds are, (III-ci): compounds having basic structures of (III-1a) to (III-1f), (III-1k), (III-2a) to (III-2f), (III-3a), (III-3h) to (III-3j), (III-3o), (III-3p), (III-3q), (III-3ac), (III-3at) to (III-3ax), (III-3ba), (III-3bb), (III-3bf), (III-3bg), (III-3bx) to (III-3cb) and (III-3ct) to (III-3cx), more preferably, (III-cii): compounds of the aforementioned (III-ci) in which $R^{31}$ to $R^{34}$ are a straight chain alkyl group having 2 to 5 carbon atoms or an alkenyl group of $CH_2=CH—(CH_2)_q$ (q=0 or 2) and $R^{35}$ to $R^{38}$ are a straight chain alkyl group having 1 to 5 carbon atoms or an alkenyl group of $CH_2=CH—(CH_2)_q$ (q=0 or 2), most preferably (III-ciii): compounds having basic structures of (III-1a), (III-1d), (III-2a), (III-2f), (III-3a), (III-3h), (III-3p) and (III-3g), in which both side chain groups are alkenyl groups.

Though the liquid crystal component C of the present invention can be constructed solely with any one of the compounds represented by the general formula (III-1), general formula (III-2), general formula (III-3) and general formula (III-4), the birefringence of the liquid crystal composition can be optimized easily in response to its use, by jointly using (III-civ): compounds represented by the general formula (III-1) and/or general formula (III-2), particularly compounds of general formulae (III-1a), (III-1d), (III-2a) to (III-2c) and (III-2f) and (III-cv): compounds represented by the general formula (III-3) and/or general formula (III-4), particularly those compounds in which $Z^{35}$ is a single bond, —C≡C— or —CH=N—N=CH—, illustratively, compounds of general formulae (III-3a), (III-3h), (III-3p), (III-3q), (III-3at), (III-4a) and (III-4h). For general purpose use, the birefringence can be reduced, and reduction of non-uniformity of color on liquid crystal display systems, improvement of viewing angle characteristics and increment of contrast ratio can be achieved easily, by frequently using compounds of general formula (III-1) and general formula (III-2), such as compounds of general formulae (III-1a) to (III-2f). Also, when compounds of the general formula (III-3) such as compounds of general formulae (III-3a) to (III-3j) or of the general formula (III-4) such as compounds of general formulae (III-4a) to (III-4e) are used frequently, the birefringence can be increased and preparation of a liquid crystal display device having a thin liquid crystal layer of from 1 to 5 μm becomes possible.

A liquid crystal component C which contains these compounds of (III-ai) to (III-cv) has a feature in that it can mix thoroughly with the essential component, liquid crystal component A, and is useful in controlling the birefringence, improving sharpness or temperature-dependency thereof or improving response property depending on each purpose. These compounds are excellent in at least one of such effects, and these effects can be obtained even by a small content of from 0.1 to 30% by weight based on the total amount of the nematic liquid crystal composition of the present invention.

In the compounds of the present invention, the composing atoms can be replaced by their corresponding isotopic atoms consciously. In that case, compounds in which hydrogen atoms are replaced by deuterium atoms are particularly desirable, because they exert more desirable effects on miscibility, elastic constant, pre-tilt angle, voltage holding ratio and the like factors. Preferred are compounds in which hydrogen atoms existing in the aforementioned side chain groups, linking groups or rings are replaced by deuterium atoms. More preferably, the side chain groups are substituted or unsubstituted alkyl groups and alkenyl groups, the rings are substituted or unsubstituted 1,4-phenylene, pyrimidine-2,5-diyl, trans-1,4-cyclohexylene, trans-1,4-cyclohexenylene and trans-1,4-dioxane-2,5, diyl and the linking groups are —$CH_2O$—, —$OCH_2$—, —$(CH_2)_2$—, —$(CH_2)_4$—, —CH=CH—$(CH_2)_2$—, —$(CH_2)_2$—CH=CH—, —CH=N— and —CH=N—N=CH—. Particularly preferred are alkyl groups, alkenyl groups, 1,4-phenylene, trans-1,4-cyclohexylene, —$(CH_2)_2$— and —$(CH_2)_4$—.

Currently, polyimide-based orientation films such as LX1400, SE150, SE610, AL1051 and AL3408 are frequently used in TN-LCD, STN-LCD or TFT-LCD. Liquid crystal display characteristics, display quality, reliability and productivity are deeply related to the specification of orientation films, and pre-tilt angle characteristics for example are important for liquid crystal materials. In order to obtain desired liquid crystal display characteristics and uniform orientation, it is necessary to adjust the size of pre-tilt angle as occasion demands. For example, the orientation becomes unstable in the case of a large pre-tilt angle, and sufficient display characteristics cannot be obtained when the angle is small.

The present inventors have found that liquid crystal materials having larger pre-tilt angle and liquid crystal materials having smaller angle can be sorted out and that desired liquid crystal display characteristics and uniform orientation can be obtained from liquid crystal materials by the application of this finding. This technique can be applied to the present invention. For example, a case in which the liquid crystal component B contains compounds of the general formulae (II-1) to (II-4) is as follows. More larger pre-tilt angle can be obtained by increasing the content of compounds in which $R^{21}$ is an alkenyl group, $X^{21}$ is F, Cl or —CN and $Y^{21}$ and $Y^{22}$ are F and/or compounds in which $R^{21}$ is an alkyl group, $X^{21}$ is F, Cl or —CN and $Z^{22}$ is —$C_2H_4$— or —$C_4H_8$—, and more smaller pre-tilt angle can be obtained by increasing the content of compounds in which $R^{21}$ is an alkenyl group or $C_sH_{2s+1}$—O—$C_tH_{2t}$, $X^{21}$ is F, $Y^{21}$ is F and $Y^{22}$ is H and/or compounds in which $Z^{22}$ is —COO—. Illustratively, in the case of compounds in which rings $A^{21}$ to $A^{24}$ in the general formulae (II-1), (II-2) and (II-4) and rings $A^{31}$ to $A^{35}$ in the general formulae (III-1) to (III-4) are cyclohexane rings and hydrogen atoms of said rings are replaced by deuterium atoms, the pre-tilt angle varies depending on the replaced positions and can therefore be controlled within wide range.

Also, frequent use of compounds in which hydrogen atoms are replaced by deuterium atoms exerts special effect to maintain further high voltage holding ratio and therefore is desirable in terms of the display characteristics and production yield of TFT-LCD, PDLC, PN-LCD and the like devices for active use. The reason for such an effect may be that properties of heavy water, namely differences in equilibrium constant and rate constant of the reaction, low ionic mobility, low solubility of inorganic substances and oxygen and the like properties, are also expressed in the liquid crystal compounds. In order to maintain more higher voltage holding ratio, it can mostly be achieved by including 10 to 40% by weight or more larger amount of the aforementioned compounds based on the total amount of the liquid crystal composition.

The content of each liquid crystal component in the nematic liquid crystal composition of the present invention is as follows. The content of the liquid crystal component A is within the range of from 5 to 70% by weight, preferably within the range of from 5 to 60% by weight, more preferably within the range of from 5 to 50% by weight. The content of the liquid crystal component B is within the range of from 0 to 95% by weight, preferably within the range of from 3 to 80% by weight, more preferably within the range of from 5 to 60% by weight. The content of the liquid crystal component C is up to 95% by weight at the most, preferably within the range of from 3 to 70% by weight, more preferably within the range of from 5 to 70% by weight. The content of compounds represented by the general formulae (I-1) to (I-18) is preferably 10% by weight or less as a single compound, and it is desirable that more larger content is composed of two or more compounds. The content of compounds represented by the general formulae (II-1) to (II-4), illustratively compounds represented by the general formulae (II-1a) to (II-4g), is preferably 30% by weight or less, more preferably 25% by weight or less, as a single compound, and it is desirable that more larger content is composed of two or more compounds, and their content in the liquid crystal component B is within the range of from 10 to 100% by weight, preferably within the range of from 50 to 100% by weight, more preferably within the range of from 75 to 100% by weight. The content of compounds represented by the general formulae (III-1) to (III-4), illustratively compounds represented by the general formulae (III-1a) to (III-4o), is preferably 30% by weight or less, more preferably 25% by weight or less, as a single compound, and it is desirable that more larger content is composed of two or more compounds, and their content in the liquid crystal component C is within the range of from 10 to 100% by weight, preferably within the range of from 50 to 100% by weight, more preferably within the range of from 75 to 100% by weight.

In order to improve characteristics of the liquid crystal composition of the present invention, the composition may further contain usually used nematic liquid crystals, smectic liquid crystals, cholesteric liquid crystals and the like liquid crystal compounds, in addition to the aforementioned compounds represented by general formulae (I-1) to (III-4). For example, one or a plurality of compounds having a core structure composed of 4 six-membered rings and having a liquid crystal phase-isotropic liquid phase transition temperature of 100° C. or more can be included. However, since the use of such compounds in a large amount reduces characteristics of the nematic liquid crystal composition, the amount is limited in response to the required characteristics of the nematic liquid crystal composition.

The crystal phase- or smectic phase-nematic phase transition temperature is preferably −10° C. or less, more preferably −20° C. or less, most preferably −30° C. or less. The nematic phase-isotropic liquid phase transition temperature is preferably 50° C. or more, more preferably 70° C. or more, most preferably within the range of from 80° C. to 150° C. The liquid crystal composition of the present invention may have a dielectric anisotropy of 3 or more but preferably within the range of from 4 to 40, and a range of from 4 to 16 is desirable when quick response is important or a range of from 17 to 30 is desirable when more lower driving voltage is required. Smaller or medium birefringence is within the range of preferably from 0.08 to 0.195, more preferably from 0.10 to 0.18. The nematic liquid crystal composition having such characteristics is effective for use in twisted nematic or super twisted nematic liquid crystal display devices.

When more quicker response is desired for the size of driving voltage, the liquid crystal composition of the present invention can be controlled as follows. When medium degree of driving voltage is desired, the liquid crystal composition of the present invention may preferably have a dielectric anisotropy within the range of from 3 to 15 and a viscosity within the range of from 8 to 20 c.p. at 20° C. In that case, viscosity of the liquid crystal component C alone is preferably 25 c.p. or less, more preferably 15 c.p. or less, most preferably 10 c.p. or less. Also, when particularly low driving voltage is desired, the liquid crystal composition of the present invention may have a dielectric anisotropy within the range of preferably from 15 to 30, more preferably from 18 to 28.

The aforementioned nematic liquid crystal composition is useful in quick response TN-LCD and STN-LCD and also in liquid crystal display devices in which color display can be made by birefringence of liquid crystal phase and retardation film without using color filter layers and can be used in a transmission type or reflection type liquid crystal display device. Since this liquid crystal display device has substrates having transparent electrode layers, in which at least one of them is transparent, molecules of the aforementioned nematic liquid crystal composition can be arranged between these substrates in a twisted orientation which can be selected in response to each object within the range of from 30° to 360°, preferably within the range of from 90° to 270°, more preferably within the range of from 45° to 135° or within the range of from 180° to 260°. Because of this, the liquid crystal composition of the present invention can contain a compound having an optically active group which shows an induced helical pitch of from 0.5 to 1,000 μm. Examples of such a compound include cholesterol derivatives, chiral nematic liquid crystals, ferroelectric liquid crystals and the like, more illustratively, cholesterylnonanate, C-15, CB-15, S-811 and the like may be used preferably. Also, it is known that there are compounds whose induced helical pitch becomes long and or short by the increment of temperature, and one or a plurality of compounds of one of such types may be used or one or a plurality of compounds of both types may also be used. Their amount to be mixed is preferably within the range of from 0.001% by weight to 10% by weight, more preferably within the range of from 0.05% by weight to3% by weight. Most preferably within the range of from 0.1% by weight to 3% by weight. As a matter of course, however, these amounts are selected to obtain a desired induced helical pitch by the helix angle θ and the thickness d between the aforementioned substrates.

It is desirable to select the pre-tilt angle which is obtained by the orientation film arranged on the transparent electrode substrate within the range of from 1° to 20°, and a pre-tilt angle of from 1° to 4° is desirable when the helix angle is from 30° to 100°, a pre-tilt angle of from 2° to 6° is desirable when the helix angle is from 100° to 180°, a pre-tilt angle of from 3° to 12° is desirable when the helix angle is from 180° to 260° and a pre-tilt angle of from 6° to 20° is desirable when the, helix angle is from 260° to 360°.

The present invention also provides phenyl benzoate derivatives represented by the general formula (I) and as intermediates for use in the production thereof 2-fluoro-4-(3-alkenyl)benzoic acid represented by the general formula (II). The group R represents a hydrogen atom or a straight chain alkyl group having 1 to 7 carbon atoms, preferably a hydrogen atom or methyl group. When R is an alkyl group, it is desirable that configuration of the double bond is trans configuration. Each of X, Y and Z is independently a fluorine atom or a hydrogen atom, but it is desirable that at least one of X, Y and Z is a fluorine atom, more preferably at least two of them are fluorine atoms, in order to improve the threshold voltage reducing effect through the increment of dielectric anisotropy. Also, since solubility and liquid crystalline property are slightly reduced when all of X, Y and Z are fluorine atoms, it is desirable that at least one of them is a hydrogen atom. In consequence, it is most desirable that X is a fluorine atom and Y is a hydrogen atom when Z is a fluorine atom and that X and Y are both fluorine atoms when Z is a hydrogen atom.

The following describes examples for production methods of the phenyl benzoic acid derivatives of the present invention represented by the general formula (I):

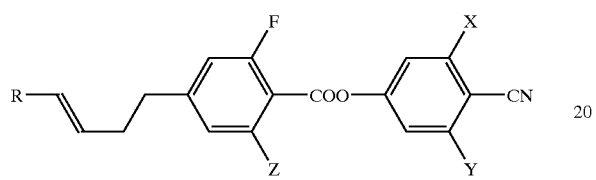
(I)

Namely, the derivative (I) can be obtained easily by treating a fluorine-substituted 4-(3-alkenyl)benzoic acid represented by the general formula (II)

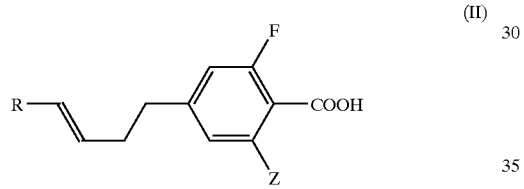
(II)

(wherein R and Z are as defined in the foregoing) with thionyl chloride or the like chlorination agent to convert it into corresponding acid chloride which is then allowed to react with a 4-cyanophenol or a fluorine substitution product thereof represented by the general formula (IV)

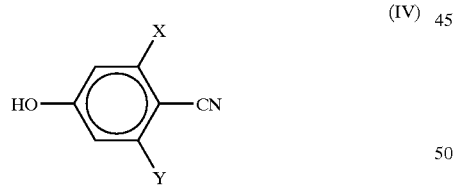
(IV)

(wherein X and Y are as defined in the foregoing) in the presence of pyridine or the like base. It can also be obtained by allowing the compound (II) to react directly, without converting it into acid chloride, with the compound (IV) in the presence of dicyclohexylcarbodiimide (DCC) or the like condensing agent.

In this connection, the fluorine-substituted 4-(3-alkenyl) benzoic acid of formula (II) can be produced in the following manner in response to its group Z.

(a) When Z is a fluorine atom, 1) a Grignard reagent prepared from 3,5-difluoro-1-bromobenzene (Va)

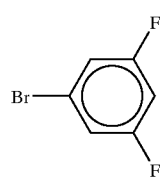
(Va)

or a phenyllithium reagent is allowed to react with N,N-dimethylformamide (DMF) or the like formylation agent and then treated with sodium borohydride or the like reducing agent to obtain 3,5-difluorobenzyl alcohol (VIa):

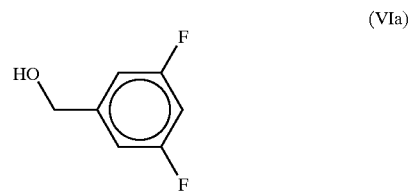
(VIa)

Alternatively, the compound (VIa) can also be obtained with one step by allowing the Grignard reagent or phenyllithium reagent to react with formaldehyde in stead of the formulation agent. By allowing 3,5-difluorobenzyl bromide (VIIa)

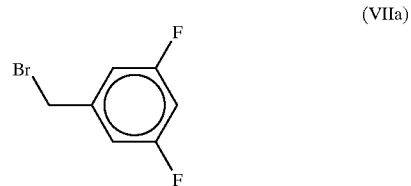
(VIIa)

obtained by bromination of the compound (VIa) to react with a Grignard reagent represented by the general formula (VIIIa):

(VIIIa)

(wherein R is as defined in the foregoing, and W is chlorine or bromine atom), a 3,5-difluoro-1-(3-alkenyl)benzene represented by the general formula (IXa)

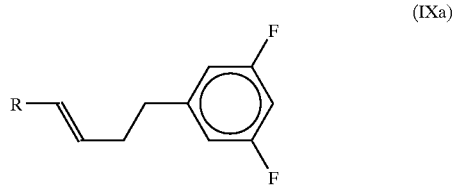
(IXa)

(wherein R is as defined in the foregoing) is obtained. Alternatively, the compound (IXa) can also be obtained by carrying out the reaction with a Grignard reagent represented by the general formula (VIIIb)

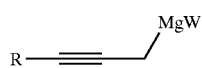

(wherein R is as defined in the foregoing, and W is chlorine or bromine atom), in stead of the reagent (VIIIa), and then trans-reducing the resulting triple bond by alkali metal such as sodium or lithium in liquid ammonia or a lower amine, and the latter case is desirable when R is an alkyl group. By treating this with butyl lithium or the like alkyl lithium and then allowing to react with carbon dioxide, a 2,6-difluoro-4-(3-alkenyl)benzoic acid (IIa)

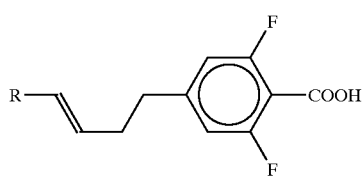

(wherein R is as defined in the foregoing), which is a member of the fluorine-substituted 4-(3-alkenyl)benzoic acid represented by the general formula (II) in which Z is a fluorine atom, can be obtained.

2) Alternatively, by allowing the Grignard reagent or a phenyllithium reagent prepared from the compound (Va) to react with an unsaturated carboxylic acid derivative represented by the general formula (X)

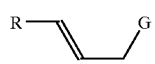

(wherein R is as defined in the foregoing, G is CN, COOR' or COCl, and R' is a lower alkyl group having 1 to 4 carbon atoms) and then hydrolyzing the reaction product as occasion demands, a compound represented by the general formula (XIa)

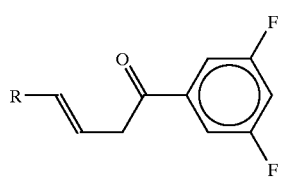

(wherein R is as defined in the foregoing) is obtained. By reducing the carbonyl group, the aforementioned compound of formula (IXa) can be obtained.

(b) When Z is hydrogen atom, 3) a Grignard reagent prepared from 3-fluoro-1-bromobenzene (Vb)

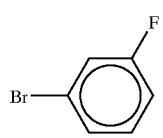

or a phenyllithium reagent is allowed to react in the same manner as described in (a)-1) and the subsequent reaction is carried out in the same manner, thereby obtaining a compound represented by the general formula (IXb)

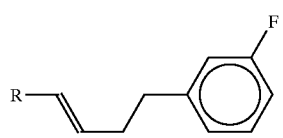

(wherein R is as defined in the foregoing). By subjecting this to acetylation and subsequent oxidation with a hypochlorite, a 2-fluoro-4-(3-alkenyl)benzoic acid (IIb)

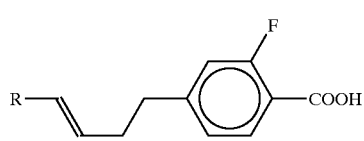

(wherein R is as defined in the foregoing), which is a member of the fluorine-substituted 4-(3-alkenyl)benzoic acid represented by the general formula (II) in which Z is a hydrogen atom, can be obtained.

4) Alternatively, an acid chloride derived from the compound (IIb) can be directly obtained by allowing the compound (IXb) to react with oxalyl chloride in the presence of Lewis acid.

5) Alternatively, using a compound (Vc)

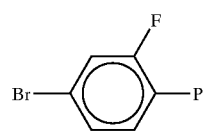

(wherein P is 4,4-dimethyl-1,3-oxazolin-2-yl group or the like carboxyl group-protecting group) which contains protected carboxyl group, in stead of 3-fluoro-1-bromobenzene (Vb), a compound represented by the general formula (XIIb)

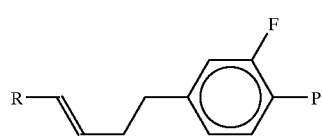

(wherein R and P are as defined in the foregoing) can be obtained in the same manner as described in the aforementioned step 2) or 3). The benzoic acid derivative of formula (IIb) can also be obtained by removing this protecting group.

These fluorine-substituted 4-(3-alkenyl)benzoic acids and 2,6-difluoro-4-(3-alkenyl)benzoic acids of the general formula (II), are novel compounds and markedly useful as production intermediates of not only compounds (I) of the present invention but also other various liquid crystal compounds, and the present invention also provides these compounds of formula (II).

Typical examples of the compounds represented by the general formula (I) thus produced by the aforementioned production methods are shown in Table 1.

TABLE 1

Phase transition temperature of the compounds of general formula (I)

| No. | Compound | Phase transition temp. |
|---|---|---|
| (I)-1 | [Structure: allyl-substituted difluorophenyl-COO-fluorophenyl-CN] | Cr 58.6 I |
| (I)-2 | [Structure: 2-butenyl-substituted difluorophenyl-COO-difluorophenyl-CN] | Cr 62.0 I |

(In the table, Cr means crystal phase and I means isotropic liquid phase. The phase transfer temperature is "° C.".)

The compound (I) of the present invention has a structural feature in that it has 3-alkenyl groups as its side chain groups, in stead of alkyl groups. A large number of compounds having alkenyl groups as the side chains have been known, and it has been reported that they have various characteristics in comparison with similar compounds in which their corresponding side chains are alkyl groups, but reports on the compounds in which 3-alkenyl groups are directly bonded to the benzoic acid nucleus are extremely scarce, and virtually nothing is known about a high P type compound such as of the general formula (I-6) in which a fluorine atom is introduced into the benzoic acid nucleus. The compound of the present invention has rendered possible the solution to the aforementioned problems by providing its structure with such characteristics.

Also, as shown in Table 1, some of the compounds represented by the general formula (I) do not show nematic liquid crystalline properties by itself. However, dropping degree of the nematic phase-isotropic liquid phase transition temperature ($T_{N-1}$) when they are added to the host liquid crystal composition is at least the same as the case of the compound of general formula (I-6) and not so large when compared with the compounds of group A1 having small number of substituted fluorine atoms. In addition, since they have relatively low melting point and are excellent in their miscibility with other liquid crystal compositions, a problem of causing precipitation and the like is scarce. In consequence, they can be used suitably in the form of their mixture with other liquid crystal compounds, particularly as materials of TN type, STN type and the like field-effect type display cells.

Typical examples of nematic liquid crystal compounds which can be used by mixing with the compounds represented by the general formula (I) include phenyl benzoate derivatives, phenyl cyclohexanecarboxylate derivatives, biphenyl-4-yl cyclohexanecarboxylate derivatives, phenyl cyclohexanecarbonyloxybenzoate derivatives, phenyl cyclohexylbenzoate derivatives, cyclohexyl cyclohexylbenzoate derivatives, biphenyl derivatives, cyclohexylbenzene derivatives, terphenyl derivatives, bicyclohexane derivatives, 4-cyclohexylbiphenyl derivatives, 4-phenylbicyclohexane derivatives, tercyclohexane derivatives, 1,2-dicyclohexylethane derivatives, 1,2-diphenylethane derivatives, 1,2-diphenylethine derivatives, (2-cyclohexylethyl)benzene derivatives, 4-phenetylbicyclohexane derivatives, 4-(2-cyclohexylethyl) biphenyl derivatives, 1-(4-phenyl)cyclohexyl-2-cyclohexylethane derivatives, 1-(4-cyclohexylphenyl)-2-phenylethine derivatives, phenylpyrimidine derivatives, (4-biphenyl-4-yl)pyrimidine derivatives, phenylpyridine derivatives, (4-biphenyl-4-yl)pyridine derivatives and the like.

The liquid crystal composition of the present invention can be obtained by including the liquid crystal components A, B and C described in detail in the foregoing. Though nematic liquid crystal compositions (1-01) to (1-16) are shown in the following as preferred examples, the present invention is not restricted by these examples. Among these examples, nematic liquid crystal compositions (1-01) to (1-05) and (1-11) to (1-16) can be used in TN-LCD, nematic liquid crystal compositions (1-06) to (1-09) can be used in STN-LCD and nematic liquid crystal composition (1-16) can be used in PDLC and PN-LCD. In addition, depending on each desired object and use, one or a plurality of compounds (1-0101) to (1-1610) represented by these examples can be replaced by certain compounds of the general formulae (I-1) to (III-4), illustratively, compounds having basic structures of general formulae (I-1) to (I-18).in which their side chain groups are (I-a) to (I-bc), compounds having basic structures of general formulae (II-1a) to (II-4g) in which their side chain groups are (II-5a) to (II-5r) and partial structures of the polar groups are general formulae (II-6a) to (II-6r) and compounds having basic structures of general formulae (III-1a) to (III-4o) in which their side chain groups are (III-5a) to (III-5bf). As preferred examples of the composition, nematic liquid crystal compositions (1-01) to (1-16) are shown in the following.

| Nematic liquid crystal composition (1-01) | | (% by weight) |
|---|---|---|
| (1-0101) | C₃H₇–[Cy]–[Cy]–OCH₃ | 10 |
| (1-0102) | C₃H₇–[Cy]–[Cy]–OC₃H₇ | 10 |
| (1-0103) | C₃H₇–[Cy]–[Ph]–OCH₃ | 5 |
| (1-0104) | C₅H₁₁–[Cy]–[Ph]–C₃H₇ | 5 |
| (1-0105) | C₂H₅–[Ph]–C≡C–[Ph]–OC₂H₅ | 5 |
| (1-0106) | C₂H₅–[Ph]–COO–[Ph(F)]–CN | 5 |
| (1-0107) | CH₂=CH-CH₂-CH₂-[Ph]–COO–[Ph(F)]–CN | 6 |
| (1-0108) | C₅H₁₁–[Ph]–COO–[Ph(F)]–CN | 6 |
| (1-0109) | C₇H₁₅–[Ph]–COO–[Ph(F)]–CN | 10 |
| (1-0110) | C₅H₁₁–[Cy]–[Ph]–[Ph]–C₂H₅ | 8 |
| (1-0111) | C₃H₇–[Cy]–[Ph]–COO–[Ph(F)]–CN | 5 |
| (1-0112) | C₄H₉–[Cy]–[Ph]–COO–[Ph(F)]–CN | 5 |

-continued
| Nematic liquid crystal composition (1-01) | | |
|---|---|---|
| | | (% by weight) |
| (1-0113) | 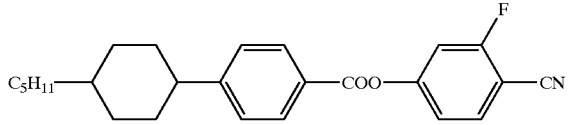 | 5 |
| (1-0114) | 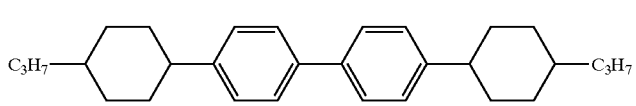 | 5 |
| (1-0115) | 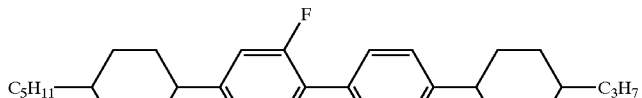 | 5 |
| (1-0116) | 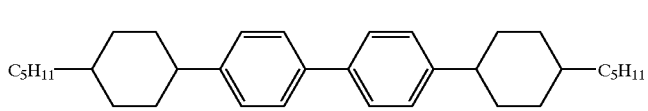 | 5 |
| Nematic liquid crystal composition (1-02) | | |
|---|---|---|
| | | (% by weight) |
| (1-0201) | 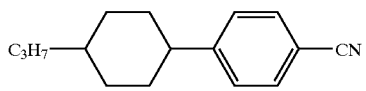 | 17 |
| (1-0202) | 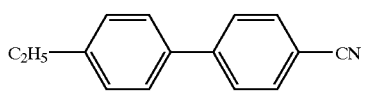 | 12 |
| (1-0203) | 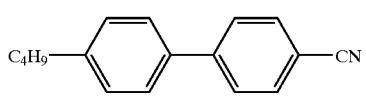 | 11 |
| (1-0204) | 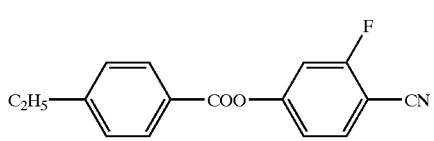 | 5 |
| (1-0205) | 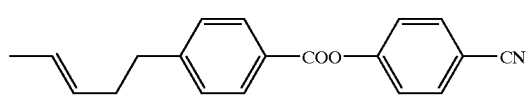 | 10 |
| (1-0206) | 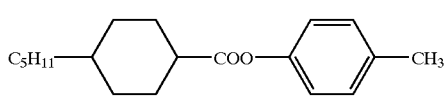 | 10 |
| (1-0207) | 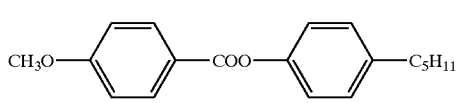 | 7 |
| (1-0208) | 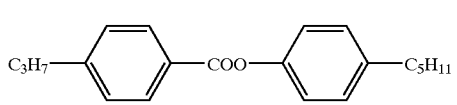 | 8 |

-continued

Nematic liquid crystal composition (1-02)

| | | (% by weight) |
|---|---|---|
| (1-0209) | C$_3$H$_7$—⬡—COO—⬢—⬡—C$_3$H$_7$ | 5 |
| (1-0210) | C$_3$H$_7$—⬡—⬡—COO—⬢(F)—C$_2$H$_5$ | 5 |
| (1-0211) | C$_3$H$_7$—⬡—⬡—C$_2$H$_4$—⬢—CH$_3$ | 5 |
| (1-0212) | C$_3$H$_7$—⬡—⬢—COO—⬢—C$_2$H$_5$ | 5 |

Nematic liquid crystal composition (1-01)

| | | (% by weight) |
|---|---|---|
| (1-0301) | C$_2$H$_5$—⬢—COO—⬢(F)—CN | 8 |
| (1-0302) | C$_5$H$_{11}$—⬢—COO—⬢(F)—CN | 10 |
| (1-0303) | CH$_2$=CHCH$_2$CH$_2$—⬢—COO—⬢(F,F)—CN | 7 |
| (1-0304) | C$_3$H$_7$—⬡—⬢—OCH$_3$ | 12 |
| (1-0305) | C$_3$H$_7$—⬡—⬡—OC$_3$H$_7$ | 18 |
| (1-0306) | C$_3$H$_7$—⬡—⬢—⬢—C$_2$H$_5$ | 10 |
| (1-0307) | C$_3$H$_7$—⬡—⬢—⬢—⬡—C$_3$H$_7$ | 5 |

-continued
Nematic liquid crystal composition (1-01)
| | | (% by weight) |
|---|---|---|
| (1-0308) |  | 5 |
| (1-0309) |  | 5 |
| (1-0310) |  | 5 |
| (1-0311) | 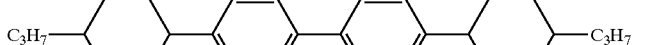 | 5 |
| (1-0312) | 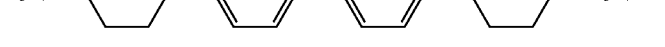 | 5 |
| (1-0313) |  | 5 |
Nematic liquid crystal composition (1-04)
| | | (% by weight) |
|---|---|---|
| (1-0401) | 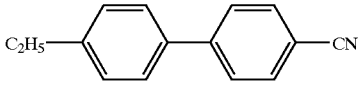 | 12 |
| (1-0402) | 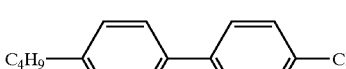 | 12 |
| (1-0403) | 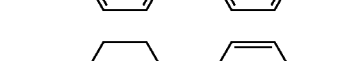 | 18 |
| (1-0404) | 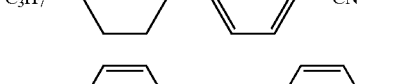 | 6 |
| (1-0405) | 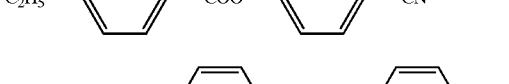 | 6 |

-continued
Nematic liquid crystal composition (1-04)
| | | (% by weight) |
|---|---|---|
| (1-0406) | 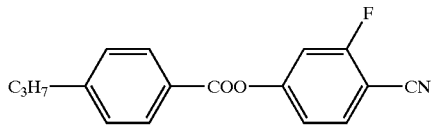 | 5 |
| (1-0407) | 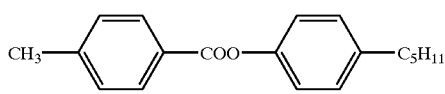 | 10 |
| (1-0408) | 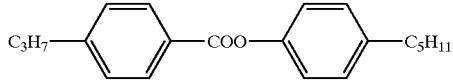 | 12 |
| (1-0409) | 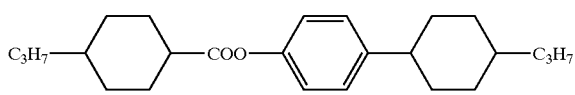 | 7 |
| (1-0410) | 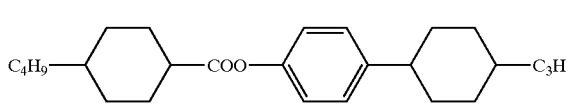 | 7 |
| (1-0411) | 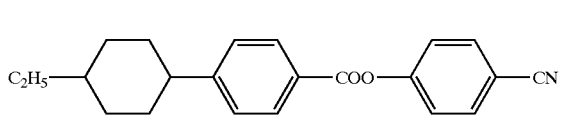 | 5 |
Nematic liquid crystal composition (1-05)
| | | (% by weight) |
|---|---|---|
| (1-0501) | 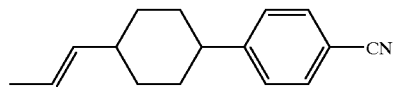 | 8 |
| (1-0502) | 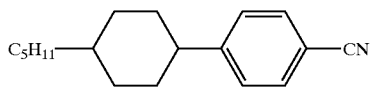 | 6 |
| (1-0503) | 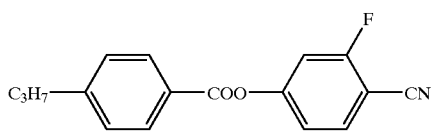 | 7 |
| (1-0504) | 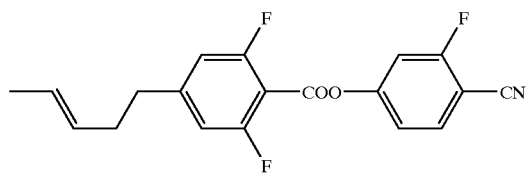 | 10 |
| (1-0505) | 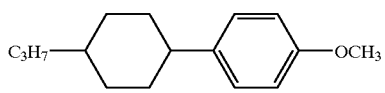 | 11 |

-continued

Nematic liquid crystal composition (1-05)

| | | (% by weight) |
|---|---|---|
| (1-0506) | CH2=CH-CH2-[Cy]-[Cy]-CH2-CH2-CH=CH2 | 10 |
| (1-0507) | C3H7-[Cy]-[Cy]-OC3H7 | 10 |
| (1-0508) | C5H11-[Cy]-[Cy]-OCH3 | 10 |
| (1-0509) | C5H11-[Cy]-[Cy]-OC2H5 | 9 |
| (1-0510) | CH3-[Ph]-C≡C-[Ph]-OC2H5 | 3 |
| (1-0511) | C2H5-[Ph]-C≡C-[Ph]-OCH3 | 3 |
| (1-0512) | C3H7-[Cy]-[Cy]-COO-[Cy]-C3H7 | 4 |
| (1-0513) | C4H9-[Cy]-[Cy]-COO-[Cy]-C3H7 | 3 |
| (1-0514) | C3H7-[Cy]-[Cy]-COO-[Cy]-C5H11 | 3 |
| (1-0515) | C4H9-[Cy]-[Cy]-COO-[Cy]-C5H11 | 3 |

Nematic liquid crystal composition (1-06)

| | | (% by weight) |
|---|---|---|
| (1-0601) | CH2=CH-CH2-CH2-[Cy]-[Ph]-CN | 12 |
| (1-0602) | C3H7-CH=CH-[Cy]-[Ph]-CN | 11 |
| (1-0603) | C3H7-[Ph]-COO-[Ph]-CN | 7 |

-continued

Nematic liquid crystal composition (1-06)

| No. | Structure | (% by weight) |
|---|---|---|
| (1-0604) | C₃H₇OCH₂–C₆H₄–COO–C₆H₃(F)–CN | 7 |
| (1-0605) | CH₂=CH–CH₂–CH₂–C₆H₄–COO–C₆H₂(F)(F)–CN | 11 |
| (1-0606) | C₃H₇–Cy–Cy–C₆H₄–CH₃ | 6 |
| (1-0607) | C₃H₇–Cy–Cy–C₆H₄–OCH₃ | 5 |
| (1-0608) | C₃H₇–Cy–Cy–C₆H₄–C₃H₇ | 5 |
| (1-0609) | C₃H₇–Cy–Cy–C₆H₄–F | 5 |
| (1-0610) | C₃H₇–Cy–Cy–C₆H₄–CN | 5 |
| (1-0611) | C₅H₁₁–Cy–Cy–C₆H₄–CN | 5 |
| (1-0612) | C₃H₇–Cy–C₆H₄–COO–C₆H₄–F | 5 |
| (1-0613) | C₃H₇–Cy–Cy–COO–C₆H₄–F | 5 |
| (1-0614) | C₅H₁₁–Cy–Cy–COO–C₆H₄–F | 5 |
| (1-0615) | C₃H₇–Cy–C₂H₄–C₆H₄–C≡C–C₆H₄–C₂H₅ | 3 |
| (1-0616) | C₃H₇–Cy–C₆H₃(F)–C≡C–C₆H₄–C₃H₇ | 3 |

| Nematic liquid crystal composition (1-07) | | (% by weight) |
|---|---|---|
| (1-0701) | 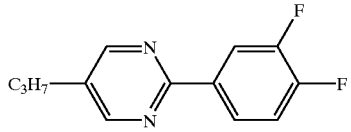 | 10 |
| (1-0702) | 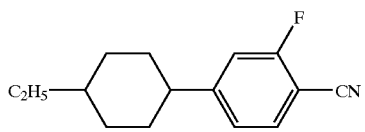 | 11 |
| (1-0703) | 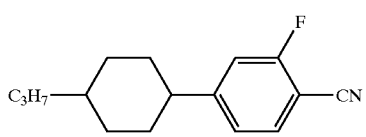 | 4 |
| (1-0704) | 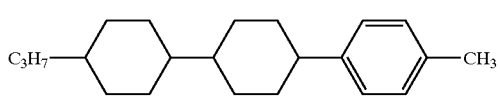 | 7 |
| (1-0705) | 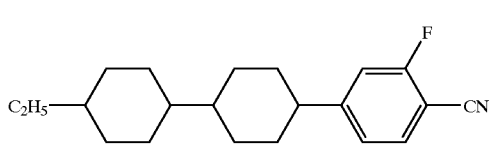 | 12 |
| (1-0706) | 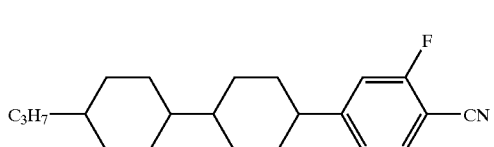 | 12 |
| (1-0707) | 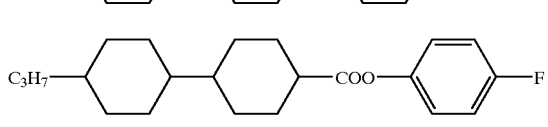 | 5 |
| (1-0708) | 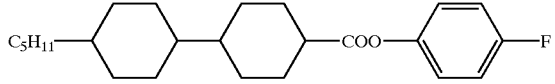 | 5 |
| (1-0709) | 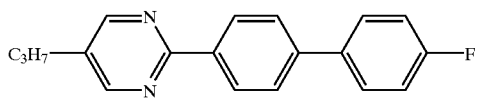 | 7 |
| (1-0710) | 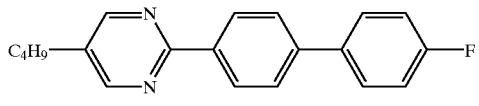 | 7 |
| (1-0711) |  | 4 |
| (1-0712) |  | 4 |

-continued
Nematic liquid crystal composition (1-07)
| | | (% by weight) |
|---|---|---|
| (1-0713) | 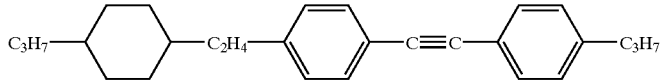 | 4 |
| (1-0714) | 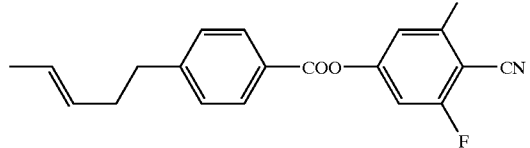 | 5 |
| (1-0715) | 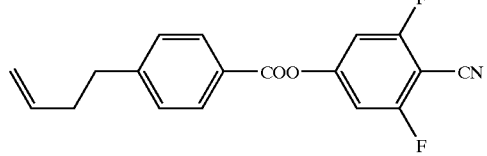 | 3 |
Nematic liquid crystal composition (1-08)
| | | (% by weight) |
|---|---|---|
| (1-0801) | 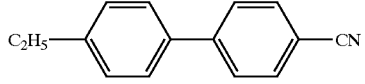 | 12 |
| (1-0802) | 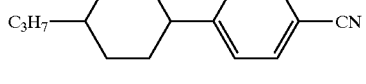 | 12 |
| (1-0803) | 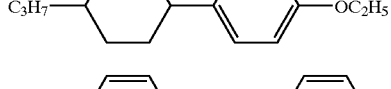 | 9 |
| (1-0804) | 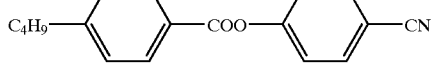 | 8 |
| (1-0805) | 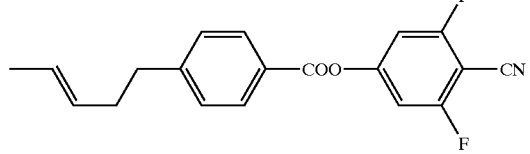 | 5 |
| (1-0806) | 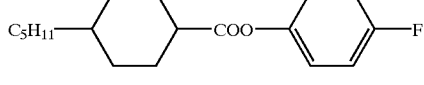 | 9 |
| (1-0807) | 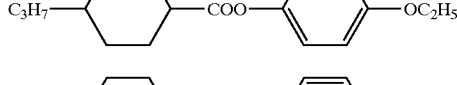 | 5 |
| (1-0808) | 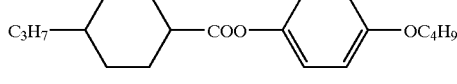 | 5 |

Nematic liquid crystal composition (1-08)

| | | (% by weight) |
|---|---|---|
| (1-0809) | C₅H₁₁–[Cy]–COO–[Ph]–OC₂H₅ | 5 |
| (1-0810) | C₃H₇–[Cy]–[Ph]–[Ph]–OC₂H₅ | 6 |
| (1-0811) | C₃H₇–[Cy]–[Ph]–[Ph]–OC₃H₇ | 5 |
| (1-0812) | C₂H₅–[Pyrimidine]–[Ph]–[Ph]–C₄H₉ | 4 |
| (1-0813) | C₃H₇–[Pyrimidine]–[Ph]–[Ph]–C₄H₉ | 5 |
| (1-0814) | C₂H₅–[Pyrimidine]–[Ph]–[Ph]–C₆H₁₃ | 5 |
| (1-0815) | C₃H₇–[Pyrimidine]–[Ph]–[Ph]–C₆H₁₃ | 5 |

Nematic liquid crystal composition (1-09)

| | | (% by weight) |
|---|---|---|
| (1-0901) | C₅H₁₁–[Cy]–[Cy]–C₃H₇ (with double bond) | 4 |
| (1-0902) | C₅H₁₁–[Cy]–[Cy]–C₃H₇ (with double bond) | 3 |
| (1-0903) | C₄H₉–[Ph]–COO–[Ph]–CN | 3 |
| (1-0904) | CH₂=CH–CH₂–CH₂–[Ph(F)]–COO–[Ph]–CN | 3 |
| (1-0905) | CH₂=CH–CH₂–CH₂–[Ph]–COO–[Ph(F)]–CN | 3 |

-continued

Nematic liquid crystal composition (1-09)

| | | (% by weight) |
|---|---|---|
| (1-0906) | C₃H₇–⌬–COO–⌬(F)–CN | 3 |
| (1-0907) | C₄H₉–⌬–COO–⌬(F)–CN | 4 |
| (1-0908) | CH₂=CH–Cy–Cy–⌬(F,F) | 18 |
| (1-0909) | CH₂=CH–Cy–Cy–⌬–CH₃ | 17 |
| (1-0910) | CH₂=CH–CH₂–Cy–Cy–⌬–CH₃ | 17 |
| (1-0911) | C₃H₇–Cy–Cy–⌬–O–CH₂–CH=CH–CH₃ | 4 |
| (1-0912) | C₃H₇–Cy–⌬–⌬–CH₂OCH₃ | 7 |
| (1-0913) | C₅H₁₁–Cy–⌬–⌬–CH₂OCH₃ | 4 |
| (1-0914) | C₃H₇–Cy–COO–⌬–C≡C–⌬–C₂H₅ | 5 |
| (1-0915) | C₃H₇–Cy–Cy–COO–⌬–Cy–C₃H₇ | 5 |

Nematic liquid crystal composition (1-10)

| | | (% by weight) |
|---|---|---|
| (1-1001) | CH₂=CH–Cy–⌬–CN | 10 |

-continued

Nematic liquid crystal composition (1-10)

| | | (% by weight) |
|---|---|---|
| (1-1002) | C₃H₅—⟨phenyl⟩—COO—⟨phenyl(F)⟩—CN | 5 |
| (1-1003) | C₃H₇—⟨phenyl⟩—COO—⟨phenyl(F)⟩—CN | 5 |
| (1-1004) | C₅H₁₁—⟨phenyl⟩—⟨phenyl⟩—CN | 5 |
| (1-1005) | C₅H₁₁—⟨pyrimidine⟩—⟨phenyl⟩—CN | 5 |
| (1-1006) | C₃H₇—⟨phenyl⟩—C≡C—⟨phenyl⟩—OC₂H₅ | 10 |
| (1-1007) | C₃H₇—⟨phenyl⟩—C≡C—⟨phenyl⟩—OC₂H₅ | 10 |
| (1-1008) | CH₂=CH—⟨cyclohexyl⟩—⟨cyclohexyl⟩—C₅H₁₁ | 20 |
| (1-1009) | CH₂=CH—⟨cyclohexyl⟩—⟨cyclohexyl⟩—⟨phenyl⟩—CH₃ | 10 |
| (1-1010) | CH₂=CH—⟨cyclohexyl⟩—⟨cyclohexyl⟩—⟨phenyl⟩—CH₂CH₂CH=CH₂ | 7 |
| (1-1011) | C₃H₇—⟨cyclohexyl⟩—⟨phenyl⟩—⟨phenyl⟩—CH₂CH₂CH=CH₂ | 3 |
| (1-1012) | C₃H₇—⟨cyclohexyl⟩—⟨phenyl⟩—C≡C—⟨phenyl⟩—C₂H₅ | 5 |
| (1-1013) | C₃H₇—⟨cyclohexyl⟩—COO—⟨phenyl⟩—C≡C—⟨phenyl⟩—C₂H₅ | 5 |

| Nematic liquid crystal composition (1-11) | | (% by weight) |
|---|---|---|
| (1-1101) | C₃H₇–[Cy]–[Ph]–CN | 7 |
| (1-1102) | C₅H₁₁–[Cy]–[Ph]–CN | 8 |
| (1-1103) | CH₂=CH–[Cy]–[Ph]–CN | 5 |
| (1-1104) | CH₂=CH–CH₂–[Cy]–[Ph]–CN | 10 |
| (1-1105) | CH₂=CH–CH₂–[Cy]–[Cy]–CH₂–CH=CH₂ | 20 |
| (1-1106) | CH₂=CH–[Cy]–[Cy]–C₅H₁₁ | 10 |
| (1-1107) | CH₂=CH–CH₂–[Cy]–[Cy]–C₃H₇ | 10 |
| (1-1108) | CH₂=CH–[Cy]–[Cy]–[Ph]–CH₃ | 10 |
| (1-1109) | CH₂=CH–CH₂–[Cy]–[Cy]–[Ph]–CH₃ | 5 |
| (1-1110) | CH₂=CH–CH₂–[Cy]–[Cy]–[Ph(3,4-F₂)] | 10 |
| (1-1111) | CH₃–CH=CH–CH₂–[Ph(2,6-F₂)]–COO–[Ph(3-F)]–CN | 5 |

Characteristic values of the aforementioned nematic liquid crystal composition (1-10) are shown in the following.

| | |
|---|---|
| $T_{N-I}$ | 88.6° C. |
| $T_{\to N}$ | −70° C. |
| $\Delta\epsilon$ | 8.6 |
| $\Delta n$ | 0.168 |

Threshold voltage when TN-LCD is constructed (Vth): 2.01 V (8μ)

Sharpness when TN-LCD is constructed (γ): 1.15

Threshold voltage when STN-LCD is constructed (Vth): 2.27 V

Sharpness when STN-LCD is constructed (γ): 1.028

Nematic liquid crystal composition (1-12)
(% by weight)
(1-1201) 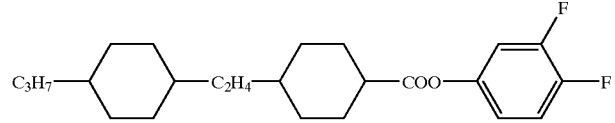 10
(1-1202) 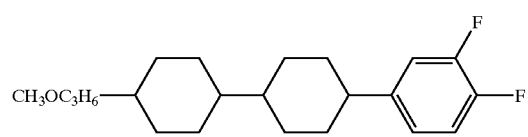 7
(1-1203) 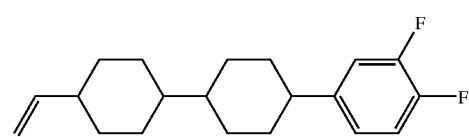 20
(1-1204) 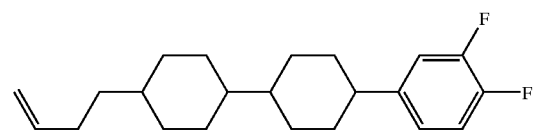 20
(1-1205) 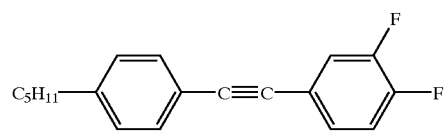 4
(1-1206) 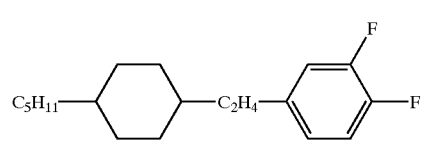 4
(1-1207) 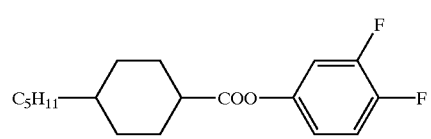 4
(1-1208) 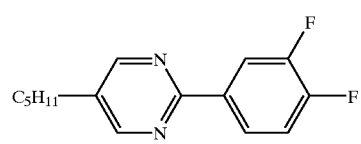 4
(1-1209) 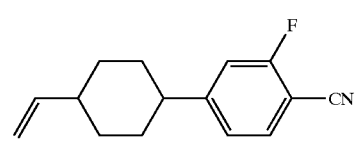 4
(1-1210) 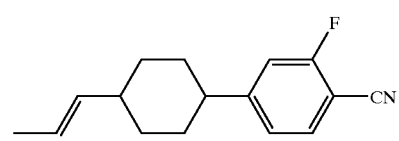 5

-continued
Nematic liquid crystal composition (1-12)
| | | (% by weight) |
|---|---|---|
| (1-1211) | 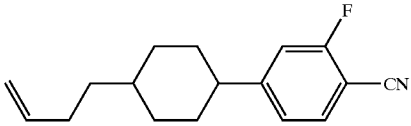 | 5 |
| (1-1212) | 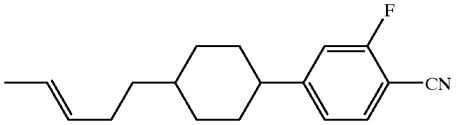 | 5 |
| (1-1213) | 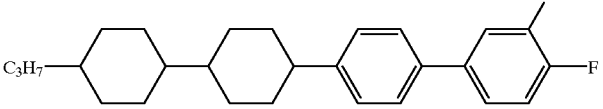 | 3 |
| (1-1214) | 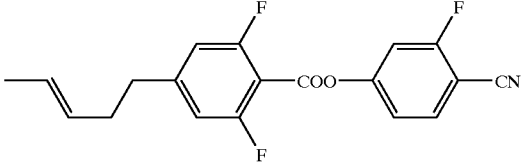 | 5 |
Characteristic values of the aforementioned nematic liquid crystal composition (1-11) are shown in the following.
| | |
|---|---|
| $T_{N-I}$ | 70.1° C. |
| $T_{\to N}$ | −70° C. |
| $\Delta\epsilon$ | 7.1 |
| $\Delta n$ | 0.084 |
Threshold voltage when TN-LCD is constructed (Vth): 1.66 V (8μ)
Sharpness when TN-LCD is constructed (γ): 1.17
Nematic liquid crystal composition (1-13)
| | | (% by weight) |
|---|---|---|
| (1-1301) | 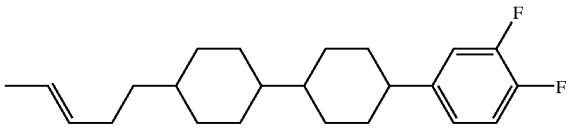 | 10 |
| (1-1302) | 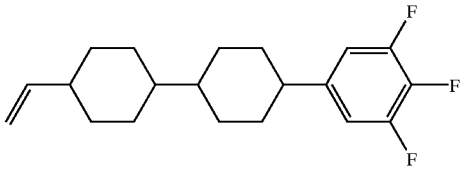 | 10 |

-continued

Nematic liquid crystal composition (1-13)

| | | (% by weight) |
|---|---|---|
| (1-1303) | allyl-cyclohexyl(D4)-cyclohexyl-(3,4,5-trifluorophenyl) | 10 |
| (1-1304) | C₃H₇-cyclohexyl-phenyl-CN | 10 |
| (1-1305) | butenyl-cyclohexyl-phenyl-CN | 10 |
| (1-1306) | vinyl-cyclohexyl-cyclohexyl-C₅H₁₁ | 10 |
| (1-1307) | vinyl-cyclohexyl-cyclohexyl-phenyl-CH₃ | 10 |
| (1-1308) | vinyl-cyclohexyl-cyclohexyl(D3)-phenyl-OCF₃ | 10 |
| (1-1309) | C₃H₇-cyclohexyl(D4)-cyclohexyl-phenyl-OCF₃ | 10 |
| (1-1310) | butenyl-phenyl-COO-phenyl-CN | 5 |
| (1-1311) | butenyl-phenyl-COO-(3-fluorophenyl)-CN | 5 |

| Nematic liquid crystal composition (1-14) | |
|---|---|
| | (% by weight) |
| (1-1401) [structure: C2H5-cyclohexyl-cyclohexyl(D4)-C2H4-trifluorophenyl] | 5 |
| (1-1402) [structure: C3H7-cyclohexyl-cyclohexyl(D4)-C2H4-trifluorophenyl] | 10 |
| (1-1403) [structure: C2H5-cyclohexyl-cyclohexyl(D3)-trifluorophenyl] | 5 |
| (1-1404) [structure: C3H7-cyclohexyl(D4)-cyclohexyl-trifluorophenyl] | 10 |
| (1-1405) [structure: C3H7-cyclohexyl(D4)-cyclohexyl-difluorophenyl] | 10 |
| (1-1406) [structure: vinyl-cyclohexyl-cyclohexyl-C5H11] | 10 |
| (1-1407) [structure: butenyl-cyclohexyl-cyclohexyl-butenyl] | 10 |
| (1-1408) [structure: vinyl-cyclohexyl-cyclohexyl-phenyl-CH3] | 10 |
| (1-1409) [structure: butenyl-cyclohexyl-cyclohexyl-phenyl-CH3] | 10 |
| (1-1410) [structure: C3H7-cyclohexyl-C2H4-phenyl-cyclohexyl-C5H11] | 10 |
| (1-1411) [structure: butenyl-phenyl-COO-phenyl-CN] | 5 |

-continued
Nematic liquid crystal composition (1-14)
(% by weight)
(1-412) 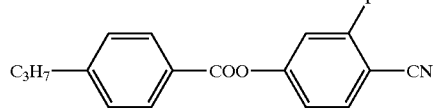 5
Characteristic values of the aforementioned nematic liquid crystal composition (1-14) are shown in the following.
| | |
|---|---|
| $T_{N-1}$ | 97.1° C. |
| $T_{\to N}$ | −70° C. |
| $\Delta\epsilon$ | 7.6 |
| $\Delta n$ | 0.058 |
Threshold voltage when TN-LCD is constructed (Vth): 1.78 V (8μ)
Sharpness when TN-LCD is constructed (γ): 1.15
Nematic liquid crystal composition (1-15)
(% by weight)
(1-1501) 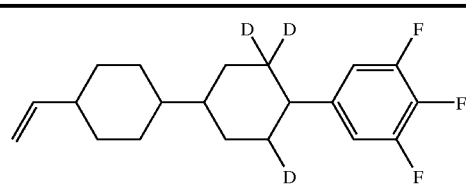 10
(1-1502) 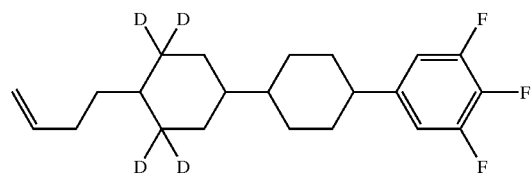 10
(1-1503) 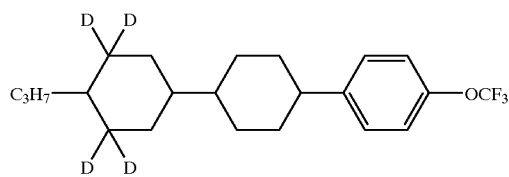 10
(1-1504) 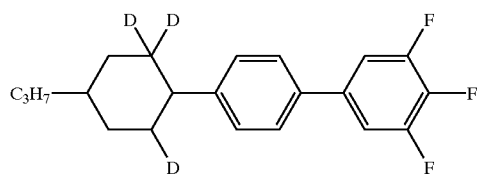 5
(1-1505) 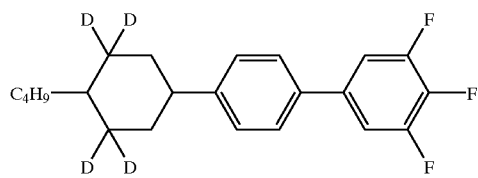 5

-continued

Nematic liquid crystal composition (1-15)

(% by weight)

(1-1506) C5H11-[cyclohexane-D,D,D,D]-[phenyl]-[phenyl-3,4,5-triF] 15

(1-1507) C3H7-[cyclohexane-D,D,D,D]-C2H4-[cyclohexyl]-[cyclohexyl]-[phenyl-3,4,5-triF] 5

(1-1508) CH2=CHCH2CH2-[cyclohexyl]-[cyclohexyl]-CH2CH2CH=CH2 10

(1-1509) CH2=CH-[cyclohexyl]-[cyclohexyl]-[phenyl]-CH3 10

(1-1510) CH2=CHCH2CH2-[phenyl]-C≡C-[phenyl]-CH2CH2CH=CH2 10

(1-1511) CH2=CHCH2CH2-[phenyl]-COO-[phenyl-3-F]-CN 5

(1-1512) CH3CH=CHCH2-[phenyl-2,6-diF]-COO-[phenyl-3-F]-CN 5

Nematic liquid crystal composition (1-16)

(% by weight)

(1-1601) C3H7-[cyclohexane-D,D,D]-[phenyl]-C≡C-[phenyl-3,4,5-triF] 10

-continued

Nematic liquid crystal composition (1-16)

(% by weight)

(1-1602) 10

(1-1603) 13

(1-1604) 17

(1-1605) 10

(1-1606) 10

(1-1607) 10

(1-1608) 10

(1-1609) 5

(1-1610) 5

Liquid crystal display systems are currently under a state of severely heated price competition. In view of this, a problem to be resolved for liquid crystal materials is how to optimize their display characteristics for various applications simply and easily, and systematized liquid crystal materials, such as a two bottle system comprising two types of liquid crystal materials or a four two bottle system comprising four types of liquid crystal materials, are expected. The typical characteristics are threshold voltage, birefringence and nematic phase-isotropic liquid phase transition temperature. For example, when a two bottle system which comprises a liquid crystal material having a high threshold voltage and a liquid crystal material having a low threshold voltage, but the other characteristics are equivalent, is used, quicker and more inexpensive results can be achieved by optionally formulating these two liquid crystal materials without restriction by driving electronic parts and the like to be used. The present invention is also useful from such a point of view, and compositions prepared from the nematic liquid crystal materials (1-01) to (1-16) and partially replaced materials thereof can be used by optionally mixing them. As a matter of course, such application methods can be carried out including those which are described in the following examples.

EXAMPLES

Examples of the present invention are given below by way of illustration and not by way of limitation.

In this connection, measurement of the phase transition temperature was carried out by jointly using a polarizing microscope equipped with a temperature controlling stage and a differential scanning calorimeter (DSC). Also, the structure of each compound was confirmed by magnetic resonance spectrum ($^1$H-NMR, $^{13}$C-NMR or $^{19}$F-NMR), infrared resonance spectrum (IR), mass spectrum (MS) and the like means.

In the following, "%" means "% by weight".

Example 1

Synthesis of 2,6-Difluoro-4-(3-butenyl)benzoic Acid

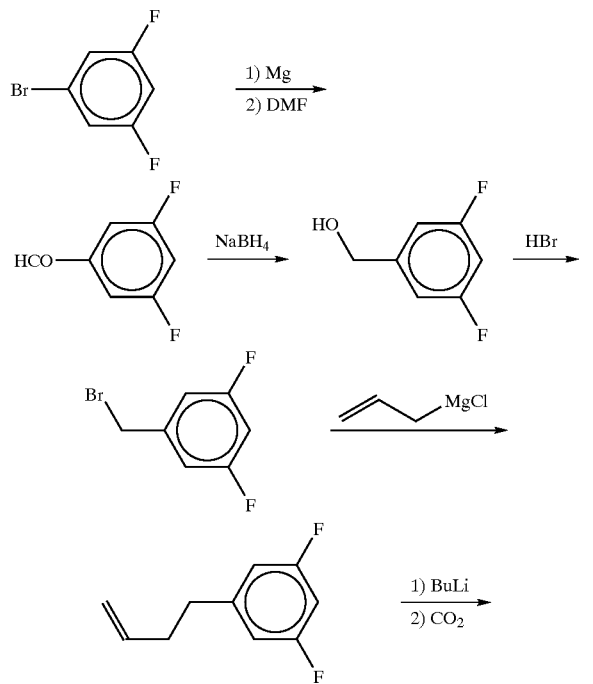

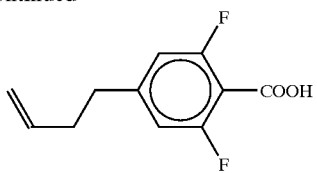

-continued (1-a) Synthesis of 3,5-Difluorobenzaldehyde

A 28 g portion of magnesium turnings was suspended in 60 ml of tetrahydrofuran (THF) to which was subsequently added dropwise 800 ml of THF solution containing 200 g of 3,5-difluoro-1-bromobenzene at such a rate that the solvent was gently refluxed. After the dropwise addition, the mixture was stirred at room temperature for 1 hour and then 91 g of N,N-dimethylformamide (DMF) was added dropwise thereto. After the dropwise addition, this was further stirred at room temperature for 1 hour, mixed with 1,000 ml of 10% hydrochloric acid and again stirred for 1 hour. This was extracted with 1,000 ml of ethyl acetate, washed twice with saturated brine and then dried with anhydrous sodium sulfate. By evaporating the solvent, 125 g of 3,5-difluorobenzaldehyde was obtained.

(1-b) Synthesis of 3,5-Difluorobenzyl Alcohol

A 20 g portion of sodium borohydride was suspended (partially dissolved) in 90 ml of ethanol, and 380 ml of ethanol solution containing 125 g of 3,5-difluorobenzaldehyde to the suspension which was cooled in an ice bath. After the dropwise addition, this was stirred for 1 hour, the solvent was evaporated and the resulting residue was mixed with 400 ml of water. This was extracted with 700 ml of ethyl acetate, washed with water and saturated brine in that order and then dried with anhydrous sodium sulfate. By evaporating the solvent, 120 g of 3,5-difluorobenzyl alcohol was obtained.

(1-c) Synthesis of 3,5-Difluorobenzyl Bromide

A 120 ml portion of 48% hydrobromic acid was added to 120 g of 3,5-difluorobenzyl alcohol. At room temperature, 120 ml of sulfuric acid was added dropwise thereto, and the mixture after the dropwise addition was stirred for 3 hours. The reaction solution was poured onto crashed ice, extracted with 600 ml of hexane, washed with water and saturated brine in that order and then dried with anhydrous sodium sulfate. By evaporating the solvent, 176 g of 3,5-difluorobenzyl bromide was obtained.

(1-d) Synthesis of 3,5-Difluoro-1-(3-butenyl)benzene

A 176 g portion of 3,5-difluorobenzyl bromide was dissolved in 300 ml of THF to which was subsequently added dropwise 450 ml of allyl magnesium chloride THF solution (2 mol/l) at room temperature. This was stirred for 1 hour and then mixed with 300 ml of water. This was extracted with 800 ml of hexane, washed twice with saturated brine and then dried with anhydrous sodium sulfate. After evaporation of the solvent, the resulting residue was distilled (79–82° C./20 mmHg) to obtain 104 g of 3,5-difluoro-1-(3-butenyl)benzene.

(1-e) Synthesis of 2,6-Difluoro-4-(3-butenyl)benzoic Acid

A 50 g portion of 3,5-difluoro-1-(3-butenyl)benzene was dissolved in 200 ml of THF, and the solution was cooled to −60° C. A 190 ml portion of n-butyl lithium hexane solution (1.59 mol/l) was added dropwise thereto at such a rate that the solution was kept at −40° C. or lower, and the mixture after the dropwise addition was stirred for 1 hour. Carbon dioxide was bubbled into the resulting solution at such a rate that the reaction system was kept at −40° C. or lower. When exothermic reaction was calmed down, this was stirred for additional 1 hour and returned to room temperature. This was mixed with 130 ml of 10% hydrochloric acid, extracted with 400 ml of ethyl acetate, washed twice with saturated brine and then dried with anhydrous sodium sulfate. By evaporating the solvent, 62 g of 2,6-difluoro-4-(3-butenyl) benzoic acid was obtained.

Example 2

Synthesis of 2-Fluoro-4-(3-pentenyl)benzoic Acid

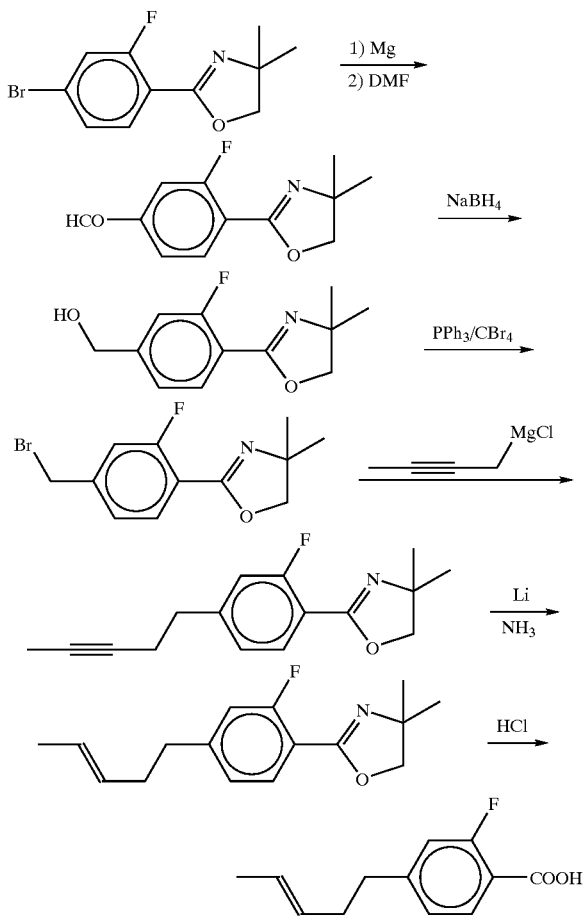

(2-a) Synthesis of 2-(4-Formyl-2-fluoro)phenyl-4,4-dimethyl-1,3-oxazolidine

A Grignard reagent was prepared by allowing 2-(4-bromo-2-fluoro)phenyl-4,4-dimethyl-1,3-oxazolidine (this was synthesized by treating 4-bromo-2-fluorobenzoic acid with thionyl chloride to convert it into acid chloride which was subsequently allowed to react with 2-amino-2-methyl-1-propanol and then with thionyl chloride) to react with magnesium in THF. This was allowed to react with DMF in the same manner as described in the aforementioned step (1-a) to obtain 2-(4-formyl-2-fluoro)phenyl-4,4-dimethyl-1,3-oxazolidine in the form of white crystals.

(2-b) Synthesis of 2-(4-Hydroxymethyl-2-fluoro)phenyl-4,4-dimethyl-1,3-oxazolidine By reducing 2-(4-formyl-2-fluoro)phenyl-4,4-dimethyl-1,3-oxazolidine obtained in the above step (2-a) with sodium borohydride in the same manner as described in the aforementioned step (1-b), 2-(4-hydroxymethyl-2-fluoro)phenyl-4,4-dimethyl-1,3-oxazolidine was obtained in the form of white crystals.

(2-c) Synthesis of 2-(4-Bromomethyl-2-fluoro)phenyl-4,4-dimethyl-1,3-oxazolidine 2-(4-Hydroxymethyl-2-fluoro)phenyl-4,4-dimethyl-1,3-oxazolidine obtained in the above step (2-b) was dissolved in a mixed solution of THF and methane tetrabromide, and the solution was mixed with triphenylphosphine and heated under reflux for 1 hour. After cooling, this was mixed with hexane and stirred; and the thus precipitated triphenylphosphine was removed by filtration. After evaporation of the solvent, the resulting residue was recrystallized from hexane to obtain 2-(4-bromomethyl-2-fluoro)phenyl-4,4-dimethyl-1,3-oxazolidine in the form of white crystals.

(2-d) Synthesis of 2-[4-(3-Pentyne-1-yl)-2-fluoro]phenyl-4,4-dimethyl-1,3-oxazolidine A Grignard reagent prepared from 1-chloro-2-butyne was added dropwise to THF solution of 2-(4-bromomethyl-2-fluoro)phenyl-4,4-dimethyl-1,3-oxazolidine. Thereafter, in the same manner as described in the aforementioned step (1-d), 2-[4-(3-pentyne-1-yl)-2-fluoro]phenyl-4,4-dimethyl-1,3-oxazolidine was obtained in the form of white crystals.

(2-e) Synthesis of 2-[4-(trans-3-Penten-1-yl)-2-fluoro]phenyl-4,4-dimethyl-1,3-oxazolidine Lithium was dissolved in liquid ammonia cooled at −40° C., and to this solution was added dropwise THF solution of 2-[4-(3-pentyne-1-yl)-2-fluoro]phenyl-4,4-dimethyl-1,3-oxazolidine obtained in the above step (2-d) and t-butyl alcohol. This was mixed with ammonium chloride and then ammonia was evaporated. The resulting residue was dissolved in toluene and washed with water and then the solvent was evaporated to obtain 2-[trans-4-(3-penten-1-yl)-2-fluoro]phenyl-4,4-di ethyl-1,3-oxazolidine in the form of white crystals.

(2-f) Synthesis of 2-Fluoro-4-(trans-3-penten-1-yl)benzoic Acid

2-[4-(Trans-3-penten-1-yl)-2-fluoro]phenyl-4,4-dimethyl-1,3-oxazolidine obtained in the above step (2-e) was dissolved in ethanol, and the solution was mixed with 10% hydrochloric acid and stirred at room temperature for 4 hours. After evaporation of the greater part of ethanol, the resulting residue was extracted with toluene and the thus obtained crude product was recrystallized from hexane to obtain 2-fluoro-4-(trans-3-penten-1-yl)benzoic acid in the form of white crystals.

Example 3

Synthesis of 3-Fluoro-4-cyanophenyl 2,6-Difluoro-4-(3-buten-1-yl)benzoate (I)-1

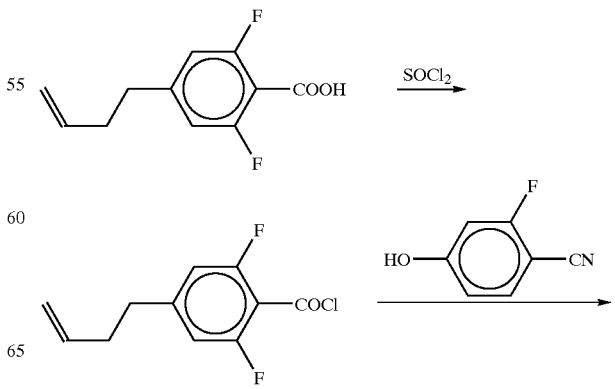

-continued

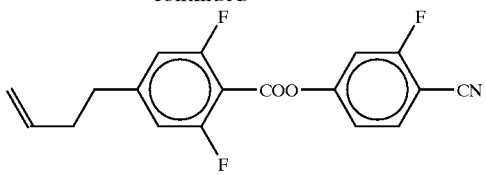

A 15 g portion of 2,6-difluoro-4-(3-buten-1-yl)benzoic acid obtained in Example 1 was dissolved in 45 ml of dichloromethane, and the solution was mixed with 13 g of thionyl chloride and 0.1 ml of pyridine and heated under reflux for 6 hours. The acid chloride obtained by evaporation of the solvent and 10 g of 3-fluoro-4-cyanophenol were dissolved in 60 ml of dichloromethane, and 9 g of pyridine was added dropwise to the resulting solution at room temperature. After the dropwise addition, this was stirred for 1 hour and then mixed with 60 ml of 10% hydrochloric acid. The resulting organic layer was separated, washed with water, saturated sodium bicarbonate solution, water and saturated brine in that order and then dried with anhydrous sodium sulfate. After evaporation of the solvent, the resulting residue was purified by a silica gel column chromatography (toluene) and then recrystallized from methanol to obtain 13 g of 3-fluoro-4-cyanophenyl 2,6-difluoro-4-(3-buten-1-yl)benzoate.

The following compounds are obtained in the same manner.

4-Cyanophenyl 2,6-difluoro-4-(3-buten-1-yl)benzoate 3,5-Difluoro-4-cyanophenyl 2,6-difluoro-4-(3-buten-1-yl)benzoate 4-Cyanophenyl 2,6-difluoro-4-(trans-3-penten-1-yl)benzoate 3-Fluoro-4-cyanophenyl 2,6-difluoro-4-(trans-3-penten-1-yl)benzoate 3,5-Difluoro-4-cyanophenyl 2,6-difluoro-4-(trans-3-penten-1-yl)benzoate 4-Cyanophenyl 2,6-difluoro-4-(trans-3-hexen-1-yl)benzoate 3-Fluoro-4-cyanophenyl 2,6-difluoro-4-(trans-3-hexen-1-yl)benzoate 3,5-Difluoro-4-cyanophenyl 2,6-difluoro-4-(trans-3-hexen-1-yl)benzoate Example 4

Synthesis of 3,5-Difluoro-4-cyanophenyl 2-Fluoro-4-(trans-3-penten-1-yl)benzoate (I)-2

3,5-Difluoro-4-cyanophenyl 2-fluoro-4-(trans-3-penten-1-yl)benzoate (I)-2 was obtained from 2-fluoro-4-(trans-3-penten-1-yl)benzoic acid obtained in Example 2 in the same manner as described in Example 3.

The following compounds are obtained in the same manner.

4-Cyanophenyl 2-fluoro-4-(trans-3-penten-1-yl)benzoate

3-Fluoro-4-cyanophenyl 2-fluoro-4-(trans-3-penten-1-yl)benzoate

4-Cyanophenyl 2-fluoro-4-(3-buten-1-yl)benzoate

3-Fluoro-4-cyanophenyl 2-fluoro-4-(3-buten-1-yl)benzoate 3,5-Difluoro-4-cyanophenyl 2-fluoro-4-(3-buten-1-yl)benzoate 4-Cyanophenyl 2-fluoro-4-(trans-3-hexen-1-yl)benzoate 3-Fluoro-4-cyanophenyl 2-fluoro-4-(trans-3-hexen-1-yl)benzoate 3,5-Difluoro-4-cyanophenyl 2-fluoro-4-(trans-3-hexen-1-yl)benzoate.

The following describes compositions of the present invention in detail. In the compositions of the following examples, —$(CH_2)_2$— and —$C_2H_4$— or —$(CH_2)_4$— and —$C_4H_8$— are identical with each other.

In the examples, physical property characteristics of liquid crystal compositions and display characteristics of liquid crystal displays constituting TN-LCD are as follows.

$T_{N-I}$: nematic phase-isotropic liquid phase transition temperature (° C.)

$T_{\to N}$: solid phase- or smectic phase-nematic phase transition temperature (° C.)

$\Delta\epsilon$: dielectric anisotropy at 20° C.

$\Delta n$: birefringence at 20° C.

$\eta$: viscosity at 20° C. (c.p.)

Vth: threshold voltage at 20° C. when TN-LCD is constructed (V)

$\gamma$: ratio of sharpness, saturation voltage (Vsat) to Vth at 20° C.

$\tau r = \tau d$: time when both items become equal at 20° C., wherein $\tau r$ is rise time from 0 V when a predetermined voltage is applied, and $\tau d$ is decay time when the applied voltage is released.

Chemical stability of compositions was evaluated by putting 2 g of each liquid crystal composition into an ampoule tube, sealing the tube after vacuum degassing and subsequent nitrogen replacement and then carrying out 1 hour of heating acceleration test at 150° C. Each of the liquid crystal compositions was measured for its specific resistance before the test, specific resistance after the heating acceleration test, voltage holding ratio before the test and voltage holding ratio after the heating acceleration test.

In this connection, one or a plurality of the compounds shown in the Examples can be used by replacing them by certain compounds of the general formulae (I-1) to (III-4) depending on desired purpose or use, and illustrative compounds in such a case are represented by the following forms.

Liquid Crystal Component A

A case of general formula (I-10) Compound (2-11): side chain group (I-ah) basic structure (I-10)

A case of general formula (I-13) Compound (2-12): side chain group (I-ah) basic structure (I-13)

A case of general formula (I-16) Compound (2-13): side chain group (I-ah) basic structure (I-16)

Liquid Crystal Component B

A case of general formula (II-1) Compound (2-21): side chain group (II-5a) basic structure (II-1a) polar group (II-6a)

A case of general formula (II-2) Compound (2-22): side chain group (II-5a) basic structure (II-2a) polar group (II-6a)

A case of general formula (II-3) Compound (2-23): side chain group (II-5a) basic structure (II-3a) polar group (II-6a)

A case of general formula (II-4) Compound (2-24): side chain group (II-5a) basic structure (II-1a) polar group (II-6a)

Liquid Crystal Component C

A case of general formula (III-1) Compound (2-31): side chain group (III-5b) basic structure (III-1a) side chain group (III-5b)

A case of general formula (III-2) Compound (2-32): side chain group (III-5b) basic structure (III-2a) side chain group (III-5b)

A case of general formula (III-3) Compound (2-33): side chain group (III-5b) basic structure (III-3a) side chain group (III-5b)

A case of general formula (III-4) Compound (2-34): side chain group (III-5b) basic structure (III-4a) side chain group (III-5b)

Definition of Compounds

Liquid crystal component A

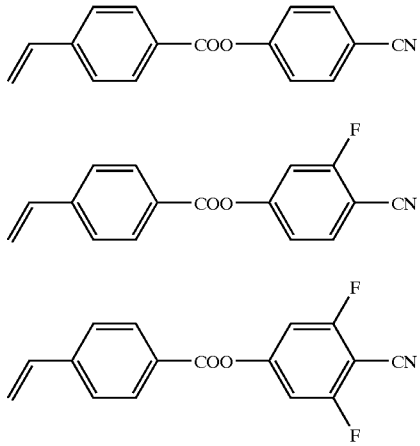

(2-11)

(2-12)

(2-13)

Liquid crystal component B

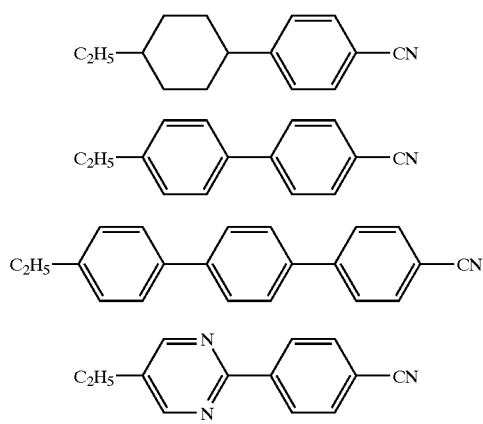

(2-21)

(2-22)

(2-23)

(2-24)

Liquid crystal component C

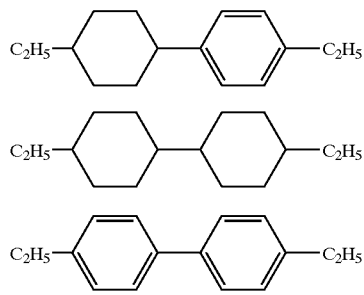

(2-31)

(2-32)

(2-33)

-continued

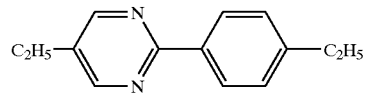

(2-34)

Example 5 and Comparative Example 1

A host liquid crystal composition (H) of the following composition

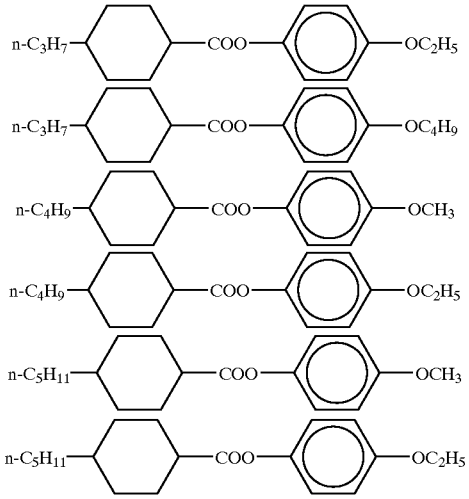

(mixture of equivalent amounts) comprising compounds of the present invention represented by the general formula (III-1b) was prepared. This composition corresponds to the liquid crystal component C of the present invention. Various characteristics of this composition were measured. The results are as follows.

| | |
|---|---|
| $T_{N-I}$ | 72.5° C. |
| $T_{\to N}$ | +17° C. |
| $\Delta\epsilon$ | −1.3 |
| $\Delta n$ | 0.085 |
| Vth | — |

A liquid crystal composition (H-A) for comparison use comprising 90% of the host liquid crystal (H) and 10% of a -conventionally used compound of the following formula (A).

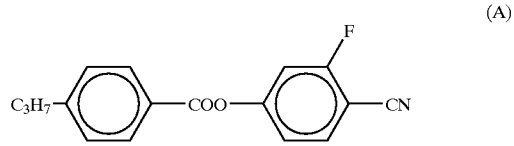

(A)

was prepared and its various characteristics were measured.

The results are as follows.

| | |
|---|---|
| $T_{N-I}$ | 65.5° C. |
| $\Delta\epsilon$ | 3.0 |
| $\Delta n$ | 0.093 |
| Vth | 2.38 V |

Next, a liquid crystal composition (H-1) was prepared by adding the same amount (10%) of the compound (I)-1 of the present invention shown in Table 1 to the host liquid crystal (H), and various characteristics of the resulting composition were measured. The results are as follows.

| | |
|---|---|
| $T_{N-I}$ | 62.0° C. |
| $\Delta\epsilon$ | 2.6 |
| $\Delta n$ | 0.088 |
| Vth | 1.96 V |

The composition (H-1) of the present invention showed a $T_{N-I}$ value of 62.0° C. which was slightly lower than that of the composition (H-A). Also, it can be seen that its threshold voltage (Vth) was reduced by a factor of 0.4 V or more regardless of the 10% or more reduction in its dielectric anisotropy ($\Delta\epsilon$). On the other hand, the response was not slowed. Next, the composition (H-1) was allowed to stand at 0° C., but precipitation of crystals and phase separation were not observed even after one week of standing. In addition, when it was crystallized by allowing it to stand at −40° C., its melting point was measured to be 4° C.

Comparative Example 2

A liquid crystal composition (H-B) for comparison use was prepared by adding the same amount (10%) of a conventionally used compound represented by the following formula (B)

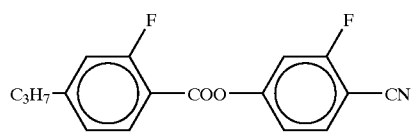

(B)

to the host liquid crystal (H) in the same manner as described in Example 5 and Comparative Example 1, and various characteristics of the resulting composition were measured. The results are as follows.

| | |
|---|---|
| $T_{N-I}$ | 64.1° C. |
| $\Delta\epsilon$ | 3.4 |
| $\Delta n$ | 0.091 |
| Vth | 2.30 V |

The $T_{N-I}$ value of (H-B) was 64.1° C. which was slightly lower than the case of (H-A) but slightly higher than the case of (H-1). Its threshold voltage was reduced only slightly in comparison with (H-A) and far beyond the case of (H-1).

Comparative Example 3

A liquid crystal composition (H-C) for comparison use was prepared by adding the same amount (10%) of a conventionally used compound represented by the following formula (C)

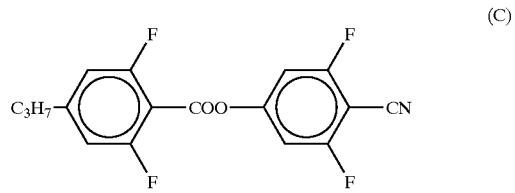

(C)

to the host liquid crystal (H) in the same manner as described above, and various characteristics of the resulting composition were measured. The results are as follows.

| | |
|---|---|
| $T_{N-I}$ | 63.0° C. |
| $\Delta\epsilon$ | 3.5 |
| $\Delta n$ | 0.089 |
| Vth | 2.15 V |

The $T_{N-I}$ value of (H-C) was 63.0° C. which was almost equivalent to the case of (H-1). Also, dielectric anisotropy of (H-C) was considerably large and, because of this, its threshold voltage was markedly improved in comparison with (H-A) and (H-B). However, regardless of its larger dielectric anisotropy in comparison with (H-1), its threshold voltage is higher by a factor of about 0.2 V so that its reducing effect is far beyond the target. In addition, when the composition (H-C) was allowed to stand at 0° C., it was crystallized within 3 days, and its melting point when measured was a high value of 18° C.

On the basis of the above results, it is evident that the compound of general formula (I) of the present invention has excellent threshold voltage reducing effect and also is excellent in terms of miscibility, in comparison with the conventional high p type phenyl benzoate derivatives.

Example 6

Next, a liquid crystal composition (H-2) was prepared by adding the same amount (10%) of the compound (I)-2 of the present invention shown in Table 1 to the host liquid crystal (H), and various characteristics of the resulting composition were measured. The results are as follows.

| | |
|---|---|
| $T_{N-I}$ | 66.0° C. |
| $\Delta\epsilon$ | 3.7 |
| $\Delta n$ | 0.091 |
| Vth | 1.89 V |

The composition (H-2) showed a $T_{N-I}$ value of 62.5° C. which was slightly higher than that of the composition (H-1). It can be seen that its dielectric anisotropy ($\Delta\epsilon$) is larger than that of (H-1) and its threshold voltage (Vth) was sharply reduced. Also, when the composition (H-2) was allowed to stand at 0C, precipitation of crystals and phase separation were not observed even after one week of standing.

Example 7 and Comparative Example 4

Liquid crystal compositions composed of a mixture of the above-described host liquid crystal H and a compound of formula (I)-1 or (I)-3 shown below which corresponds to the liquid crystal component A as the essential component of the present invention were prepared. Further, liquid crystal compositions composed of a mixture of the above-described host liquid crystal H and a compound of a formula (D) or (E) shown below were also prepared for comparison use.

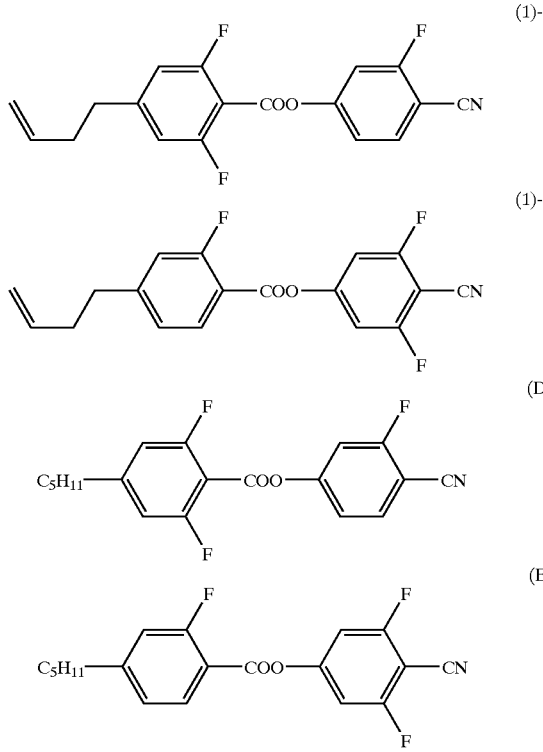

With regard to the liquid crystal composition which contains the conpound of formula (I)-1, five liquid crystal compositions were prepared by adjusting the content of the compound of formula (I)-1 to 10% by weight, 15% by weight, 20% by weight, 25% by weight or 30% by weight. With regard to the liquid crystal composition which contains the compound of formula (D), liquid crystal compositions were prepared in the same manner as the case of the compound of formula (I)-1. With regard to the liquid crystal composition which contains the compound of formula (I)-3, three liquid crystal compositions were prepared by adjusting the content of the compound of formula (I)-3 to 10% by weight, 15% by weight or 20% by weight. With regard to the liquid crystal composition which contains the compound of formula (E), liquid crystal compositions were prepared in the same manner as the case of the compound of formula (I)-3.

Using each of the thus prepared liquid crystal compositions, viscosity at 20° C. and threshold voltage were measured. The results are shown in FIG. 1.

As is evident from the results shown in FIG. 1, it was confirmed that the nematic liquid crystal composition of the present invention obtained by adding the compound of formula (I)-1 or (I)-3, which corresponds to the liquid crystal component A as the essential component of the nematic liquid crystal composition of the present invention, to the host liquid crystal (H) composed of the liquid crystal component C, has smaller viscosity against driving voltage when compared with the comparative liquid crystal composition which contains the compound (D) or (E) and is therefore different from the composition of the present invention.

This effect is apt to be achieved when the liquid crystal component C composed of two or more compounds having a dielectric anisotropy of from −10 to 2 has smaller viscosity, and it is desirable that the liquid crystal component C alone has a viscosity of 25 c.p. or less, preferably 15 c.p. or less, more preferably 10 c.p. or less, most preferably 8 c.p. or less. Particularly, when compounds of general formulae (I-19) to (I-18) having alkenyl groups as their side chain groups are used as the liquid crystal component A, it is desirable for improving viscosity to use as the liquid crystal component C compounds of general formulae (III-1a) to (III-1d), (III-2a), (III-2f), (III-3a) and (III-3h), or as particularly illustrative compounds, compounds of the subgroups (III-ai) to (III-av), (III-bi) to (II-biii) and (III-ci) to (III-ciii). By the use of such compounds, viscosity of the nematic liquid crystal composition containing compounds of groups A4 to A6 is further improved.

Example 8

A nematic liquid crystal composition (3-01) comprising the following compounds

-continued

| | (% by weight) |
|---|---|
| (3-0103) [structure: 4-(3-butenyl)-2-fluorophenyl 3-fluoro-4-cyanophenyl ester, -COO-] | 5 |
| (3-0104) [structure: C₅H₁₁-pyrimidine-C₆H₄-CN] | 3 |
| (3-0105) [structure: C₃H₇-C₆H₄-C≡C-C₆H₄-OCH₃] | 9 |
| (3-0106) [structure: C₄H₉-C₆H₄-C≡C-C₆H₄-OC₂H₅] | 9 |
| (3-0107) [structure: C₅H₁₁-C₆H₄-C≡C-C₆H₄-OCH₃] | 8 |
| (3-0108) [structure: C₅H₁₁-C₆H₄-C≡C-C₆H₄-OC₂H₅] | 8 |
| (3-0109) [structure: C₃H₇-Cy-C₆H₄-OC₂H₅] | 5 |
| (3-0110) [structure: C₃H₇-Cy-C₆H₄-C≡C-C₆H₄-C₂H₅] | 4 |
| (3-0111) [structure: C₄H₉-Cy-C₆H₄-C≡C-C₆H₄-CH₃] | 4 |
| (3-0112) [structure: vinyl-Cy-Cy-C₅H₁₁] | 10 |
| (3-0113) [structure: 3-butenyl-Cy-Cy-C₃H₇] | 11 |
| (3-0114) [structure: vinyl-Cy-Cy-C₆H₄-CH₃] | 8 |
| (3-0115) [structure: 3-butenyl-Cy-Cy-C₆H₄-CH₃] | 9 | was prepared and various characteristics of the composition were measured. The results are as follows.

| | |
|---|---|
| $T_{N-I}$ | 85.2° C. |
| $T_{\to N}$ | −30.0° C. |
| Vth | 1.61 V |
| Δε | 7.2 |
| Δn | 0.169 |
| η | 20.0 c.p. |

Specific resistance before the test: $8.4 \times 10^{12}$ Ω·cm

Specific resistance after heating acceleration test: $4.0 \times 10^{12}$ Ω·cm

Since this nematic liquid crystal composition has high specific resistance after the heating acceleration test, it can be understood that it is stable against heat. Also, when twisted nematic and super twisted nematic liquid crystal display systems were prepared using this composition as a constituting material, it was confirmed that they were excellent display systems which do not generate flicker.

In addition, a mixed liquid crystal composition was prepared by adding a chiral substance "S-811" (manufactured by Merck) to this nematic liquid crystal composition. On the other hand, a cell for STN-LCD use having a twist angle of 220 degree was prepared by effecting formation of the orientation film through the rubbing of an organic film of "Sun Ever 610" (manufactured by Nissan Chemical Industries) on the facing transparent flat electrode. The aforementioned mixed liquid crystal composition was injected into the thus prepared cell to construct a liquid crystal display system, and its display characteristics were measured. As the result, a liquid crystal display system was obtained which showed STN-LCD display characteristics having particularly excellent effects in terms of low threshold voltage, high multiplexing properties, improved flicker and crosstalk phenomena on the display screen, quick response and viewing angle characteristics having small parallax.

In this connection, the chiral substance was added in such an amount that natural helical pitch P of the mixed liquid crystal composition and cell thickness d of the display cell became Δn·d=0.85 and d/P=0.53 by the addition of the chiral substance.

In addition, when a TN-LCD having a cell thickness d of 3.0 μm was constructed and its display characteristics were measured, its threshold voltage was 1.39 V and response time was 1.2 msec. A liquid crystal display system showing TN-LCD display characteristics was obtained.

A nematic liquid crystal composition (3-01-01) is prepared by changing the compound (3-0103) of the nematic liquid crystal composition shown in this example to a compound: side chain group (I-al) basic structure (I-16). Nematic liquid crystal compositions prepared in this manner are shown in the following as "Composition (3-01-01)= compound (3-0103)→compound: side chain group (I-al) basic structure (I-16)".

Composition (3-01-02)=compound (3-0103)→compound: side chain group (I-al) basic structure (I-16) polar group Composition (3-01-03)=compound (3-0103)→compound: side chain group (I-am) basic structure (I-16) polar group Composition (3-01-04)=compound (3-0103)→compound: side chain group (I-an) basic structure (I-16) polar group Composition (3-01-05)=compound (3-0103)→compound: side chain group (I-al) basic structure (I-17) polar group Composition (3-01-06)=compound (3-0103)→compound: side chain group (I-am) basic structure (I-18) polar group Composition (3-01-07)=compound (3-0103)→compound: side chain group (I-an) basic structure (I-19) polar group Similar to this example, these nematic liquid crystal compositions (3-01-01) to (3-01-07) showed excellent display characteristics.

Example 9

A nematic liquid crystal composition (3-02) comprising the following compounds (3-0201)

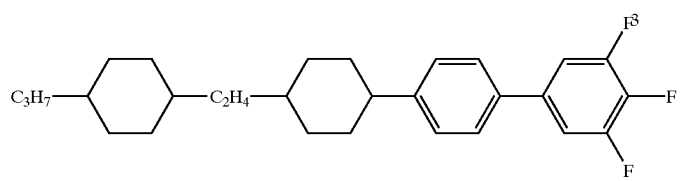

(3-0202) 5

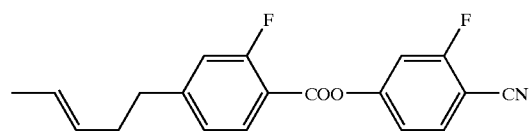

(3-0203) 8

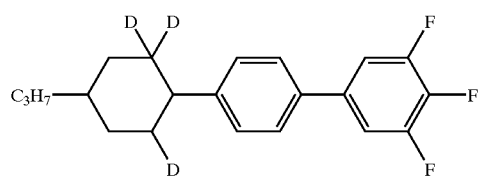

-continued

| | | |
|---|---|---|
| (3-0204) | C3H7—[cyclohexane(D,D,D)]—[phenyl]—[phenyl(3,4-F,F)] | 7 |
| (3-0205) | C3H7—[cyclohexane(D,D,D,D)]—[cyclohexane]—[phenyl(3,4,5-F,F,F)] | 5 |
| (3-0206) | C3H7—[cyclohexane]—[cyclohexane(D,D,D)]—[phenyl-OCF3] | 10 |
| (3-0207) | C3H7—[cyclohexane(D,D,D)]—[phenyl(F,F)]—C≡C—[phenyl(3,4-F,F)] | 6 |
| (3-0208) | C4H9—[phenyl(2-F)]—[phenyl]—C≡C—[phenyl(3,4-F,F)] | 6 |
| (3-0209) | C3H7—[cyclohexene]—[cyclohexane]—C5H11 | 5 |
| (3-0210) | CH2=CH—[cyclohexane]—[cyclohexane]—C5H11 | 10 |
| (3-0211) | CH2=CH-CH2—[cyclohexane]—[cyclohexane]—C3H7 | 15 |
| (3-0212) | CH2=CH—[cyclohexane]—[cyclohexane]—[phenyl]—CH3 | 15 |
| (3-0213) | C3H7—[cyclohexane]—[cyclohexane]—[phenyl]—CH3 | 5 | was prepared and various characteristics of the composition were measured. The results are as follows.

| | |
|---|---|
| $T_{N-I}$ | 100.0° C. |
| $T_{\to N}$ | −40.0° C. |

-continued

| | |
|---|---|
| Vth | 1.80 V |
| $\Delta\epsilon$ | 6.9 |
| $\Delta n$ | 0.114 |
| $\eta$ | 12.3 c.p. |

Specific resistance before the test: 4.1×10$^{13}$ Ω·cm

Specific resistance after heating acceleration test: 1.0×10$^{13}$ Ω·cm

Since this nematic liquid crystal composition has high specific resistance after the heating acceleration test, it can be understood that it is stable against heat. Also, when twisted nematic and super twisted nematic liquid crystal display systems were prepared using this composition as a constituting material, it was confirmed that they were excellent display systems which do not generate flicker.

In addition, when temperature-dependency of threshold voltage at from −10° C. to 60° C. was measured as an electro-optical characteristic using the thus obtained TN-LCD, it was 1.7 mV/° C. showing that a liquid crystal display system having excellent display characteristics was obtained.

Example 10

A nematic liquid crystal composition (3-03) comprising the following compounds

| | | (% by weight) |
|---|---|---|
| (3-0301) | 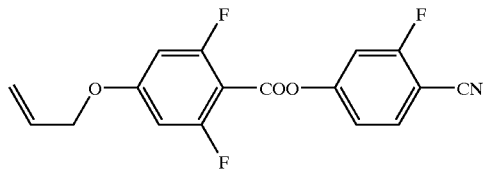 | 5 |
| (3-0302) | 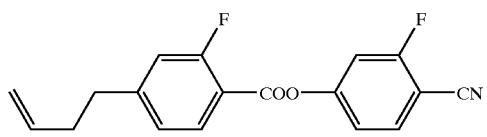 | 5 |
| (3-0303) | 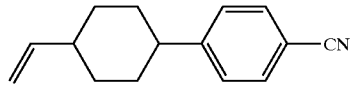 | 8 |
| (3-0304) | 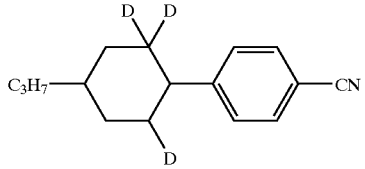 | 2 |
| (3-0305) | 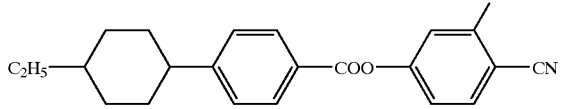 | 5 |
| (3-0306) | 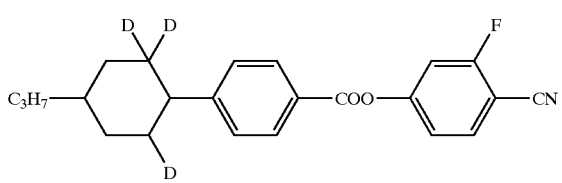 | 5 |
| (3-0307) | 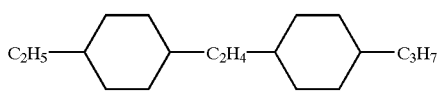 | 5 |
| (3-0308) | 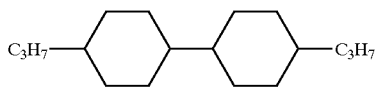 | 5 |
| (3-0309) |  | 15 |

-continued

| | | (% by weight) |
|---|---|---|
| (3-0310) | [structure: allyl-cyclohexyl-cyclohexyl-C3H7] | 15 |
| (3-0311) | [structure: vinyl-cyclohexyl-cyclohexyl-phenyl-CH3] | 5 |
| (3-0312) | [structure: C3H7-cyclohexyl-cyclohexyl-C2H4-phenyl-CH3] | 5 |
| (3-0313) | [structure: C3H7-phenyl-C≡C-phenyl-OC2H5] | 10 |
| (3-0314) | [structure: C5H11-phenyl-C≡C-phenyl-OC2H5] | 10 | was prepared and various characteristics of the composition were measured. The results are as follows.

| | |
|---|---|
| $T_{N-I}$ | 74.0° C. |
| $T_{\to N}$ | −20.0° C. |
| Vth | 1.32 V |
| $\Delta\epsilon$ | 10.8 |
| $\Delta n$ | 0.130 |
| $\eta$ | 13.9 c.p. |

In addition, a mixed liquid crystal composition was prepared by adding a chiral substance "S-811" (manufactured by Merck) to this nematic liquid crystal composition. On the other hand, a cell for STN-LCD use having a twist angle of 220 degree was prepared by effecting formation of the orientation film through the rubbing of an organic film of "Sun Ever 610" (manufactured by Nissan Chemical Industries) on the facing transparent flat electrode. The aforementioned mixed liquid crystal composition was injected into the thus prepared cell to construct a liquid crystal display system, and its display characteristics were measured. As the result, a liquid crystal display system was obtained which showed STN-LCD display characteristics having particularly excellent effects in terms of low threshold voltage, high multiplexing properties, improved flicker and crosstalk phenomena on the display screen, quick response and viewing angle characteristics having small parallax.

In this connection, the chiral substance was added in such an amount that natural helical pitch P of the mixed liquid crystal composition and cell thickness d of the display cell became $\Delta n \cdot d = 0.85$ and $d/P = 0.53$ by the addition of the chiral substance.

Example 11

A nematic liquid crystal composition (3-04) comprising the following compounds

| | | (% by weight) |
|---|---|---|
| (3-0401) | [structure: allyl-difluorophenyl-COO-fluorophenyl-CN] | 5 |
| (3-0402) | [structure: allyl-trifluorophenyl-COO-fluorophenyl-CN] | 5 |

-continued

| | | (% by weight) |
|---|---|---|
| (3-0403) | [structure] | 5 |
| (3-0404) | [structure] | 5 |
| (3-0405) | [structure] | 5 |
| (3-0406) | [structure] | 5 |
| (3-0407) | [structure] | 5 |
| (3-0408) | [structure] | 5 |
| (3-0409) | [structure] | 5 |
| (3-0410) | [structure] | 5 |
| (3-0411) | [structure] | 15 |
| (3-0412) | [structure] | 15 |
| (3-0413) | [structure] | 10 |

-continued

| | (% by weight) |
|---|---|
| (3-0414)  | 10 | was prepared and various characteristics of the composition were measured. The results are as follows.

| | |
|---|---|
| $T_{N-I}$ | 82.1° C. |
| $T_{\to N}$ | −30.0° C. |
| Vth | 0.81 V |
| Δε | 21.2 |
| Δn | 0.107 |
| η | 36.5 c.p. |

Specific resistance before the test: $8.0 \times 10^{11}$ Ω·cm

Specific resistance after heating acceleration test: $3.2 \times 10^{11}$ Ω·cm

Since this nematic liquid crystal composition has high specific resistance after the heating acceleration test, it can be understood that it is stable against heat. Also, when a twisted nematic liquid crystal display systems was prepared using this composition as a constituting material, it was confirmed that it was excellent display system which does not generate flicker.

In addition, when temperature-dependency of threshold voltage at from −10° C. to 40° C. was measured as an electro-optical characteristic using the thus obtained TN-LCD, it was 1.0 mV/° C. showing that a liquid crystal display system having excellent display characteristics was obtained. Its response at a low temperature was also excellent.

Example 12

A nematic liquid crystal composition (3-05) comprising the following compounds

| | (% by weight) |
|---|---|
| (3-0501) 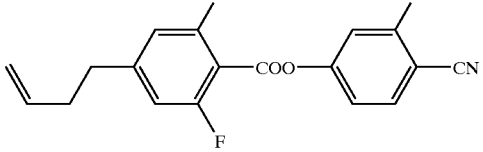 | 5 |
| (3-0502) 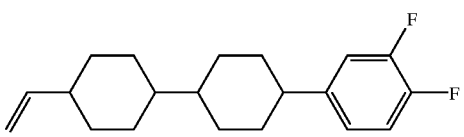 | 10 |
| (3-0503) 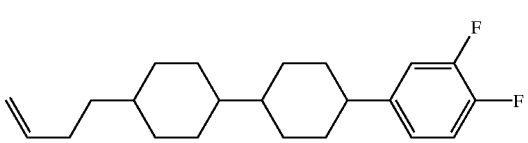 | 10 |
| (3-0504) 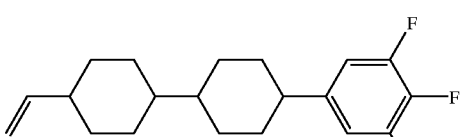 | 10 |
| (3-0505) 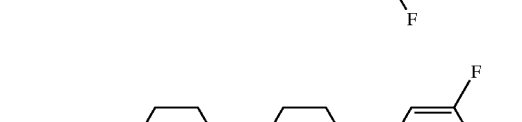 | 10 |

-continued

| | | (% by weight) |
|---|---|---|
| (3-0506) |  | 10 |
| (3-0507) | 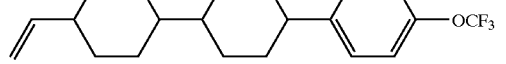 | 10 |
| (3-0508) | 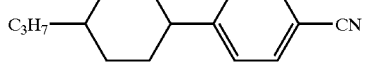 | 5 |
| (3-0509) | 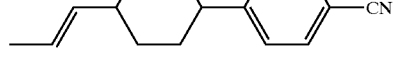 | 5 |
| (3-0510) | 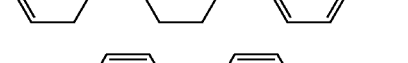 | 5 |
| (3-0511) |  | 5 |
| (3-0512) |  | 10 |
| (3-0513) | 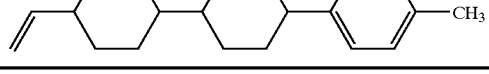 | 5 | was prepared and various characteristics of the composition were measured. The results are as follows.

| | |
|---|---|
| $T_{N-I}$ | 83.0° C. |
| $T_{\to N}$ | −70.0° C. |
| Vth | 1.32 V |
| Δε | 10.0 |
| Δn | 0.094 |
| η | 19.1 c.p. |

Specific resistance before the test: $4.1 \times 10^{12}$ Ω·cm

Specific resistance after heating acceleration test: $1.0 \times 10^{12}$ Ω·cm

Since this nematic liquid crystal composition has high specific resistance after the heating acceleration test, it can be understood that it is stable against heat. Also, when a liquid crystal display cell having an orientation film of "Sun Ever 610" was prepared using this composition as a constituting material, it showed a high tilt angle.

Example 13

A nematic liquid crystal composition (3-08) comprising the following compounds

| | | (% by weight) |
|---|---|---|
| (3-0801) | 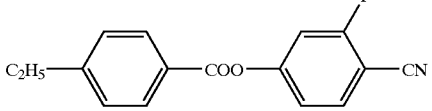 | 8 |

-continued

| | | (% by weight) |
|---|---|---|
| (3-0802) | C₃H₇–⌬–COO–⌬(F)–CN | 5 |
| (3-0803) | C₄H₉–⌬–COO–⌬(F)–CN | 8 |
| (3-0804) | CH₂=CH-CH₂-CH₂–⌬–COO–⌬(F)–CN | 4 |
| (3-0805) | CH₃-CH=CH-CH₂–⌬–COO–⌬(F)–CN | 4 |
| (3-0806) | C₅H₁₁–⌬–COO–⌬(F)–CN | 7 |
| (3-0807) | C₄H₉–⌬(F,F)–COO–⌬(F)–CN | 5 |
| (3-0808) | C₅H₁₁–⌬(F,F)–COO–⌬(F)–CN | 5 |
| (3-0809) | CH₂=CH–Cy–Cy–C₅H₁₁ | 10 |
| (3-0810) | CH₂=CH–Cy–Cy–⌬(F,F) | 17 |
| (3-0811) | C₃H₇–Cy–⌬–C≡C–⌬–C₂H₅ | 7 |
| (3-0812) | C₄H₉–Cy–⌬–C≡C–⌬–C₂H₅ | 6 |

-continued (% by weight)

| | | |
|---|---|---|
| (3-0813) | 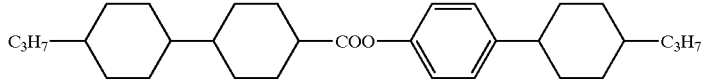 | 7 |
| (3-0814) | 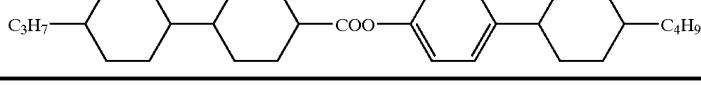 | 7 | was prepared and various characteristics of the composition were measured. The results are as follows.

| $T_{N-I}$ | 91.7° C. |
|---|---|
| $T_{\to N}$ | −50.0° C. |
| Vth | 1.32 V |
| Δε | 18.9 |
| Δn | 0.145 |
| η | 44.8 c.p. |

In addition, a mixed liquid crystal composition was prepared by adding a chiral substance "S-811" (manufactured by Merck) to this nematic liquid crystal composition. On the other hand, a cell for STN-LCD use having a twist angle of 240 degree was prepared by effecting formation of the orientation film through the rubbing of an organic film of "Sun Ever 610" (manufactured by Nissan Chemical Industries) on the facing transparent flat electrode. The aforementioned mixed liquid crystal composition was injected into the thus prepared cell to construct a liquid crystal display system, and its display characteristics were measured. As the result, a liquid crystal display system was obtained which showed STN-LCD display characteristics having particularly excellent effects in terms of low threshold voltage, high multiplexing properties, improved flicker and crosstalk phenomena on the display screen and viewing angle characteristics having small parallax.

In this connection, the chiral substance was added in such an amount that natural helical pitch P of the mixed liquid crystal composition and cell thickness d of the display cell became Δn·d=0.85 and d/P=0.53 by the addition of the chiral substance.

STN-LCD display characteristics at a twist angle of 240 degree

| Vth | 0.98 V |
|---|---|
| γ | 1.027 |
| Δ(Vth)/Δ(T) | 1.3 mV/° C. |

The following nematic liquid crystal compositions are prepared in the same manner as described in Example 8.
Composition (3-08-01)=compound (3-0808)→compound: side chain group (I-al) basic structure (I-16) polar group
Composition (3-08-02)=compound (3-0808)→compound: side chain group (I-am) basic structure (I-16) polar group
Composition (3-08-03)=compound (3-0808)→compound: side chain group (I-an) basic structure (I-16) polar group
Composition (3-08-04)=compound (3-0808)→compound: side chain group (I-al) basic structure (I-17) polar group
Composition (3-08-05)=compound (3-0808)→compound: side chain group (I-am) basic structure (I-17) polar group
Composition (3-08-06)=compound (3-0808)→compound: side chain group (I-an) basic structure (I-17) polar group
Composition (3-08-07)=compound (3-0808)→compound: side chain group (I-d) basic structure (I-7) polar group
Composition (3-08-08)=compound (3-0808)→compound: side chain group (I-al) basic structure (I-15) polar group
Composition (3-08-09)=compound (3-0808)→compound: side chain group (I-am) basic structure (I-15) polar group
Composition (3-08-10)=compound (3-0808)→compound: side chain group (I-an) basic structure (1-15) polar group
Similar to this example, these nematic liquid crystal compositions (3-08-01) to (3-08-10) showed excellent display characteristics. Among them, composition (3-08-02), composition (3-08-05) and composition (3-08-09) showed more excellent characteristics.

Example 14

A nematic liquid crystal composition (3-09) comprising the following compounds (% by weight)

| | | |
|---|---|---|
| (3-0901) | 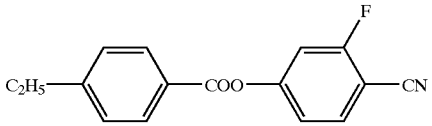 | 9 |

-continued
| | | (% by weight) |
|---|---|---|
| (3-0902) |  | 5 |
| (3-0903) |  | 10 |
| (3-0904) |  | 8 |
| (3-0905) |  | 8 |
| (3-0906) |  | 10 |
| (3-0907) |  | 8 |
| (3-0908) |  | 7 |
| (3-0909) |  | 5 |
| (3-0910) |  | 10 |
| (3-0911) |  | 10 |
| (3-0912) |  | 3 |
| (3-0913) |  | 7 | was prepared and various characteristics of the composition were measured. The results are as follows.

| $T_{N-I}$ | 89.1° C. |
|---|---|
| $T_{\to N}$ | −50.0° C. |
| Vth | 1.12 V |
| $\Delta\epsilon$ | 16.7 |
| $\Delta n$ | 0.144 |
| $\eta$ | 32.1 c.p. |

In addition, a mixed liquid crystal composition was prepared by adding a chiral substance "S-811" (manufactured by Merck) to this nematic liquid crystal composition. On the other hand, a cell for STN-LCD use having a twist angle of 240 degree was prepared by effecting formation of the orientation film through the rubbing of an organic film of "Sun Ever 610" (manufactured by Nissan Chemical Industries) on the facing transparent flat electrode. The aforementioned mixed liquid crystal composition was injected into the thus prepared cell to construct a liquid crystal display system, and its display characteristics were measured. As the result, a liquid crystal display system was obtained which showed STN-LCD display characteristics having particularly excellent effects in terms of low threshold voltage, high multiplexing properties, improved flicker and crosstalk phenomena on the display screen and viewing angle characteristics having small parallax.

In this connection, the chiral substance was added in such an amount that natural helical pitch P of the mixed liquid crystal composition and cell thickness d of the display cell became $\Delta n \cdot d = 0.85$ and $d/P = 0.53$ by the addition of the chiral substance.

STN-LCD display characteristics at a twist angle of 240 degree

| Vth | 0.99 V |
|---|---|
| $\gamma$ | 1.029 |
| $\Delta(Vth)/\Delta(T)$ | 1.2 mV/° C. |

The following nematic liquid crystal compositions are prepared in the same manner as described in Example 8.

Composition (3-09-01)=compound (3-0904)→compound: side chain group (I-al) basic structure (I-16) polar group Composition (3-09-02)=compound (3-0904)→compound: side chain group (I-am) basic structure (I-16) polar group Composition (3-09-03)=compound (3-0904)→compound: side chain group (I-an) basic structure (I-16) polar group Composition (3-09-04)=compound (3-0901)→compound: side chain group (I-al) basic structure (I-10) polar group Composition (3-09-05)=compound (3-0901)→compound: side chain group (I-am) basic structure (I-10) polar group Composition (3-09-06)=compound (3-0901)→compound: side chain group (I-an) basic structure (I-10) polar group Composition (3-09-07)=compound (3-0905)→compound: side chain group (I-al) basic structure (I-17) polar group Composition (3-09-08)=compound (3-0905)→compound: side chain group (I-am) basic structure (I-17) polar group Composition (3-09-09)=compound (3-0905)→compound: side chain group (I-an) basic structure (I-17) polar group Composition (3-09-10)=compound (3-0905)→compound: side chain group (I-am) basic structure (I-14) polar group Similar to this example, these nematic liquid crystal compositions (3-09-01) to (3-09-10) showed excellent display characteristics. Among them, composition (3-09-01), composition (3-09-02) and composition (3-09-08) showed further improved threshold voltage and temperature-dependency and frequency dependency thereof.

Example 15

A nematic liquid crystal composition (3-10) comprising the following compounds

| | | (% by weight) |
|---|---|---|
| (3-1001) | $C_2H_5-\bigcirc-COO-\bigcirc(F)-CN$ | 9 |
| (3-1002) | $C_3H_7-\bigcirc-COO-\bigcirc(F)-CN$ | 5 |
| (3-1003) | $C_4H_9-\bigcirc-COO-\bigcirc(F)-CN$ | 10 |

-continued

| | (% by weight) |
|---|---|
| (3-1004) 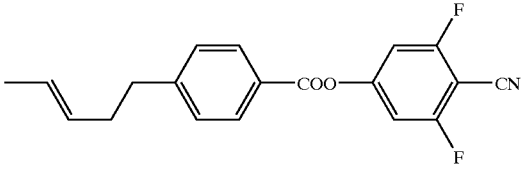 | 8 |
| (3-1005) 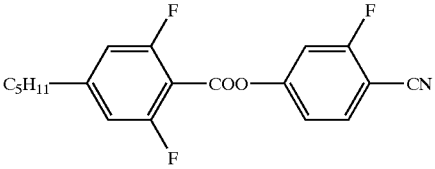 | 8 |
| (3-1006) 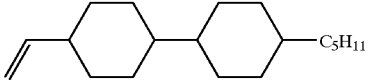 | 10 |
| (3-1007) 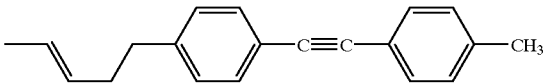 | 8 |
| (3-1008) 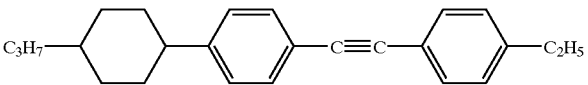 | 7 |
| (3-1009) 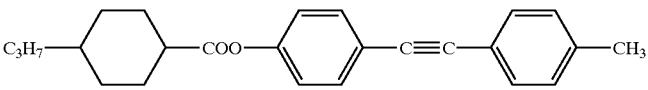 | 5 |
| (3-1010)  | 10 |
| (3-1011) 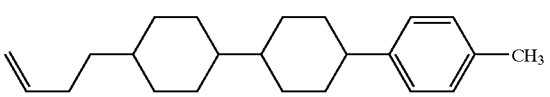 | 10 |
| (3-1012) 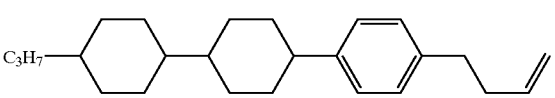 | 3 |
| (3-1013) 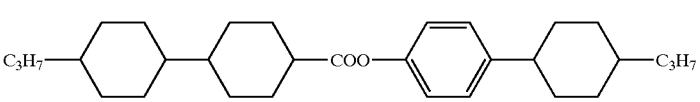 | 7 | was prepared and various characteristics of the composition were measured. The results are as follows.

| | |
|---|---|
| $T_{N-I}$ | 89.0° C. |
| $T_{\to N}$ | −50.0° C. |
| Vth | 1.13 V |
| Δε | 16.9 |
| Δn | 0.144 |
| η | 33.6 c.p. |

In addition, a mixed liquid crystal composition was prepared by adding a chiral substance "S-811" (manufactured by Merck) to this nematic liquid crystal composition. On the other hand, a cell for STN-LCD use having a twist angle of 240 degree was prepared by effecting formation of the orientation film through the rubbing of an organic film of "Sun Ever 610" (manufactured by Nissan Chemical Industries) on the facing transparent flat electrode. The aforementioned mixed liquid crystal composition was injected into the thus prepared cell to construct a liquid crystal display system, and its display characteristics were measured. As the result, a liquid crystal display system was obtained which showed STN-LCD display characteristics having particularly excellent effects in terms of low threshold voltage, high multiplexing properties, improved flicker and crosstalk phenomena on the display screen and viewing angle characteristics having small parallax.

In this connection, the chiral substance was added in such an amount that natural helical pitch P of the mixed liquid crystal composition and cell thickness d of the display cell became Δn·d=0.85 and d/P=0.53 by the addition of the chiral substance.

STN-LCD display characteristics at a twist angle of 240 degree

| | |
|---|---|
| Vth | 1.13 V |
| γ | 1.031 |
| Δ(Vth)/Δ(T) | 1.3 mV/° C. |

Example 16

The nematic liquid crystal composition (1-16) of the present invention showed the following additional characteristics. When wavelength dispersion of the birefringence of the nematic liquid crystal composition was measured, the light wavelength ratio of 400 nm to 650 nm was 1.15 or more. Since this liquid crystal material shows more larger retardation based on the difference in the light wavelength, it is useful in a novel reflection type liquid crystal color display system in which color display is carried out making use of birefringence of liquid crystal and retardation film without using color filter layers.

Example 17

The nematic liquid crystal compositions of the present invention, particularly (1-10), (1-11), (1-13), (1-14), (3-02), (3-03), (3-05), (3-09) and (3-10), showed the following additional characteristics. When a formula $\omega d=2\times 10^{12}\times S^{-1.4031}$ was defined as the relaxation frequency which is defined using a liquid crystal constituting factor of these liquid crystal compositions, $S=(\eta\times <a>^3)^{-1}$ {wherein η represents viscosity of a liquid crystal composition (unit, c.p.) and <a> represents average molecular length of the liquid crystal composition (unit, Å)}, and F was defined as the execution frequency practically applied to the liquid crystal layer, which is defined by the frame frequency and/or duty numbers related to the driving of the liquid crystal composition as a display, a function of $1.0\times 10^2 \geq \omega d/F \geq 5.0\times 10^{-1}$ was found within the driving temperature range. Because of this, a problem of not changing driving voltage within the frequency range corresponding to various cases of the multiplexing properties or of sudden increase in the driving voltage at a low temperature due to increase in the multiplexing properties (duty numbers) can be made better. Such a characteristic feature seems to be originated from the construction of the liquid crystal component A. As a consequence, liquid crystal display systems having improved display characteristics can be obtained by the use of the liquid crystal composition of the present invention. Particularly, excellent driving characteristics and display characteristics were obtained in the TN-LCD and STN-LCD liquid crystal display systems which require large quantity of information.

The nematic liquid crystal composition of the present invention can provide liquid crystal materials in response to desired purposes even by its addition in a small amount without spoiling other characteristics. More particularly, it provides a nematic liquid crystal composition which has such a temperature range that low temperature driving can be effected, shows more quicker response against driving voltage and can effect the driving at lower voltage. In consequence, liquid crystal display systems in which flicker and crosstalk phenomena on the display screen are improved can be obtained by the use of the liquid crystal composition of the present invention. In additions thickness d of the liquid crystal layer can be reduced when the birefringence is increased and the response characteristics can therefore be improved, so that excellent driving characteristics and display characteristics can be obtained particularly in the TN-LCD and STN-LCD liquid crystal display systems which require large quantity of information.

While the invention has been described in detail and with reference to specific examples thereof, it will be apparent to one skilled in the art that various changes and modifications can be made therein without departing from the spirit and scope thereof.

What is claimed is:

1. A compound, represented by the general formula (II):

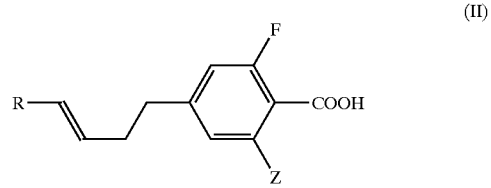

wherein R represents a hydrogen atom or a straight chain alkyl group having 1 to 7 carbon atoms and Z represents a hydrogen atom or a fluorine atom, provided that when Z is a hydrogen atom, R is an alkyl group having 2 to 7 carbon atoms.

2. A compound, represented by the general formula (II):

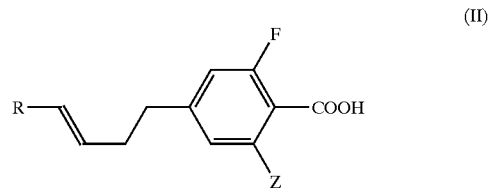

wherein R represents a hydrogen atom or a straight chain alkyl group having 1 to 7 carbon atoms and wherein Z represents a fluorine atom.

3. A compound, represented by the general formula (II):

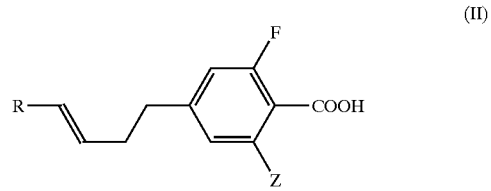

wherein R represents a straight chain alkyl group having 2 to 7 carbon atoms and Z represents a hydrogen atom.

* * * * *